US012383579B2

(12) United States Patent
Alverdy et al.

(10) Patent No.: US 12,383,579 B2
(45) Date of Patent: Aug. 12, 2025

(54) MATERIALS AND METHODS OF USING AN INHIBITOR OF PLASMINOGEN ACTIVATION TO TREAT ANASTOMOTIC LEAK

(71) Applicants: THE UNIVERSITY OF CHICAGO, Chicago, IL (US); RUSH UNIVERSITY MEDICAL CENTER, Chicago, IL (US)

(72) Inventors: John C. Alverdy, Glenview, IL (US); Olga Y. Zaborina, Brookfield, IL (US); Richard A. Jacobson, Chicago, IL (US)

(73) Assignees: The University of Chicago, Chicago, IL (US); Rush University Medical Center, Chicago, IL (US)

( * ) Notice: Subject to any disclaimer, the term of this patent is extended or adjusted under 35 U.S.C. 154(b) by 1109 days.

(21) Appl. No.: 17/049,793

(22) PCT Filed: Apr. 23, 2019

(86) PCT No.: PCT/US2019/028748
§ 371 (c)(1),
(2) Date: Oct. 22, 2020

(87) PCT Pub. No.: WO2019/209844
PCT Pub. Date: Oct. 31, 2019

(65) Prior Publication Data
US 2021/0252040 A1    Aug. 19, 2021

Related U.S. Application Data

(60) Provisional application No. 62/661,415, filed on Apr. 23, 2018.

(51) Int. Cl.
*A61K 31/80*    (2006.01)
*A61K 9/00*    (2006.01)
(Continued)

(52) U.S. Cl.
CPC ............ *A61K 31/80* (2013.01); *A61K 31/196* (2013.01); *A61K 31/197* (2013.01); *A61K 38/57* (2013.01); *A61P 31/04* (2018.01); *A61P 41/00* (2018.01)

(58) Field of Classification Search
None
See application file for complete search history.

(56) References Cited

U.S. PATENT DOCUMENTS 9,937,199 B2    4/2018    Alverdy
2012/0010557 A1    1/2012    Heger

FOREIGN PATENT DOCUMENTS

WO    WO 2014/028052 A1    2/2014
WO    WO 2017/123653 A1    7/2017
(Continued)

OTHER PUBLICATIONS

Peter et al., "Relation between postoperative ileus and anastomotic leakage after colorectal resection: a post hoc analysis of a prospective randomized controlled trial", The Association of Coloproctology of Great Britain and Ireland, 19, 667-674, 2016. (Year: 2016).*
(Continued)

*Primary Examiner* — Kyung S Chang
(74) *Attorney, Agent, or Firm* — Leydig, Voit & Mayer, Ltd.

(57) ABSTRACT

Disclosed herein is the de novo synthesis of phosphorylated polyethylene glycol compounds with three defined ABA (hy-drophilic/-phobic/-philic) structures: ABA-PEG10k-Pi10, ABA-PEG16k-Pi14, and ABA-PEG20k-Pi20 and linear polymer PEG20k-Pi20 absent of hydrophobic block. The disclosure also provides materials and methods for treating or reducing the risk or likelihood of developing, anastomotic leak or other microbe-mediated disorders by administering a
(Continued)

therapeutically effective amount of a plasminogen inhibitor such as tranexamic acid and/or a phosphate-loaded polymer.

8 Claims, 51 Drawing Sheets

Specification includes a Sequence Listing.

(51) Int. Cl.

| | | |
|---|---|---|
| A61K 31/195 | (2006.01) | |
| A61K 31/196 | (2006.01) | |
| A61K 31/197 | (2006.01) | |
| A61K 31/77 | (2006.01) | |
| A61K 38/57 | (2006.01) | |
| A61P 1/00 | (2006.01) | |
| A61P 31/04 | (2006.01) | |
| A61P 41/00 | (2006.01) | |
| C08G 65/22 | (2006.01) | |
| C08G 65/26 | (2006.01) | |
| C08G 65/327 | (2006.01) | |

(56) References Cited

FOREIGN PATENT DOCUMENTS

| WO | WO 2018/014894 A1 | 1/2018 |
|---|---|---|
| WO | WO 2018/064536 A1 | 4/2018 |
| WO | WO 2019/007469 A1 | 1/2019 |

OTHER PUBLICATIONS

Choudhuri et al., "Predictors of septic shock following anastomotic leak after major gastrointestinal surgery: An audit from a tertiary care institute", Indian Journal of Critical Care Medicine, Sep.-Oct. 2013, vol. 17, Issue 5. (Year: 2013).*
Aimes et al., "Matrix metalloproteinase-2 is an interstitial collagenase. Inhibitor-free enzyme catalyzes the cleavage of collagen fibrils and soluble native type I collagen generating the specific ¾- and ¼- length fragments," *J Biol Chem*, 270(11): 5872-5876 (Mar. 1995).
Almer et al., "Pharmacokinetics of tranexamic acid in patients with ulcerative colitis and in healthy volunteers after the single installation of 2 g rectally," *J Clin Pharmacol*, 32(1): 49-54 (Jan. 1992).
Altschul et al., "Gapped BLAST and PSI-BLAST: a new generation of protein database search programs," *Nucleic Acids Res*, 25(17): 3389-3402 (Sep. 1997).
Ambadapadi et al., "Reactive Center Loop (RCL) peptides derived from serpins display independent coagulation and immune modulating activities," *J Biol Chem*, 291(6): 2874-2887 (Feb. 2016).
Arumugam et al., "Temporal activity of plasminogen activators and matrix metalloproteinases during cutaneous wound repair," *Surgery*, 125(6): 587-593 (Jun. 1999).
Atkinson et al., "In the absence of a mechanical bowel prep, does the addition of pre-operative oral antibiotics to parental antibiotics decrease the incidence of surgical site infection after elective segmental colectomy?" *Surg Infect (Larchmt)*, 16(6): 728-732 (Jul. 2015).
Augustin et al., "Predominant role of host proteases in myocardial damage associated with infectious endocarditis induced by Enterococcus faecalis in a rat model," *Infect Immun*, 81(5): 1721-1729 (May 2013).
Banerjee et al., "Antifouling coatings: recent developments in the design of surfaces that prevent fouling by proteins, bacteria, and marine organisms," *Adv Mater*, 23(6): 690-718 (Feb. 2011).
Beaufort et al., "Activation of human pro-urokinase by unrelated proteases secreted by Pseudomonas aeruginosa," *Biochem J*, 428(3): 473-482 (May 2010) Biochemical Journal Immediate Publication published as manuscript BJ20091806.

Benachour et al., "Identification of secreted and surface proteins from Enterococcus faecalis," *Can J Microbiol*, 55(8): 967-974 (Aug. 2009).
Bergwitz et al., "Phosphate sensing," *Adv Chronic Kidney Dis*, 18(2): 132-144 (Mar. 2011); Author manuscript as published in PubMed, 25 pp.
Bhattacharya et al., "Bacterial plasminogen receptors utilize host plasminogen systems for effective invasion and dissemination," *J Biomed Biotechnol*, 2012, 482096 (Oct. 2012) (19 pages).
Bower et al., "Cell surface antigens of Mycoplasma species bovine group 7 bind to and activate plasminogen," *Infect Immun*, 71(8): 4823-4827 (Aug. 2003).
Boyle et al., "Plasminogen activation by invasive human pathogens," *Thromb Haemost*, 77(1): 1-10 (Jan. 1997).
Branagan et al., "Prognosis after anastomotic leakage in colorectal surgery," *Dis Colon Rectum*, 48(5): 1021-1026 (May 2005).
Camps et al., "Antifouling coatings influence both abundance and community structure of colonizing biofilms: a case study in the Northwestern Mediterranean Sea," *Appl Environ Microbiol*, 80(16): 4821-4831 (Aug. 2014).
Cederholm-Williams et al., "Kinetics of the reactions between streptokinase, plasmin and alpha 2-antiplasmin," *Eur J Biochem*, 100(1): 125-132 (Oct. 1979).
Clarke et al., "Preoperative oral antibiotics reduce septic complications of colon operations: results of prospective, randomized, double-blind clinical study," *Ann Surg*, 186(3): 251-258 (Sep. 1977).
Cohn et al., "Antibiotic protection of colon anastomoses," *Ann Surg*, 141(5): 707-713 (May 1955).
CRASH-2 Trial Collaborators et al., "Effects of tranexamic acid on death, vascular occlusive events, and blood transfusion in trauma patients with significant haemorrhage (CRASH-2): a randomized, placebo-controlled trial," *Lancet*, 376(9734): 23-32 (Jun. 2010).
Cronberg et al., "Disseminated intravascular coagulation in septicemia caused by beta-hemolytic streptococci," *Thromb Res*, 3: 405-411 (Oct. 1973).
Cubellis et al., "Receptor-mediated internalization and degradation of urokinase is caused by its specific inhibitor PAI-1," *EMBO J*, 9(4): 1079-1085 (Apr. 1990).
Diaz-Ramos et al., "alpha-Enolase, a multifunctional protein: its role on pathophysiological situations," *J Biomed Biotechnol*, 2012, 156795 (Oct. 2012) (12 pages).
Dimitriou et al., "A general approach to controlling the surface composition of poly(ethylene oxide)-based block copolymers for antifouling coatings," *Langmuir*, 27(22): 13762-13772 (Nov. 2011).
Fontan et al., "Antibodies to streptococcal surface enolase react with human alpha-enolase: implications in poststreptococcal sequelae," *J Infect Dis*, 182(6): 1712-1721 (Dec. 2000).
Gao et al., "Rationally designed dual functional block copolymers for bottlebrush-like coatings: In vitro and in vivo antimicrobial, antibiofilm, and antifouling properties," *Acta Biomater*, 51, 112-124 (Mar. 2017).
Gong et al., "Inflammatory macrophage migration requires MMP-9 activation by plasminogen in mice," *J Clin Invest*, 118(9): 3012-3024 (Sep. 2008).
Hara et al., "Molecular imaging of fibrin deposition in deep vein thrombosis using fibrin-targeted near-infrared fluorescence," *JACC Cardiovasc Imaging*, 5(6): 607-615 (Jun. 2012).
Hayakawa et al., "Dramatic changes of the gut flora immediately after severe and sudden insults," *Dig Dis Sci*, 56(8): 2361-2365 (Sep. 2011).
Hedrick et al., "Anastomotic leak and the loop ileostomy: friend or foe?" *Dis Colon Rectum*, 49(8): 1167-1176 (Aug. 2006).
Hesp et al., "Histological features of wound repair: a comparison between experimental ileal and colonic anastomoses," *Br J Exp Pathol*, 66(5): 511-518 (Oct. 1985).
Hyoju et al., "Oral polyphosphate suppresses bacterial collagenase production and prevents anastomotic leak due to Serratia marcescens and Pseudomonas aeruginosa," *Ann Surg*, 267(6): 1112-1118 (Jun. 2017); Author manuscript as published in PubMed, 15 pp.
Isenring et al., "*Streptococcus gallolyticus* subsp. gallolyticus endocarditis isolate interferes with coagulation and activates the contact system," *Virulence*, 9(1): 248-261 (Jan. 2018).

(56) References Cited

OTHER PUBLICATIONS

Itzek et al., "Contribution of plasminogen activation towards the pathogenic potential of oral streptococci," PLoS One, 5(11): e13826 (10 pages) (Nov. 2010).
Jacobson et al., "Prevention of anastomotic leak via local applciation of tranexamis acid to target bacterial-mediated plasmingogen activation: a practical solution to a complex problem," Ann Surg., (Dec. 2019) DOI: 10.1097/SLA.0000000000003733 (9 pages).
Jacovina et al., "Neuritogenesis and the nerve growth factor-induced differentiation of PC-12 cells requires annexin II-mediated plasmin generation," J Biol Chem, 276(52): 49350-49358 (Dec. 2001).
Jensen et al., "RhlR expression in Pseudomonas aeruginosa is modulated by the Pseudomonas quinolone signal via PhoB-dependent and -independent pathways," J Bacteriol, 188(24): 8601-8606 (Dec. 2006).
Johnston et al., "Evaluation of military use of tranexamic acid and associated thromboembolic events," JAMA Surg, 153(2): 169-175 (Feb. 2018).
Karliczek et al., "Surgeons lack predictive accuracy for anastomotic leakage in gastrointestinal surgery," Int J Colorectal Dis, 24(5): 569-576 (May 2009).
Kawao et al., "Role of plasminogen in macrophage accumulation during liver repair," Thromb Res, 125(5): e214-e221 (May 2010).
Kingham et al., "Colonic anastomotic leak: risk factors, diagnosis, and treatment," J Am Coll Surg, 208(2): 269-278 (Feb. 2009).
Kiran et al., "Combined preoperative mechanical bowel preparation with oral antibiotics significantly reduces surgical site infection, anastomotic leak, and ileus after colorectal surgery," Ann Surg, 262(3): 416-425 (Sep. 2015).
Kolate et al., "PEG—a versatile conjugating ligand for drugs and drug delivery systems," J Control Release, 192, 67-81 (Oct. 2014).
Kunert et al., "Immune evasion of the human pathogen Pseudomonas aeruginosa: elongation factor Tuf is a factor H and plasminogen binding protein," J Immunol, 179(5): 2979-2988 (Sep. 2007).
Kuusela et al., "Binding and activation of plasminogen at the surface of Staphylococcus aureus. Increase in affinity after conversion to the Lys form of the ligand," Eur J Biochem, 193(3): 759-765 (Nov. 1990).
Lahteenmaki et al., "Bacterial metastasis: the host plasminogen system in bacterial invasion," Trends Microbiol, 13(2): 79-85 (Feb. 2005).
Law et al., "Anastomotic leakage is associated with poor long-term outcome in patients after curative colorectal resection for malignancy," J Gastrointest Surg, 11(1): 8-15 (Jan. 2007).
Li et al., "Synthesis of amphiphilic copolymer brushes: poly(ethylene oxide)-graft-polystyrene," J Polym Sci A Polym Chem, 44, 4361-4371 (Jun. 2006).
Liechty et al., "Polymers for drug delivery systems," Annu Rev Chem Biomol Eng, 1, 149-173 (Aug. 2010); Author manuscript as published in PubMed, 29 pp.
Lijnen et al., "Regulation of gelatinase activity in mice with targeted inactivation of components of the plasminogen/plasmin system," Thromb Haemost, 79(6): 1171-1176 (Jun. 1998).
Luong et al., "Emergence of the P2 phenotype in Pseudomonas aeruginosa PAO1 strains involves various mutations in mexT or mexF," J Bacteriol, 196(2): 504-513 (Jan. 2014).
Mangold et al., "Hetero-multifunctional poly(ethylene glycol) copolymers with multiple hydroxyl groups and a single terminal functionality," Macromol Rapid Commun, 31(3): 258-264 (Feb. 2010).
McArdle et al., "Impact of anastomotic leakage on long-term survival of patients undergoing curative resection for colorectal cancer," Br J Surg, 92(9): 1150-1154 (Sep. 2005).
McCormack, "Tranexamic acid: a review of its use in the treatment of hyperfibrinolysis," Drugs, 72(5): 585-617 (Mar. 2012).
Merz et al., "Pilus retraction powers bacterial twitching motility," Nature, 407(6800): 98-102 (Sep. 2000).
Miles et al., "Alpha-enolase comes muscling in on plasminogen activation," Thromb Haemost, 90(4): 564-566 (Oct. 2003).
Miles et al., "Binding and activation of plasminogen on the platelet surface," J Biol Chem, 260(7): 4303-4311 (Apr. 1985).
Mirnezami et al., "Increased local recurrence and reduced survival from colorectal cancer following anastomotic leak: systematic review and meta-analysis," Ann Surg, 253(5): 890-899 (May 2011).
Molla et al., "Inactivation of various proteinase inhibitors and the complement system in human plasma by the 56-kilodalton proteinase from Serratia marcescens," Infect Immun, 57(6): 1868-1871 (Jun. 1989).
Noh et al., "Impact of anastomotic leakage on long-term oncologic outcome and its related factors in rectal cancer," Medicine, 95(30) (Jul. 2016) (7 pages).
Ohigashi et al., "Significant changes in the intestinal environment after surgery in patients with colorectal cancer," J Gastrointest Surg, 17(9): 1657-1664 (Sep. 2013).
Ojima et al., "Metagenomic analysis reveals dynamic changes of whole gut microbiota in the acute phase of intensive care unit patients," Dig Dis Sci, 61(6): 1628-1634 (Jun. 2016).
Olivas et al., "Intestinal tissues induce an SNP mutation in Pseudomonas aeruginosa that enhances its virulence: possible role in anastomotic leak," PLoS One, 7(8): e44326 (Aug. 2012) (11 pages).
Oliveira et al., "Mechanical bowel preparation for elective colorectal surgery. A prospective, randomized, surgeon-blinded trial comparing sodium phosphate and polyethylene glycol-based oral lavage solutions," Dis Colon Rectum, 40(5): 585-591 (May 1997).
Price et al., "Selective decontamination of the digestive tract and oropharynx: after 30 years of debate is the definitive answer in sight?" Curr Opin Crit Care, 22(2): 161-166 (Apr. 2016).
Qin et al., "Effects of Enterococcus faecalis fsr genes on production of gelatinase and a serine protease and virulence," Infect Immun, 68(5): 2579-2586 (May 2000).
Redlitz et al., "The role of an enolase-related molecule in plasminogen binding to cells," Eur J Biochem, 227(1-2): 407-415 (Jan. 1995).
Rømer et al., "Impaired wound healing in mice with a disrupted plasminogen gene," Nat Med., 2(3): 287-292 (Mar. 1996).
Rouch et al., "Small molecules inhibitors of plasminogen activator inhibitor-1-an overview," European Journal of Medicinal Chemistry, 92: 619-636 (Mar. 2015).
Scarborough et al., "Combined mechanical and oral antibiotic bowel preparation reduces incisional surgical site infection and anastomotic leak rates after elective colorectal resection: an analysis of colectomy-targeted ACS NSQIP," Ann Surg, 262(2): 331-337 (Aug. 2015).
Shafer et al., "Plasminogen activation in healing human wounds," Am J Pathol, 144(6): 1269-1280 (Jun. 1994).
Shakhsheer et al., "Morphine promotes colonization of anastomotic tissues with collagenase—producing Enterococcus faecalis and causes leak," J Gastrointest Surg, 20(10): 1744-1751 (Oct. 2016).
Shogan et al., "Collagen degradation and MMP9 activation by Enterococcus faecalis contribute to intestinal anastomotic leak," Sci Transl Med, 7(286), 286ra68 (May 2015); Author manuscript as published in PubMed, 27 pp.
Shogan et al., "Intestinal anastomotic injury alters spatially defined microbiome composition and function," Microbiome, 2, 35 (Sep. 2014) (10 pages).
Stern et al., "Agent-based model of epithelial host-pathogen interactions in anastomotic leak," J Surg Res, 184(2): 730-738 (Oct. 2013); Author manuscript as published in PubMed, 18 pp.
Sulniute et al., "Plasminogen is a critical regulator of cutaneous wound healing," Thromb Haemost, 115(5): 1001-1009 (May 2016).
Te Velde et al., "Impaired healing of cutaneous wounds and colonic anastomoses in mice lacking thrombin-activatable fibrinolysis inhibitor," J Thromb Haemost, 1(10): 2087-2096 (Oct. 2003).
Teillant et al., "Potential burden of antibiotic resistance on surgery and cancer chemotherapy antibiotic prophylaxis in the USA: a literature review and modelling study," Lancet Infect Dis, 15(12) (Oct. 2015) (11 pages).
Thomas et al., "Regulation of autolysis-dependent extracellular DNA release by Enterococcus faecalis extracellular proteases influences biofilm development," J Bacteriol, 190(16): 5690-5698 (Aug. 2008).
Vale et al., "Beyond killing: Can we find new ways to manage infection?" Evol Med Public Health, 2016(1): 148-157 (Apr. 2016).

(56) References Cited

OTHER PUBLICATIONS

Vilar et al., "Polymers and drug delivery systems," *Curr Drug Deliv*, 9(4) (Jul. 2012) (28 pages).
Waltz et al., "Cytokines induce urokinase-dependent adhesion of human myeloid cells. A regulatory role for plasminogen activator inhibitors," *J Clin Invest*, 91(4): 1541-1552 (Apr. 1993).
Wang et al., "Investigation of the role of hydrophilic chain length in amphiphilic perfluoropolyether/poly(ethylene glycol) networks: towards high-performance antifouling coatings," *Biofouling*, 27(10): 1139-1150 (Nov. 2011).
Weir et al., "Stool microbiome and metabolome differences between colorectal cancer patients and healthy adults," *PLoS One*, 8(8), e70803 (Aug. 2013) (10 pp.).
Wiman et al., "On the mechanism of the reaction between human alpha 2-antiplasmin and plasmin," *J Biol Chem*, 254(18): 9291-9297 (Sep. 1979).
Wu et al., "High-molecular-weight polyethylene glycol prevents lethal sepsis due to intestinal Pseudomonas aeruginosa," *Gastroenterology*, 126(2): 488-498 (Feb. 2004).
Xiao et al., "MvfR, a key Pseudomonas aeruginosa pathogenicity LTTR-class regulatory protein, has dual ligands," *Mol Microbiol*, 62(6): 1689-1699 (Dec. 2006).
Yuasa et al., "Fibrinolysis is essential for fracture repair and prevention of heterotopic ossification," *J Clin Invest*, 125(8): 3117-3131 (Aug. 2015).
Zaborin et al., "Membership and behavior of ultra-low-diversity pathogen communities present in the gut of humans during prolonged critical illness," *mBio*, 5(5): e01361-14 (Sep. 2014) (14 pages).
Zaborin et al., "Phosphate-containing polyethylene glycol polymers prevent lethal sepsis by multidrug-resistant pathogens," *Antimicrob Agents Chemother*, 58(2): 966-977 (Jan. 2014).
Zaborin et al., "Pseudomonas aeruginosa overrides the virulence inducing effect of opioids when it senses an abundance of phosphate," *PLoS One*, 7(4): e34883 (Apr. 2012) (11 pages).
Zaborin et al., "Red death in Caenorhabditis elegans caused by Pseudomonas aeruginosa PAO1," *Proc Natl Acad Sci USA*, 106(15): 6327-6332 (Apr. 2009).
Zaborina et al., "Dynorphin activates quorum sensing quinolone signaling in Pseudomonas aeruginosa," *PLOS Pathog*, 3(3), e35 (Mar. 2007) (15 pages).
Zaborina et al., "Host stress and virulence expression in intestinal pathogens: development of therapeutic strategies using mice and C. elegans," *Curr Pharm Des*, 17(13): 1254-1260 (Nov. 2011); Author manuscript as published in PubMed, 16 pp.
Zhou et al., "Amphiphilic triblock copolymers with PEGylated hydrocarbon structures as environmentally friendly marine antifouling and fouling-release coatings," *Biofouling*, 30(5): 589-604 (Apr. 2014).
Zhou et al., "Synthesis, characterization, and in vivo evaluation of poly(ethylene oxide-co-glycidol)-platinate conjugate," *Eur J Pharm Sci*, 41(3-4): 464-472 (Nov. 2010).
United States Patent Office, International Search Report in International Patent Application No. PCT/US2019/028748, 6 pp. (Aug. 16, 2019).
United States Patent Office, Written Opinion in International Patent Application No. PCT/US2019/028748, 6 pp. (Aug. 16, 2019).
International Bureau of WIPO, International Preliminary Report on Patentability in International Patent Application No. PCT/US2019/028748, 8 pp. (Oct. 27, 2020).
U.S. Appl. No. 16/338,330, filed Mar. 29, 2019.

\* cited by examiner (to be continued)

(continuation)

(to be continued)

(continuation)

MATERIALS AND METHODS OF USING AN INHIBITOR OF PLASMINOGEN ACTIVATION TO TREAT ANASTOMOTIC LEAK

CROSS-REFERENCE TO RELATED APPLICATIONS

This application is a U.S. national phase of International Patent Application No. PCT/US2019/028748, filed on Apr. 23, 2019, which claims the priority benefit under 35 U.S.C. § 119(e) of U.S. Provisional Patent Application No. 62/661,415, filed Apr. 23, 2018, the disclosure of each is incorporated herein by reference in its entirety.

STATEMENT OF GOVERNMENT SUPPORT

This invention was made with government support under GM062344 awarded by The National Institutes of Health. The government has certain rights in the invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 747335SequenceListing, 1037 bytes, created on Oct. 22, 2020.

FIELD

The disclosure relates generally to the fields of medical treatment and, more specifically, to the treatment or suppression of anastomotic leakage.

BACKGROUND

Anastomotic leak (AL) remains a significant source of morbidity and mortality following colon surgery for benign and malignant conditions, occurring after 5-20% of the roughly 300,000 resections performed in America every year. As a result, in cases involving an anastomosis in high risk areas such as the low colon and rectum, experienced surgeons routinely divert the fecal stream with an ileostomy to avoid the septic complications of a leak (2'). Given these observations, anastomotic leak (AL) can no longer be considered as much a problem of surgical technique as one of biology. Yet one consistent finding remains: in animal and human studies, antibiotics locally applied to anastomotic tissues results in reductions in the incidence of AL It is known that collagenolytic *Enterococcus faecalis* can cause AL in rodents through pathologic degradation of colonic submucosal collagen. The ubiquitous protease plasminogen (PLG) has a central role in collagen remodeling, and can be activated by pathogenic bacteria. The role of PLG in anastomotic healing is incompletely understood, and it is unknown whether *E. faecalis* or other opportunistic pathogens of the GI tract are capable of virulent activation of PLG.

The promiscuous use of antibiotics had led to the emergence of antibiotic resistance at an unprecedented pace and continues to place patients at risk for life-threatening infections following major surgery [1]. Many if not most of the pathogens that cause these infections use the intestinal tract as their primary site of colonization. Although surgeons routinely decontaminate the intestinal tract with antibiotics prior to surgery to prevent infection, this practice carries the unintended consequence of causing antibiotic resistance [2]. Furthermore, overuse of antibiotics can destroy the microbiome which normally protects against high risk pathogens [3]. A more evolutionarily stable strategy to this problem would be to develop compounds that can suppress pathogen virulence rather than kill bacteria [4]. In this manner, bacterial pathogenicity could be contained and the colonization resistance of the normally protective microbiota preserved.

Polyethylene glycol (PEG)-related polymers are known to suppress bacterial virulence without affecting bacterial growth. Initially PEG molecules were identified to function as anti-fouling coating agents capable of preventing bacterial adhesion to surfaces and subsequent biofilm formation [5-8]. Amphiphilic polymeric materials were most promising in this regard due to their dual surface functionality [9, 10]. The ability to attach diverse functional groups to PEG polymers has extended the medical applications of PEG derivative compounds especially as drug delivery systems [12-14].

Despite broader spectrum antibiotics and improved surgical technique, AL remains an immediate danger to patients [28-30]. The underlying pathophysiology of AL is multifactorial, involving both patient and operative factors [31]. Even when all risk factors are controlled and an operation is technically sound, however, leak rates remain unacceptably high with an immediate mortality rate of 10-15% [32].

SUMMARY

Disclosed herein is experimental evidence establishing the role of PLG in bacteria-induced AL and materials and methods for targeting this pathway. Many of the opportunistic pathogens of the intestinal tract, including *Pseudomonas aeruginosa* and other healthcare-acquired pathogens that cause serious post-operative infections, have become resistant to the antibiotics used for prophylaxis, indicating the need for alternative approaches to the problem of anastomotic leak. The disclosed materials and methods address a risk factor present in all gastrointestinal surgeries, i.e., the development of an anastomotic leak. The compounds administered in the methods according to the disclosure include any known plasminogen activator, any known phosphate-loaded polymer, or both a known plasminogen activator and a phosphate-loaded polymer. An exemplary plasminogen activator useful in the methods according to the disclosure is tranexamic acid (TXA) and an exemplary phosphate-loaded polymer is phosphorylated PEG such as phosphorylated high molecular weight PEG. In particular, the disclosure contemplates administration of a tri-phosphate block copolymer, e.g., ABA-PEG20k-Pi20 as a phosphorylated high molecular weight PEG. The methods according to the disclosure include treatment methods for patients with anastomotic leak or another microbe-mediated disorder and methods of reducing the risk of acquiring, i.e., reducing the likelihood of, anastomotic leak, or another microbe-mediated disorder.

More generally, the disclosure provides materials and methods for treating, preventing or suppressing diseases and conditions associated with pathogenic microbe-mediated epithelial diseases or disorders such as gastrointestinal infections or inflammation, or gastrointestinal anastomoses or anastomotic leaks, such as esophageal or intestinal anastomoses or anastomotic leaks. The materials for use in such circumstances are phosphorylated polyethylene glycol (Pi-PEG or P-PEG) compounds of a defined structure, such as an A-B-A triblock copolymer structure. Notably, the P-PEG materials of the disclosure comprise a hydrophobic core such as a diphenylmethyl moiety and the materials exhibit a substantially similar molecular weight wherein about 80%, 90%, 95%, 96%, 97% 98%, 99%, 99.5% or 99.9% of the P-PEG molecules have the same molecular weight (plus or minus 5% or 10%). The particular structure of the P-PEG and the relatively constant structure result in effects on epithelial cell diseases and disorders mediated by obligate or opportunistic microbial pathogens.

The inventors prepared phosphorylated PEG15-20 (Sigma), Pi-PEG15-20, and demonstrated that it can function in the intestine as an anti-virulence compound and prevent lethal-sepsis due to several healthcare acquired pathogens including *Pseudomonas aeruginosa* [3]. The phosphate content of this compound was shown to be particularly important for its protective effect.

Disclosed herein is compelling data generated in rodent models that demonstrate that AL can occur as a result of an infection of anastomotic tissue. The results obtained with these models demonstrate that pathobiota such as *Enterococcus faecalis* colonize tissues and produce collagenolytic enzymes that impair collagen deposition, a process vital to the integrity of a healing surgical wound (8', 9'). The mechanism of this effect relies on phosphosensory/phosphoregulatory circuits that are a universal feature of most bacteria and play a key role in virulence [15]. One obstacle of the previously used PEG 15-20 (Sigma) is that PEG 15-20 is not a pure tri-block polymer but rather a mixture of polymers of varying molecular weights including ABA (hydrophilic/-phobic/-philic) triblock, AB diblock and homopolymer poly(ethylene glycol) structures (FIG. 8). This situation limits the ability to further interrogate the molecular mechanisms by which the polymers protect both in vitro and in vivo, and the limited content of phosphate inhibits the opportunity of further improving the efficacy of the polymers. Therefore, the inventors performed de novo synthesis of a family of block copolymers with defined ABA structure as well as a complementary linear phosphorylated polymer. In all compounds, the inventors controlled the molecular weight and functional groups in order to more precisely define the amount of bound phosphorus. The anti-virulence capacity of the synthesized polymers was verified using the well-established model opportunistic pathogen *P. aeruginosa*.

One aspect of the disclosure is drawn to a pharmaceutical composition comprising a plasminogen inhibitor and a phosphate-loaded polymer. In some embodiments, the phosphate-loaded polymer is a phosphorylated polyethylene glycol. In some embodiments, the phosphorylated polyethylene glycol is ABA-PEG20k-Pi20. In some embodiments, the plasminogen inhibitor is tranexamic acid, F-aminocaproic acid, plasminogen activator inhibitor-1, plasminogen activator inhibitor-2, plasminogen activator inhibitor-3, antiplasmin, 5-Chloro-2-[{2-[4-(diphenylmethyl)piperazin-1-yl]-2-oxoethoxy}(28)acetyl]aminobenzoate (TM5275); 5-chloro-2-[[2-[2-[[3-(3-furanyl)phenyl]amino]-2-oxoethoxy]acetyl]amino]-benzoic acid (TM5441); the plasminogen inhibitor compounds disclosed in WO2007083689 A1 that are incorporated herein by reference, diketopiperazine compounds including XR334, XR330, XR1853, XR5082, XR5118, XR11211, and XR5967, flufenamic acid compounds including AR-H029953XX, benzofurna derivative WAY-140312, salicylindol derivative HP129 Fendosal, tiplaxtinin, diaplasinin, benzothiphene derivative S35225, menthol derivative inhibitor ZK4044, oxadiazolidinediones, oxadiazolidine; T-1776Na, tannic acid, epigallocatechin-3, 5-digallate, gallic acid, theaflavin, IMD-1622, azetidine derivative AZ3976, and embelin. The foregoing plasminogen inhibitors are disclosed in Rouch et al., European Journal of Medicinal Chemistry. Volume 92, pages 619-636 (2015), incorporated herein by reference in pertinent part. In some embodiments, the antiplasmin is alpha-2-antiplasmin. In some embodiments, the plasminogen inhibitor is tranexamic acid.

Another aspect of the disclosure is directed to a method of treating anastomotic leak comprising administering a therapeutically effective amount of a plasminogen inhibitor, wherein the plasminogen inhibitor is tranexamic acid, F-aminocaproic acid, plasminogen activator inhibitor-1, plasminogen activator inhibitor-2, plasminogen activator inhibitor-3, or antiplasmin. In some embodiments, the antiplasmin is alpha-2-antiplasmin. In some embodiments, the plasminogen inhibitor is tranexamic acid. In some embodiments, the anastomotic leak is associated with collagenolytic *Enterococcus faecalis*. In some embodiments, the anastomotic leak is associated with *Pseudomonas aeruginosa* MPAO1-P2, also referred to as P2.

Still another aspect of the disclosure is a method of reducing the risk of acquiring anastomotic leak comprising administering a therapeutically effective amount of a plasminogen inhibitor, wherein the plasminogen inhibitor is any one of the plasminogen inhibitors identified in the preceding paragraph. In some embodiments of this method, the plasminogen inhibitor is tranexamic acid, F-aminocaproic acid, plasminogen activator inhibitor-1, plasminogen activator inhibitor-2, plasminogen activator inhibitor-3, or antiplasmin. In some embodiments, the antiplasmin is alpha-2-antiplasmin. In some embodiments, the plasminogen inhibitor is tranexamic acid. In some embodiments, the method of reducing the risk of acquiring anastomotic leak further comprises the administration of a therapeutically effective amount of a phosphate-loaded polymer. In some embodiments, the phosphate-loaded polymer is a phosphorylated polyethylene glycol. In some embodiments, the phosphorylated polyethylene glycol is ABA-PEG20k-Pi20. In some embodiments, the risk of acquiring anastomotic leak is associated with collagenolytic *Enterococcus faecalis*. In some embodiments, the risk of acquiring anastomotic leak is associated with *Pseudomonas aeruginosa*, e.g., *Pseudomonas aeruginosa* MPAO1-P2.

Yet another aspect of the disclosure is a method of treating anastomotic leak comprising administering the composition described herein. Another aspect is drawn to a method of reducing the risk of acquiring anastomotic leak comprising administering the composition described herein. In addition, the disclosure provides another aspect drawn to a method of reducing the risk of acquiring a microbe-mediated disorder comprising administering the composition described herein.

Another aspect of the disclosure is a triblock copolymer comprising: (a) a hydrophobic core; and (b) at least two polyethylene glycol chains wherein at least one polyethylene glycol chain is a phosphorylated polyethylene glycol comprising more than two phosphate groups. In some embodiments, at least two polyethylene glycol chains are phosphorylated polyethylene glycol chains comprising more than two phosphate groups. In some embodiments, the hydrophobic core is a carbocyclic or heterocyclic ring, including embodiments wherein the ring is aromatic, such as a single ring or a plurality of rings. In some embodiments, the hydrophobic core is a diphenylmethyl moiety. In some embodiments, the hydrophobic core is a 4,4'-(propane-2,2-diyl)diphenolate salt. In some embodiments, the copolymer has a molecular weight of at least 8,000 daltons, at least 12,000 daltons, at least 15,000 daltons, at least 16,000 daltons, at least 17,000 daltons, at least 18,000 daltons, at least 19,000 daltons, at least 20,000 daltons, or is between 15,000-20,000 daltons. In some embodiments, the copolymer is in solution. In some embodiments, the dispersity (Ð) of the triblock copolymer disclosed herein is less than or equal to 1.10. In some embodiments, the triblock copolymer is a phosphorylated form of ABA-PEG-PGly or ABA-PEG-PEEGE.

Another aspect of the disclosure is directed to a method of producing the triblock copolymer comprising (a) covalently attaching at least two polyethylene glycol chains to a hydrophobic core comprising a carbocyclic or heterocyclic ring; and (b) covalently attaching at least two phosphate groups to at least one polyethylene glycol chain. In some embodiments, at least two polyethylene glycol chains are each covalently attached to at least two phosphate groups.

Yet another aspect of the disclosure is a method of treating anastomosis comprising administering a therapeutically effective amount of a composition comprising a triblock copolymer disclosed herein to a subject in need. In some embodiments, the triblock copolymer has a molecular weight of at least 8,000 daltons, 12,000 daltons, 15,000 daltons, 16,000 daltons, 17,000 daltons, 18,000 daltons, 19,000 daltons, 20,000 daltons, or between 15,000-20,000 daltons.

Still another aspect of the disclosure is a method of treating anastomotic leakage comprising administering a therapeutically effective amount of a composition comprising a triblock copolymer disclosed herein to a subject in need. In some embodiments, the triblock copolymer has a molecular weight of at least 8,000 daltons, 12,000 daltons, 15,000 daltons, 16,000 daltons, 17,000 daltons, 18,000 daltons, 19,000 daltons, 20,000 daltons, or between 15,000-20,000 daltons.

In another aspect, the disclosure provides a method of preventing anastomotic leakage comprising administering an effective amount of a composition comprising a triblock copolymer disclosed herein to a subject at risk of anastomotic leakage. In some embodiments, the triblock copolymer has a molecular weight of at least 8,000 daltons, 12,000 daltons, 15,000 daltons, 16,000 daltons, 17,000 daltons, 18,000 daltons, 19,000 daltons, 20,000 daltons, or between 15,000-20,000 daltons.

Yet another aspect of the disclosure is directed to a method of suppressing anastomotic leakage comprising administering an effective amount of a composition comprising a triblock copolymer disclosed herein to a subject at risk of anastomotic leakage. In some embodiments, the triblock copolymer has a molecular weight of at least 8,000 daltons, 12,000 daltons, 15,000 daltons, 16,000 daltons, 17,000 daltons, 18,000 daltons, 19,000 daltons, 20,000 daltons, or between 15,000-20,000 daltons.

Other features and advantages of the disclosure will become apparent from the following detailed description, including the drawing. It should be understood, however, that the detailed description and the specific examples, while indicating embodiments, are provided for illustration only, because various changes and modifications within the spirit and scope of the disclosure will become apparent to those skilled in the art from the detailed description.

DETAILED DESCRIPTION

Figure 1:
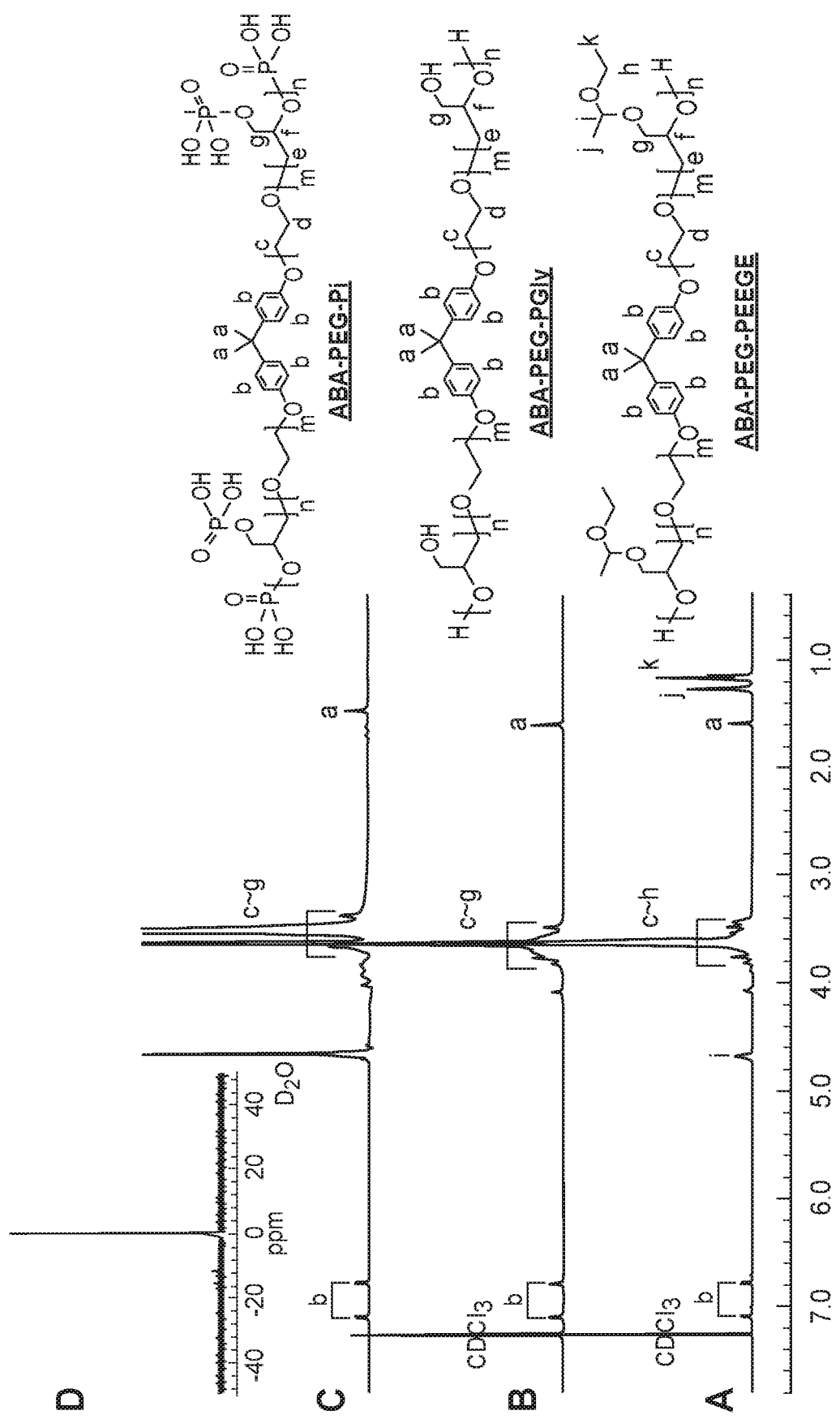
FIG. 1. $^1$H-NMR spectra of (A) ABA-PEG20k-E18, (B) ABA-PEG20k-G20, (C) ABA-PEG20k-Pi20, (D) $^{31}$P-NMR spectrum of ABA-PEG20k-Pi2O, and (E) Titration curve of ABA-PEG20k-Pi20 with NaOH solution. 20k is the designed molecular weight of PEG block; E18 means the designed repeating units of EEGE block is 18; G20 means the designed repeating units of Glycerol is 20. Pi20 means the designed repeating units of phosphorylated Glycerol block is 20.
Figure 1:
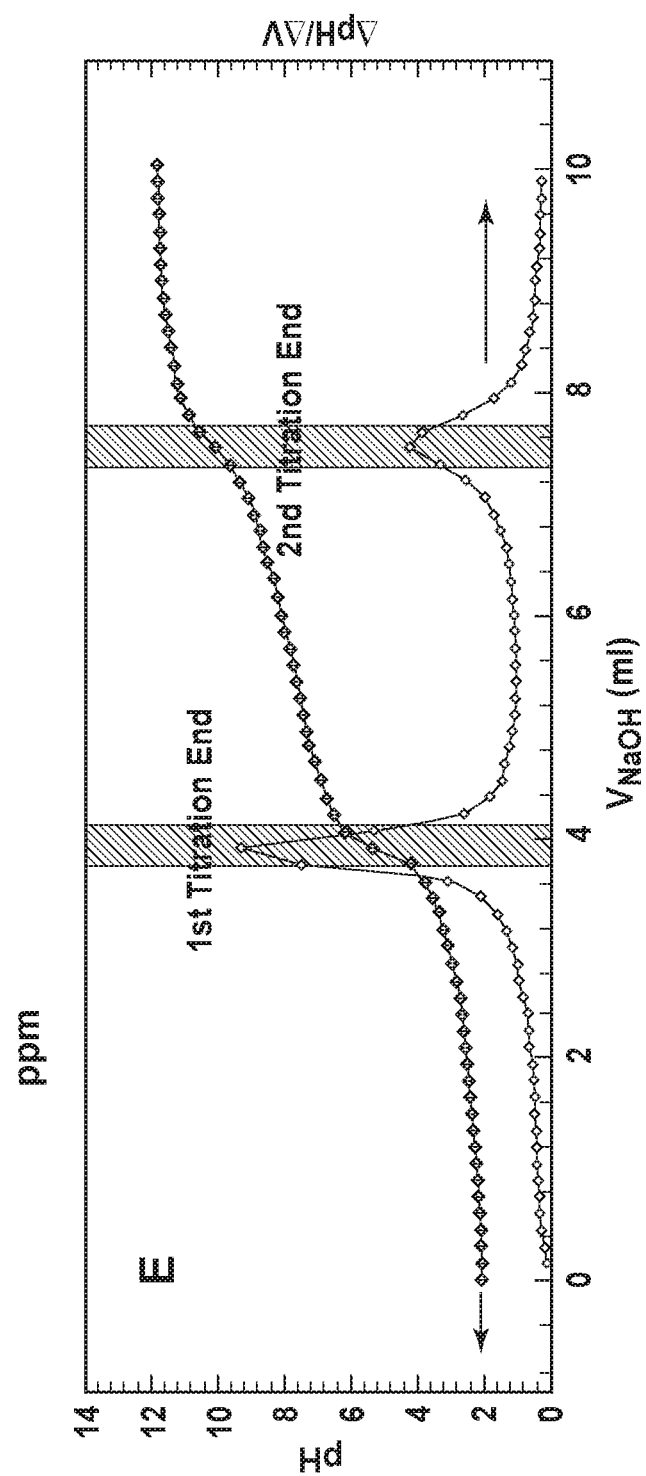

The disclosure provides insight into the molecular pathogenesis of anastomotic leak (AL) by focusing on the microbiome and host interactome local to the healing anastomosis [33, 34]. The inventors have demonstrated that low abundance commensal and pathogenic microbes can "bloom" under surgical conditions, colonize anastomotic tissues and express invasive and tissue destructive phenotypes. Many of the pathogens the inventors have identified, such as Pseudomonas aeruginosa and Enterococcus faecalis, escape elimination by IV and oral antibiotics regardless of susceptibility patterns. Such pathogenic, or opportunistically pathogenic, bacteria utilize host proteases and inflammatory factors to degrade essential submucosal collagen at the anastomotic site [35, 36]. This infection-inflammation paradigm is a unique model for pathogenesis of AL. Disclosed herein is data demonstrating that pathogens that cause AL in mice and humans, such as Enterococcus faecalis, display increased collagen degradation in vitro. However, the precise mechanisms of in vivo collagenolysis leading to AL, those that will inform targetable pathways of prevention, remain unclear. The disclosure elucidates the molecular underpinnings of pathogen-mediated AL to provide compositions and methods to reduce the risk of leaks using small molecule inhibitors currently in clinical use. Based on compelling data and the known critical role of the fibrinolytic protease plasminogen (PLG) in wound healing, the experiments disclosed herein establish that PLG plays a key and previously unappreciated role in the molecular pathogenesis of AL. PLG is a known activator of the MMP system and is itself activated by MMP9. Pathogenic bacteria have long been known to manipulate the PLG regulatory system through over-activation, shifting physiologic healing into a pathoadaptive healing process [37, 38]. Recently, dysregulation of PLG activation has been demonstrated to cause impaired tissue repair following injury in murine models that correlates to clinical observations in human disease [39, 40]. In addition, genetic ablation of an endogenous host inhibitor of PLG resulted in dysregulated collagen remodeling in anastomotic tissues similar to results observed in the pathogen-induced AL model [41]. However, net bacterial activation of PLG secondary to surgically induced changes in the local microbiome has not been studied. The central role of PLG in wound healing and its ability to be pharmacologically manipulated with safe and inexpensive drugs make it a highly attractive target for intervention. The oral PLG inhibitor tranexamic acid (TXA) has been proven safe in elective orthopedic surgery for reduction of blood loss, without increased risk of thrombotic complications. Disclosed herein is a new mechanism of action for TXA delivered to the gut—its ability to attenuate E. faecalis-induced collagen degradation and prevent AL.

This disclosure reveals the molecular modeling of the pathogenesis of AL. By incorporating a specific bacterial phenotype that commonly colonizes anastomotic tissues at the intersection of two important tissue proteases, PLG and MMP9 (which are central mediators of collagenolytic in wounded tissues), the disclosure provides materials and methods useful in treating or reducing the risk of developing a microbe-mediated disorder exemplified by AL.

The disclosure also provides a phosphorylated polyethylene glycol compound that was developed to allow phosphate to be distributed along the entire gut and into the distal intestine where microbes such as bacteria are most abundant. The phosphorylated polyethylene glycol compounds of the disclosure have a triblock copolymer structure of ABA, with "A" referring to any polyethylene glycol, or derivative thereof, that is at least 8,000 daltons, 12,000 daltons, 15,000 daltons, 16,000 daltons, 20,000 daltons, or is between 15,000-20,000 daltons. The "B" component of the triblock structure is a hydrophobic compound capable of covalent linkage to two PEG molecules of the disclosure, or derivatives thereof. Exemplary hydrophobic cores are bisphenol A (BPA) and bisphenol E (BPE).

In discussing the compounds of the disclosure, and compositions comprising such compounds, the following terminology is used. "ABA" refers to the triblock structural organization of the compounds, with two like polymers, e.g., PEG, bracketing a "B" structure that is a hydrophobic core such as any aliphatic, carbocyclic, heterocyclic, or aromatic structure that is hydrophobic, e.g., any of the bisphenols. "PEG" refers to polyethylene glycol, and "Pi-PEG" refers to a phosphorylated polyethylene glycol. "EEGE" is ethoxyethyl glycidyl ether and "PEEGE" is polyethoxyethyl glycidyl ether. As described below, EEGE is de-protected and, once de-protected, EEGE groups become hydroxy groups and the structure is referred to as a polyglycidol, such as ABA-PEG-PGly. Compounds identified as ABA-E8-PEG10k, ABA-E12-PEG16k, and ABA-E18-PEG20k refer to triblock copolymers having the ABA structure with 8 EEGE groups (E8) and PEG groups of 10k in ABA-E8-PEG8k. For ABA-E12-PEG16k, the compound has the ABA structure with 12 EEGE groups (E12) and PEG groups of 16k. In like manner, ABA-E18-PEG20k has an ABA structure with 18 EEGE groups and PEG groups of 20k. For compounds identified as ABA-G10-PEG10k, ABA-G14-PEG16k and ABA-G20-PEG20k, "G10" refers to 10 hydroxyl groups created by de-protection of EEGE (the "G" is a reference to the compound as a polyglycidol), while "G14" and "G20" refer to 14 and 20 hydroxyl groups, respectively. Compounds defined as ABA-Pi10-PEG10k, ABA-Pi14-PEG16k, and ABA-Pi20-PEG20k refer to compounds having the ABA triblock copolymer structure with 10, 14, or 20 phosphoryl groups (e.g., phosphate groups), respectively, resulting from phosphorylation of a polyglycidol. Consistent with the naming convention explained above, PEG10k, PEG16k, and PEG20k refer to PEG groups of 10k, 16k and 20k, respectively. It is apparent that the number of functional groups (e.g., EEGE) ultimately rendered amenable to phosphorylation can vary in the compounds according to the disclosure, and the size of PEG molecules bearing those functional groups can vary, including PEG molecules in a compound totaling at least 8,000 daltons, at least 12,000 daltons, at least 15,000 daltons, at least 16,000 daltons, at least 20,000 daltons or between 15,000-20,000 daltons.

The phosphate content of compounds delivered to the intestine is particularly important for any protective effect, given that local phosphate concentrations are known to support bacterial growth while at the same time suppress bacterial virulence[3]. The mechanism underlying this effect involves phosphosensory/phosphoregulatory circuits that are a universal feature of most bacteria and play a key role in virulence[5].

Figure 7:
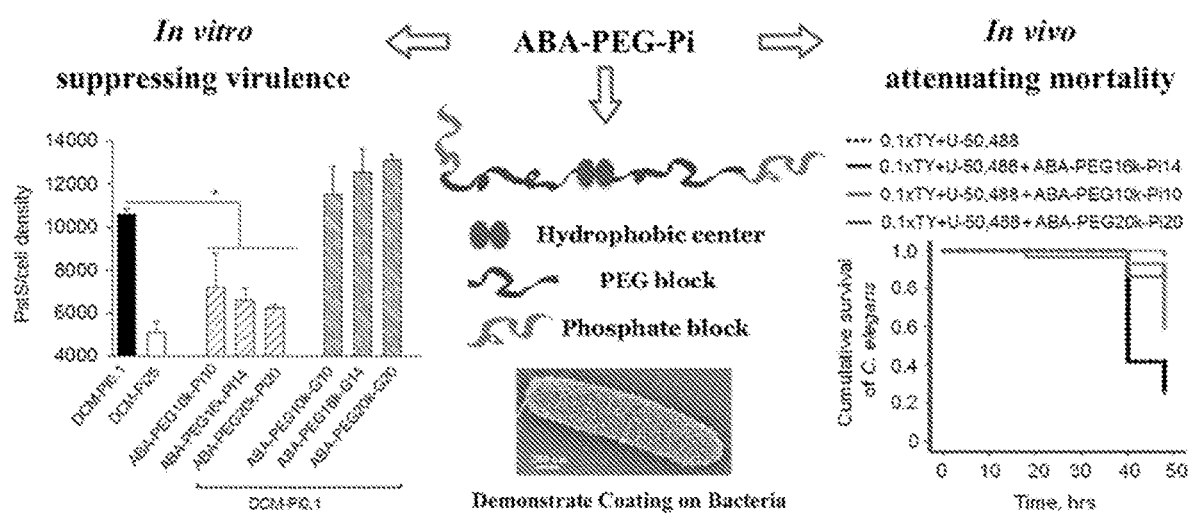
FIG. 7. Schematic illustration of ABA-PEG-Pi block co-polymer and its function suppressing virulence of pathogenic microbes in vitro and attenuation of mortality in vivo, as well as its capacity to coat the surface of bacteria.

Analysis of PEG15-20 (Sigma) showed that it was not a pure tri-block polymer but rather a mixture of polymers of varying molecular weights including ABA triblock, AB diblock and homopolymer poly(ethylene glycol) structures (FIG. 7). In contrast to these impure mixtures of polymers of differing molecular weights, disclosed herein is the de novo synthesis of polymers with a well-defined ABA structure, the phosphorylation of which yielded compounds with a defined number of phosphorus atoms (phosphate groups). Results demonstrated highly effective anti-virulence properties of the synthesized phosphorylated polymers with defined ABA structure and phosphate content against the model opportunistic pathogen Pseudomonas aeruginosa.

Figure 40:
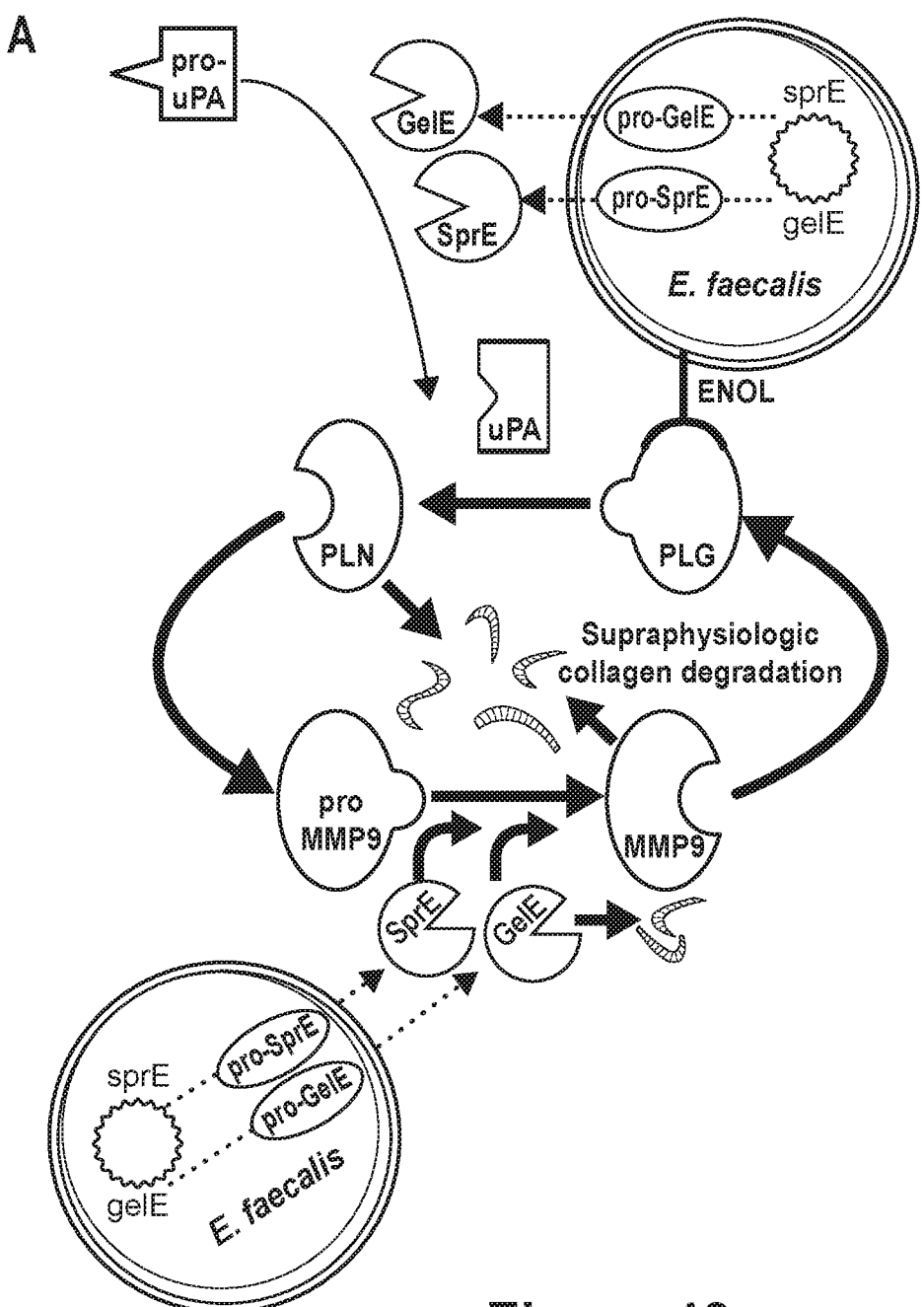
FIG. 40. Molecular paradigm of pathogen-mediated anastomotic leak pathogenesis and pharmacologic rescue with TXA. A) Pathogens are a disordering agent to a cycle of protease activation normally regulated in a highly defined temporospatial context. B) TXA applied locally at the anastomotic site temporarily and partially inhibits plasmin activation, attenuating the loop of excessive PLG activation while allowing direct MMP activation and anastomotic healing to occur. Abbreviations: PLG: plasminogen; PLN: active plasmin uPA: urokinase-type plasminogen activator; ENOL: alpha-enolase; PLGR: Plasminogen receptor; TXA; tranexamic acid; GelE: gelatinase E; and SprE: serine protease.
Figure 40:
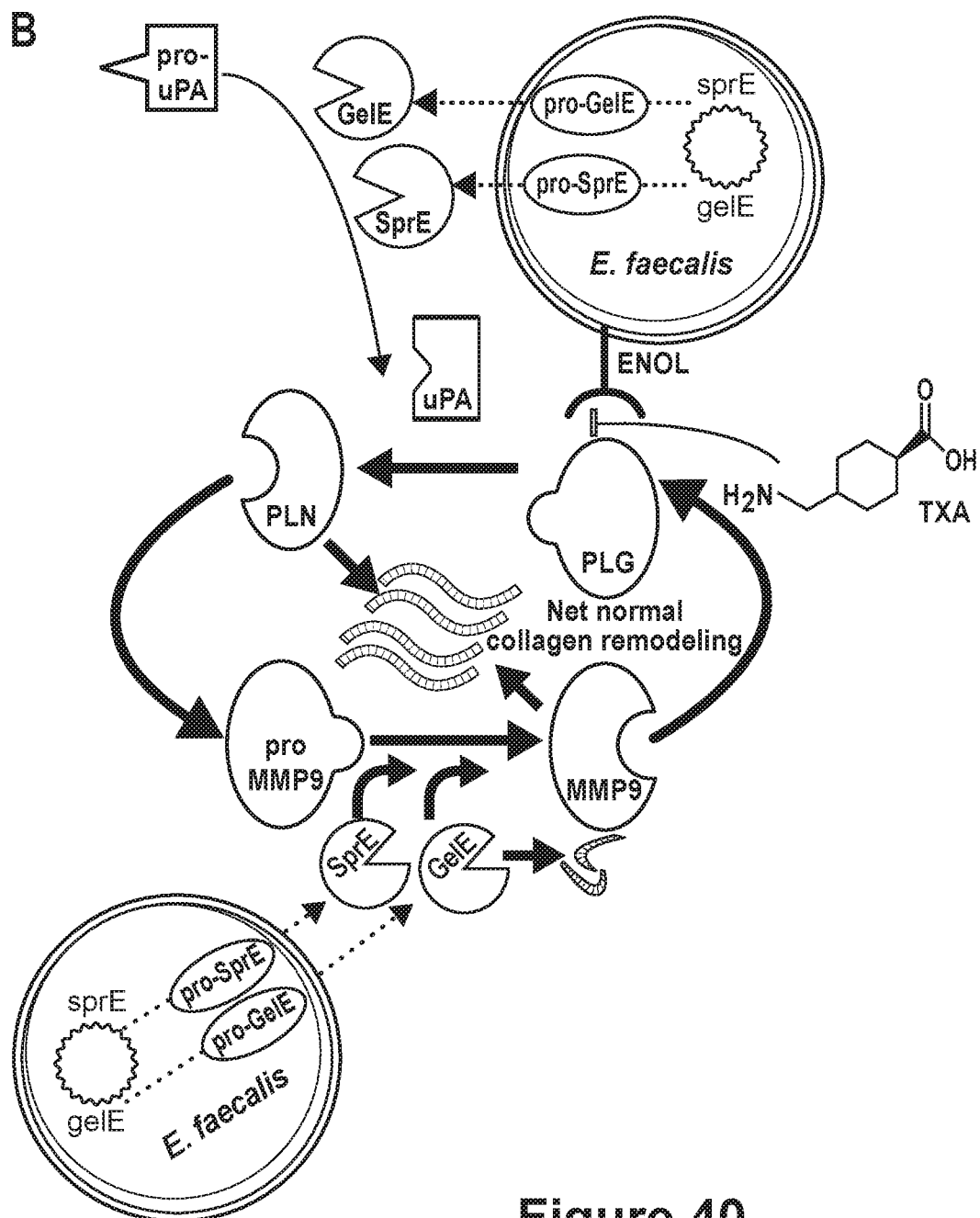

More generally, across all wounds, protease activity represents the hallmark of healing as an important balance between collagen synthesis and breakdown, remodeling, strength and integrity of an injured or operated tissue. Because bacteria can disorder the process of healing, sterility is maintained during surgery with the goal of preventing complications. A wound in the gastrointestinal tract, particularly in the colon, represents a unique challenge, given the high density of pathogenic bacteria present before, during and after anastomotic surgery (32', 34'). The current practice of intestinal antisepsis prior to colon surgery involves administration of both oral and intravenous antibiotics, targeting both the abundant health-promoting microbiota and the low-abundance pathobiota (35'). This approach, the formulation of which has not significantly changed since its inception over 50 years ago, remains controversial, highly debated, and poorly understood in terms of its precise mechanisms of action (36'-38'). Indiscriminate elimination of the normal microbiota carries the unintended consequence of allowing resilient pathobiota to bloom and may account for the persistence of the incidence of AL following major surgery (32', 39'). The most common bacteria cultured from an AL are E. faecalis and P. aeruginosa, pathobionts that persist in the gastrointestinal tract even when powerful antibiotics are used (40'). The inventors provide compelling evidence that collagenase-producing pathogens, including but not limited to E. faecalis, P. aeruginosa, and S. marcescens, play a causal role in AL in rodents via their ability to activate host proteases such as MMP9 in addition to their direct effect on wound collagen breakdown (8', 10'). Data disclosed herein identify an additional and complementary mechanism by which collagenolytic bacteria contribute to the pathogenesis of AL, i.e., the PLG system, known to be present in all healing wounds, although poorly described in intestinal wounds. Elucidation of the contributory role of the PLG system in the experimental work disclosed herein demonstrates that it is highly integrated in the bacterial-mediated MMP9 activation process (FIG. 40). Importantly, identification of a bacterial-MMP9-PLG integrated process in the pathobiology of AL that can be effectively dampened by TXA provides an exciting opportunity to prevent AL in response to multiple collagenolytic pathogens. The fact that AL persists even in the face of current best practices reveals a pressing need to develop alternative approaches to this devastating, disabling and occasionally lethal complication of anastomotic surgery. Use of TXA in combination with collagenase-suppressing agents such as phosphate-active compounds (e.g., phosphorylated polyethylene glycol), are expected to decrease the incidence of AL and halt the practice of adding multiple antibiotics, which is not an evolutionarily stable strategy.

Among pathogens demonstrated to play a causative role in AL, *E. faecalis* has not been previously described as activating the PLG system. In vitro work disclosed herein details PLG activation by *E. faecalis* that follows a familiar mechanistic schema: cell-surface binding of PLG and activation of its activator uPA (24', 42'). The data is consistent with surface-expressed alpha-enolase being one of multiple PLG receptors on *E. faecalis*. The process depends on *E. faecalis* virulence factors GelE and SprE, which are up-regulated in wounded host environments. Their genetic elimination prevented AL in a rat model of *E. faecalis*-induced AL (10', 43'). In the experiments disclosed herein, pharmacologic targeting of this process with TXA successfully targeted and prevented AL, as might be clinically manifested in a patient (e.g., abscess formation or peritonitis). The additional finding that phosphate exposure decreased PLG activation by *P. aeruginosa* and rescued AL induced by that same strain establishes that supraphysiologic PLG activation is central to pathogen-mediated AL.

Given that multiple pathogens express collagenolytic enzymes that can potentially disrupt anastomotic healing, targeting PLG activation with TXA and phosphates is expected to be a broadly applicable method to prevent AL across a wide spectrum of pathogens and regions of the gastrointestinal tract. Local administration of TXA by enema will likely decrease the risk of thrombotic complications observed in clinical studies of systemic administration for prevention of blood loss (44'). Administration of high-dose TXA via the transrectal route appeared to be both safe and efficacious. Its bioavailability through the colon and rectum is roughly 15% of the same dose given orally, even in patients with active colonic inflammation (45'). Yet another advantage of local TXA application is its temporal effect. PLG inhibition with alternative agents, such as α2-antiplasmin or PAI-1, is feasible. These agents, however, induce non-reversible inhibition of plasmin and uPA, respectively, requiring de novo production of the proteases for the recovery of normal activity, whereas TXA temporarily prevents PLG binding and its effect ends after clearance from the surgical site in a matter of hours (46', 47'). The disclosure establishes TXA enema as a bridge therapy during the post-operative recovery of the normal microbiome to prevent pathogen-mediated AL in humans at a low cost and with administration of a FDA-approved agent.

The disclosure will be more fully understood by reference to the following examples, which detail exemplary embodiments of the disclosure. The examples should not, however, be construed as limiting the scope of the disclosure.

EXAMPLES

Example 1

Materials. Bisphenol A (BPA, >99%, Aldrich), naphthalene (99%, Aldrich), diphenylmethane (99%, Aldrich), and phosphorus oxychloride ($POCl_3$, 99%, Aldrich) were used as received. Ethylene oxide (EO, >99%, lecture bottle, Praxair) and Ethoxyethyl glycidyl ether (EEGE, 97%, Synthonix) were treated with di-n-butylmagnesium for 20 min, and distilled into schlenk flasks before use. Tetrahydrofuran (THF, HPLC, inhibitor free, Aldrich) was purified with a solvent purification system (Mbraun SPS-800) and distilled from a sodium naphthalenide solution directly before use. Diphenylmethylpotassium (DPMK) was prepared as described. Initially, a potassium naphthalenide solution was prepared in dry THF with 1:4 mole ratio of naphthalene to potassium. After stirring for 12 hours, 0.66 molar equivalent of diphenylmethane was introduced to the solution via a syringe and the solution was allowed to stir at room temperature for at least 12 h prior to use.

Synthesis of phosphorylated PEG-based block copolymers with a hydrophobic core. Sequential anionic polymerization of ABA-PEG-PEEGE. A series of ABA-PEG-PEEGE were synthesized by the sequential anionic polymerization of EO and EEGE in a custom heavy-wall glass reaction flask on schlenk line. In a typical reaction, BPA (251 mg, 1.1 mmol) dissolved in 120 mL anhydrous THF at 0° C. under dry nitrogen atmosphere, titrated with DPMK to form the initiator, followed by addition of the first monomer EO (22.0 g, 500 mmol). After stirring for 1 h, the mixture was heated to 50° C. and reacted for 3 days to attain complete conversion of EO monomer. Then the second monomer EEGE (2.9 g, 19.8 mmol) was injected into the flask and allowed to react for another 3 days. The polymerization was terminated with methanol and the polymer was recovered by precipitation in cold diethyl ether. Different chain length of EO and EEGE can be adjusted by the feed ratio of [EO]/[Initiator] and [EEGE]/[Initiator].

Hydrolysis of ABA-PEG-PEEGE. Hydrolysis of EEGE segments of block copolymer was carried out in THF with 4 wt % of HCl and stirred at room temperature for 30 min. The polymers were then purified by precipitating in cold hexane and finally dried under vacuum at 60° C. to get a yellowy wax-like product ABA-PEG-PGly (PGly: Poly glycerol). The disappearance of peaks at 4.70 ppm (q, 1H), 1.29 ppm (d, 3H), 1.19 ppm (t, 3H) in $^1$H-NMR confirmed the success of de-protection.

Phosphorylation of ABA-PEG-PGly. ABA-PEG-Pis (Pi: Poly phosphoric acid) were prepared by phosphorylation of ABA-PEG-PGly, which was performed in a flame-dried flask under dry nitrogen atmosphere. ABA-PEG-PGly dissolved in anhydrous THF at 50° C., a ten-fold equivalent molar amount of $POCl_3$ was added at once via gas-tight syringe. The solution was stirred under nitrogen pressure for 3 h, quenched by the addition of small amount of water. After evaporation of THF and dialysis against Milli-Q water, the sample was lyophilized to give a white flocculent product. $^{31}$P-NMR ($D_2O$): δ=−0.18 ppm.

Synthesis of phosphorylated PEG-based block copolymers without a hydrophobic core (PEG-Pi). The synthetic strategy of PEG-Pi is quite similar to that of ABA-PEG-Pi, with the exception that the polymerization started with hydrophilic ethylene glycol instead of hydrophobic BPA, as shown in Scheme 2. First, PEG-PEEGE was prepared by starting with ethylene glycol. Next, polymerizing through the sequential adding of EO and EEGE and then using the same hydrolysis (to get PEG-PGly) and phosphorylation process, PEG-Pi was obtained.

Characterization of block copolymers. $^1$H and $^{31}$P-NMR spectra were obtained at a Bruker Ultrashield Plus 500 MHz spectrometer and referenced internally to solvent proton signal. Apparent molecular weights and dispersity (Đ) were characterized with a gel permeation chromatography (GPC) system equipped with a Waters 1515 pump, a Wyatt Optilab T-rEX differential refractive index (RI) detector, and a Waters 2998 photodiode array (PDA) detector. For ABA-PEG-PEEGEs, ABA-PEG-PGlys, PEG-PEEGEs and PEG-PGlys, THF was used as elution at 35° C. with an elution rate of 0.8 ml/min. Three Waters Styragel columns were used and calibrated by polystyrene standards (Aldrich). While ABA-PEG-Pis and PEG-Pis were measured in 0.1 M NaNO$_3$ (aq) at 25° C. with an elution rate of 1.0 ml/min on the same setup, except three Waters Ultrahydrogel columns in series were used and calibrated by PEO standards (Aldrich).

Biological tests. Bacterial strains. *Pseudomonas aeruginosa* strains MPAO1-P1 and MPAO1-P2 [16] were used in all experiments. The MPAO1-P1 strain and its derivative mutant ΔPvdD were used to create the reporter constructs, MPAO1-P1/pstS-EGFP and ΔPvdD/pstS-EGFP.

Construction of pSensor-PstS-EGFP. The promoter region of pstS gene (*P. aeruginosa* MPAO1) was cloned in a pSensor vector created in the laboratory. The pSensor consists of a pUCP24 vector backbone and Gateway C.1 cassette (Invitrogen) in frame with EGFP reporter gene (derived from pBI-EGFP) cloned into Sma1 and Pst1/Hind III sites of pUCP24 MCS region respectively. The region upstream of pstS was amplified by PCR (Platinum PCR SuperMix (Invitrogen) using primers PstS_F: CACCTATCCCAAAACCCCTGGTCA (SEQ ID NO:1) and PstS_R: CAAACGCTTGAGTTTCATGCCTTG (SEQ ID NO:2), and cloned into the Gateway entry vector (pCR8/GW/Topo kit (Invitrogen)). Nucleotide sequence and orientation of the inserts were confirmed by sequencing, inserts were transferred into pSensor vector via LR reaction using Gateway LR Clonase II Enzyme Mix (Invitrogen). Throughout the study, vector constructs were propagated in One Shot TOP10 Chemically Competent *E. coli* cells. Gentamycin (100 g/ml) selection was used for pUCP24 and pSensor and Ampicillin (100 μg/ml) for pBI-EGFP vectors. The QIAGEN Plasmid Mini Kit (Qiagen) was used for plasmid DNA extraction.

PstS expression. *P. aeruginosa* MPAO1-P1/pstS-EGFP or ΔPvdD/pstS-EGFP were grown on tryptic soy agar plates supplemented with 100 μg/ml gentamicin (Gm100) overnight. Few colonies from the overnight plates were used to inoculate liquid TSB+Gm100 for overnight growth. The overnight culture was used to inoculate fresh TSB+Gm100 at 1:100 dilution and grow to OD$_{600}$ nm=0.5. Cells were pelleted by centrifugation at 3300×g for 5 min, and washed twice with defined citrate media (DCM: sodium citrate, 4.0 g/L (Sigma, S4641), (NH$_4$)$_2$SO$_4$, 1.0 g/L (Sigma, A4915), MgSO$_4$·7H$_2$O, 0.2 g/L (Fisher, M63-50). DCM medium is limited in both phosphate and iron. The inventors used potassium phosphate buffer, pH 6.0 (PPB) for phosphate supplementation. The supplementation of DCM with PPB 0.1 mM was defined for phosphate limitation (DCM-Pi0.1), and with PPB 25 mM for phosphate abundance (DCM-Pi25). Washed cells were resuspended in DCM-Pi0.1+Gm100 or DCM-Pi25+Gm100, respectively, and grown overnight. In experiments carried out to test the phosphorylated polymers, bacterial cells were washed in DCM-Pi0.1 and resuspended in DCM-Pi0.1+Gm100 supplemented with 2 mM ABA-PEG-Pis or ABA-PEG-PGlys and adjusted to pH 6.0 with KOH. After overnight growth, fluorescence (excitation 485/10, emission 528/20) and absorbance (600 nm) were measured with FLx800 fluorescent reader (Biotek Instruments). Fluorescence readings were normalized to absorbance. Culture conditions were: 37° C., shaking at 180 rpm (C25 Incubator Shaker, New Brunswick Scientific, Edison, NJ).

Pyocyanin production during low phosphate conditions. *P. aeruginosa* MPAO1-P2, which is known to produce higher amounts of pyocyanin than MPAO1-P1 [16], was used in this set of experiments. The design of the experiments was similar to the experiments described above for PstS expression except they were performed in the absence of gentamicin in the DCM media. 2 μM Fe$^{3+}$ (1 μM Fe$_2$(SO$_4$)$_3$) was added to the media in order to enhance the production of pyocyanin. Pyocyanin was extracted by chloroform followed by re-extraction in the 0.2N HCl and measured at OD520 nm as previously described [17]. Before extraction, cell density was measured by the absorbance at 600 nm, and pyocyanin values were normalized to bacterial cell density.

Pyocyanin production following exposure virulence activating factor U-50,488, kappa opioids agonist. The inventors have previously demonstrated that *P. aeruginosa* can be triggered to express enhanced virulence when exposed to kappa opioids, host factors known to be released into the gut during physiologic stress [17]. *P. aeruginosa* MPAO1-P1 which is highly sensitive to U-50,488 was used in these experiments. MPAO1-P1 was grown on tryptic soy agar plates overnight, and a few colonies were used to inoculate liquid TSB for overnight growth. Overnight cultures were used to inoculate fresh TSB at 1:100 dilution followed by the growth for 1 hour. Next, 200 μM U-50,488 (Sigma) was added, and growth continued for 10 hrs. Pyocyanin was extracted and measured as described above.

*Caenorhabditis elegans* killing assays. *C. elegans* N2 nematodes provided by the *Caenorhabditis* Genetic Center (CGC), University of Minnesota, were used in these experiments. Synchronization and pre-fasting of worms was performed by transferring them onto plain plates with kanamycin as previously described [3]. *P. aeruginosa* MPAO1-P1 was grown overnight in tryptone/yeast extract medium (TY, tryptone, 10 g/L; yeast extract, 5 g/L) and diluted at 1:100 in 0.1× TY (TY diluted 10-fold with water). Potassium phosphate buffer, pH 6.0, was included in the 0.1× TY to a final concentration of 0.1 mM. After 1 hour of growth, the kappa-opioid receptor agonist U-50,488 was added to a final concentration of 50 μM followed by 2 hours growth as previously described [18, 19]. 2 ml of the microbial culture was adjusted to room temperature and poured in the 30-mm-diameter dishes into which pre-fasting nematodes (10 nematodes per plate) were transferred. *P. aeruginosa* grown overnight in TY was diluted at 1:100 in either 0.1× TY or 0.1×TY containing polymers at 2 mM or (5% in selected experiments as indicated) final concentrations and adjusted to pH 5.2 with KOH. Plates were incubated at RT, without shaking, and mortality was defined if worms did not respond to the touch of a platinum picker.

Statistical analyses. All data are from 3 or more replicates and presented as the mean with standard deviation presented as error bars. Statistical analysis was performed using SigmaPlot software. In *C. elegans* experiments, Long-rank (Mantiel-Cox) test (GraphPad Prizm 7) was used with significance accepted as a p-value <0.05. In in vitro experiments, Student t-tests were used with and significance determined to be p-value <0.05.

Scanning electron microscopy (SEM). *P. aeruginosa* MPAO1 was grown in tryptic soy broth (TSB) overnight. Overnight cultures (2 ml) were centrifuged at 6,000 rpm, 5 min, RT, and pellets were gently (3 times) washed with DCM-Pi0.1 (see section PstS expression). Washed pellets were suspended in 1 ml of DCM-Pi0.1 or 2 mM ABA-PEG20k-Pi2O or 2 mM PEG20k-Pi2O. ABA-PEG20k-Pi2O and PEG20k-Pi2O solutions were prepared in DCM-Pi0.1 and pH was adjusted by KOH to DCM-Pi0.1. Bacteria were grown for 4 hours, then cells were pelleted by centrifugation at 6,000 rpm, 5 min, RT, and gently (3 times) washed with phosphate buffered saline (PBS). Bacterial cells were then dropped onto glass coverslips coated with poly-L-lysine. Cells were fixed in 3% glutaraldehyde buffered with 0.1 M phosphate buffer, pH 7.2, washed with 0.1 M phosphate buffer, and dehydrated in a graded ethanol solution in water (30% increased gradually to 100%; 20 min each). The samples were dried with a Leica CPD300 critical point dryer and coated with Pt(80)/Pd(20) of an 2 nm thickness by using a Cressington sputter coater, model 208HR. SEM images were obtained using a Zeiss Merlin FE-SEM with an accelerating voltage of 1 kV and a working distance of 3 mm.

Methods applied with particularity to experiments disclosed in Examples 10-20. The remaining methods described in this Example were applied with particularity to the experiments disclosed in Examples 10-19. Experiments were designed to investigate a pathobiologic mechanism for pathogen-mediated AL. The approach taken was to 1) mechanistically describe activation of the PLG system by *E. faecalis*, an organism with a known causal role in AL, 2) evaluate the impact of bacterial PLG activation on collagen degradation, the common final pathway of AL, 3) test the ability of TXA to inhibit bacterial PLG activation and collagen, 4) illustrate PLG deposition at the site of anastomotic surgery, and 5) assess the impact of locally applied TXA on PLG binding and anastomotic healing.

Bacterial strains. All investigations of *E. faecalis* utilized the commercially available strain V583 (ATCC 700802) or E44 strain unless otherwise noted. Derivative mutants of V583 (ΔgelE, ΔsprE, ΔΔgelEsprE) and complemented mutants (ΔgelE/gelE, ΔsprE/sprE, ΔΔgelEsprE/gelEsprE) were prepared using recombinant DNA technologies known in the art (48'). *P. aeruginosa* MPAO1-P2 was isolated from the colon of a rat that had undergone a separate model of pathogen-mediated anastomotic leak (8', 49'). All strains were stored in 10% glycerol stock at −80° C. Only cells freshly plated from stock were used in experiments. Cells from stock were plated onto tryptic soy broth plates, grown overnight at 37° C. and transferred to liquid tryptone yeast (TY) media. To create conditioned media (CM), bacteria were grown overnight in TY, diluted to $OD_{600}$ 0.1, centrifuged at 5000 rpm for 10 minutes sufficient to pellet bacterial cells and debris, and sterilized through a 0.2 micron filter.

Plasminogen/uPA activity. Plasmin activity assays were performed as previously described with minor modifications, and fluorescence data was analyzed per the manufacturer's instructions (50'). Incubation times were optimized for bacteria at low optical density to limit internal filter effects in fluorescence-based assays. Bacteria (when included) were grown overnight in TY media. $OD_{600}$ was normalized by dilution to 0.1, equivalent to $8 \times 10^7$ CFU/mL. Samples at OD 0.1 were diluted 1:10 in the final reaction through the addition of media and dissolved substrates. Bacteria were incubated with 250 nM human glu-plasminogen (Haematologic technologies) for two hours at 37° C. TXA (Fisher) was added concomitantly with PLG. A final concentration of 4 nM uPA (Biovision) or pro-uPA (Biovision) was added and incubation proceeded for 20 minutes. A final concentration of 6 M fluorogenic substrate specific for plasmin (H-D-Val-Leu-Lys-AFC, AnaSpec) was added immediately prior to a kinetic fluorescent read with excitation wavelength 380 nm and emission wavelength 500 nm. Reads were conducted every 15 to 30 seconds over the course of 30 minutes. For assays of uPA activity, PLG was omitted from the incubation and a substrate specific to uPA (Z-Gly-Gly-Arg-AMC, Bachem) was used. When assays were performed in human plasma, fluorescence was read for 120 minutes total.

Plasmin or uPA activity is expressed as initial reaction velocity calculated from change in fluorescence over time during the initial phase of the reaction, when pseudo-first order kinetics determine the rate due to high substrate concentrations where a linear rise in fluorescence is observed. Linear regression analysis was applied to raw fluorescence data over the initial ten minutes of the reaction in purified systems or over the linear portion of the 120-minute plasma-based assay, with the slope of the regression line indicating initial reaction velocity. Linear regression lines with a goodness of fit ($r^2$) less than 0.8 were excluded and repeated; however, this occurred only once. In plasmin activity assays involving live cells, fluorescence was measured in control wells containing all materials besides cells and subtracted as background. All experiments were run in triplicate on a 96-well plate with 200 L final reaction volume.

Collagen degradation. Assays were performed per the manufacturer's instructions as previously described with slight modifications (51'). Bacteria were grown overnight in TY. Optical density was normalized to 0.1 through dilution. Bacteria were then incubated with fluorescein-labeled type I collagen, type IV collagen, or gelatin according to the manufacturer's instructions (ThermoFisher), human PLG at 250 nM and TXA. Total reaction volume was 200 L. The incubation proceeded at 37° C. for 5 hours to allow for bacterial attachment to collagen and PLG binding. uPA was added and the incubation proceeded for an additional hour. Change in fluorescence over time at 480/520 nm was determined kinetically over the initial 30 minutes of the reaction.

Flow cytometric evaluation of PLG binding. PLG binding to the bacterial surface was measured as previously described, with minor modifications (52'). Bacteria were grown overnight in TY. Cultures were diluted to a final density of roughly $8 \times 10^6$ CFU/mL. These cells were incubated at 37° C. with 250 nM FITC-labeled PLG (Oxford Biomedical Research) with or without TXA. Cells were pelleted, washed three times with PBS, and resuspended. Fluorescence was analyzed using an Imagestream ISX flow cytometer. Enterococci were detected using log-forward and log-side scatter dot plots, and a gating region was set to exclude debris and aggregates of bacteria. Bacteria were analyzed for FITC-range fluorescence using log-scale amplification, of which the geometric mean fluorescence intensity was recorded as a measure for PLG binding. FITC-range fluorescent signal was confirmed by light and fluorescent microscopy of each event.

Antibodies. Polyclonal anti-human enolase IgG raised in rabbits was purchased from Sigma Aldrich. Custom polyclonal anti-enterococcal enolase IgG raised in rabbits was purchased from Genscript. These antibodies were raised against a peptide corresponding to a 16-amino-acid sequence (CAEYKGLKSFYNLKNK; SEQ ID NO:3) at the C-terminus of V583 enolase, including a poly-lysine motif suspected to be the PLG binding site. Nonspecific rabbit IgG isotype control was purchased from EMD-Millipore. Antibodies were diluted to $1 \times 10^{-5}$ mg/mL for blocking assays.

Cell culture. RAW 264.7 or J774 murine macrophages were incubated at 37° C. and 5% $CO_2$ in Dulbecco's modified eagle media (DMEM) with 10% fetal bovine serum, penicillin/streptomycin and antifungals during growth. For plasmin activity assays, cells were plated at $10^4$ cells/well on a 96-well plate in phenol-free DMEM with 1% FBS. Added bacteria were in low volumes of TY. ELISA for the murine uPA receptor were performed using a commercially available kit (Biomatik) according to the manufacturer's instructions following collection of supernatant and filtration through a 0.2 micron filter.

Mouse model of AL. The experiments disclosed herein used the validated model of pathogen-mediated AL in mice (8'). Ten- to 12-week-old C57BL/6 mice (Charles River) were provided standard chow and tap water ad libidum at all times. When indicated, mice received oral clindamycin (100 mg/kg gavage) and subcutaneous cefoxitin (40 mg/kg) the day prior to, and the day of, surgery. Mice underwent general anesthesia with intraperitoneal ketamine and xylocaine and laparotomy followed by transection of the colon at the colo-rectal junction followed by a primary anastomosis created with interrupted 8-0 prolene suture prior to abdominal closure with 4-0 vicryl suture in two layers. Rectal enemas containing pathogen, either E. faecalis or P. aeruginosa at an $OD_{600}$ of 0.1 in 10% glycerol, were administered in 100 L enemas. E. faecalis was introduced on POD 1, 2, and 3, while P. aeruginosa was introduced only on POD 1. Mice received 100 L rectal enemas containing 50 mM TXA or vehicle control on postoperative days 1, 2, and 3. Rectal delivery with a gavage needle ensured local administration of pathogen and study drugs to the surgical site. Rules for stopping the experiment were enacted if mice appeared moribund or in any distress whereby they were sacrificed immediately. There were three deaths prior to planned sacrifice, all determined secondary to feculent peritonitis due to AL. Both the surgeon and the investigator performing analysis of healing were blind to the treatment group.

Imaging. PLG binding at the anastomotic site: Mice underwent anastomotic surgery without postoperative introduction of pathogen. Anastomotic sites were collected and incised longitudinally to create a single layer sheet of tissue. Each sheet was incubated with 2 M FITC-labeled PLG in PBS for an hour and imaged at 40× magnification to create light images with FITC-range fluorescent overlay.

Co-localization of E. faecalis and PLG: Mice underwent anastomotic surgery with postoperative introduction of E. faecalis V583. The mice received post-operative TXA or vehicle enemas as described herein. They received a systemic (intra-peritoneal) injection of 100 L 4 M FITC-labeled PLG one hour prior to sacrifice. Anastomotic tissue was collected in sterile fashion and cryosectioned. Slides were stained with 4',6-diamidino-2-phenylindole (DAPI) for colonic mucosa. For visualization of microbial organisms, the inventors used probes designed by Miacom Diagnostics, which use a fluorescence in situ hybridization (FISH) beacon-based technology. An E. faecalis-specific probe was labeled with Alexa Fluor 647. Staining was performed overnight per the manufacturer's protocol. Confocal microscopy was performed on a Leica SP5 II AOBS tandem scanner spectral confocal system on a DMI6000 microscope and controlled by LASAF software (version 2.8.3). Four channels were collected at each location using sequential excitation (excitation: 405, 488, and 633; emission: 412-452, 495-537, and 654-755 nm pass bands) on either photomultiplier or HyD hybrid detectors. Objectives used were ×20, NA 0.7 dry, ×10, NA 0.7 dry, and ×40, NA 1.40 oil (Leica).

Quantitative microbiologic analysis. Anastomotic tissue was collected on necropsy in a sterile fashion and placed in 10% glycerol. Luminal contents were removed from tissue and stored similarly. Each sample was weighed and processed in a bead homogenizer. Samples underwent serial dilutions and 50 L were spread onto skim milk agar plates with enterococcal selective media and allowed to grow for 48 hours at 37° C. Collagenolytic colonies were identified by clearing of skim milk and counted by hand to calculate CFU/mL normalized to sample weight.

Additional Statistical Analyses. Statistical analyses were performed using Graphpad Prism 8 software. Unpaired Student's t-tests were used for comparisons between two means for continuous variables. ANCOVA analysis was applied to compare slopes of regression lines in enzyme activity assays. Chi-square analysis was used for comparison of categorical variables. Cellular populations were compared in flow cytometric experiments through automated Kolmogorov-Smirnov analysis on FlowJo software. Statistical significance was defined as a p value <0.05.

Example 2

Figure 8:
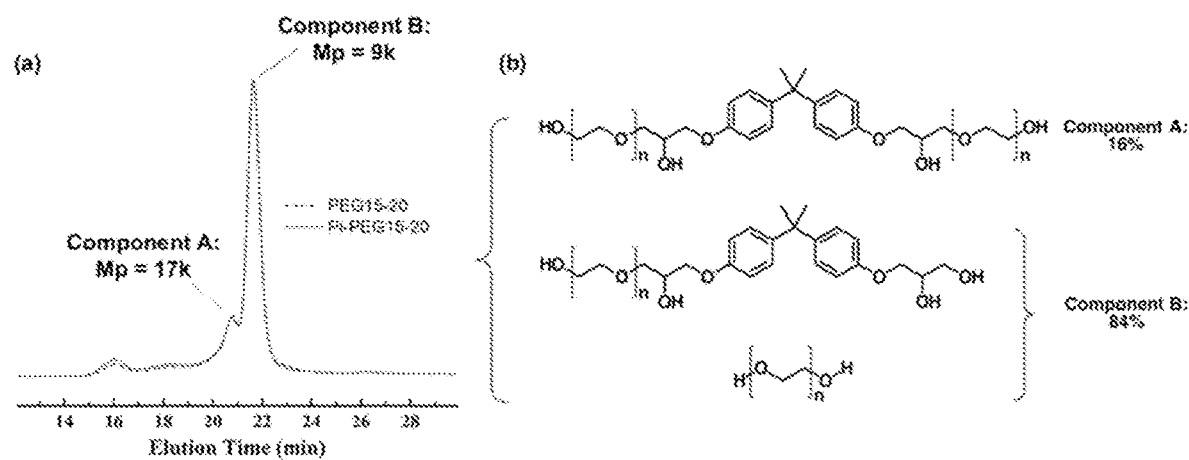
FIG. 8. Composition analysis of PEG 15-20 (Sigma) and Pi-PEG 15-20. (A), GPC traces of commercial PEG 15-20 and its phosphorylated product Pi-PEG15-20 in 0.1 M NaNO$_3$ (25° C., 1.0 ml/min) indicate that PEG 15-20 is a mixture of copolymers with ABA and AB structures, and homopolymers (B). The analysis defines 16% of PEG 15-20 to contain ABA structure as calculated from the integration area of GPC curve.

Design and synthesis of phosphorylated PEG-based block copolymer with a hydrophobic core (ABA-PEG-Pi). The purpose of this study was to develop phosphate-containing PEG-based block copolymers with a defined ABA structure and molecular weight and identify their effectiveness to suppress microbial virulence using biological tests. In previous work [3], a phosphorylated product from commercially available polymer PEG 15-20 (Pi-PEG 15-20) was employed and proven to work effectively in preventing lethal gut-derived sepsis. In these studies, the inventors learned that the ABA structure and phosphate were critical determinants for the biologic function of Pi-PEG 15-20. However, molecular weight measurements (FIG. 8) indicated that both Pi-PEG15-20 and its precursor PEG 15-20 were polydisperse, i.e., PEG 15-20 contained component A, 16% of block copolymer with ABA structure, and component B, 84% of block copolymer with an AB structure and a PEG homopolymer. The phosphorylated homopolymer failed to show a protective effect in biological tests [3], and separating it from the original polydisperse mixture to refine the active component proved implausible, since it has an almost identical molecular weight to the block copolymer with an AB structure and since they both are water-soluble. As such, this complex composition presented challenges to determine the mechanism of protection of each component. Therefore, a rational design of an alternative PEG with uniform composition and similar structure to the active components in Pi-PEG 15-20 was required in order to achieve both key features of the ABA structure and controllable phosphate content.

PEG chains contain only one or two terminal hydroxyl groups suitable for further functionalization. To incorporate more hydroxyl groups per polymer chain, sequential anionic copolymerization of ethylene oxide (EO) with a functional epoxide monomer, ethoxy ethyl glycidyl ether (EEGE), an ethoxy ethylacetal protected glycidol was used to acquire block copolymers with polyethylene oxide as backbone, along with controllable hydroxyl groups [20-22]. As depicted in Scheme 1, the design of ABA-PEG-Pi involves the initial synthesis of symmetric block copolymer ABA-PEG-PEEGE from Bisphenol A, followed by de-protection of PEEGE block to recover the pendant hydroxyl groups, and the subsequent functionalization of all the hydroxyl groups of the block copolymer with phosphate.

Scheme 1. Synthetic strategy of ABA-PEG-Pi block copolymers.
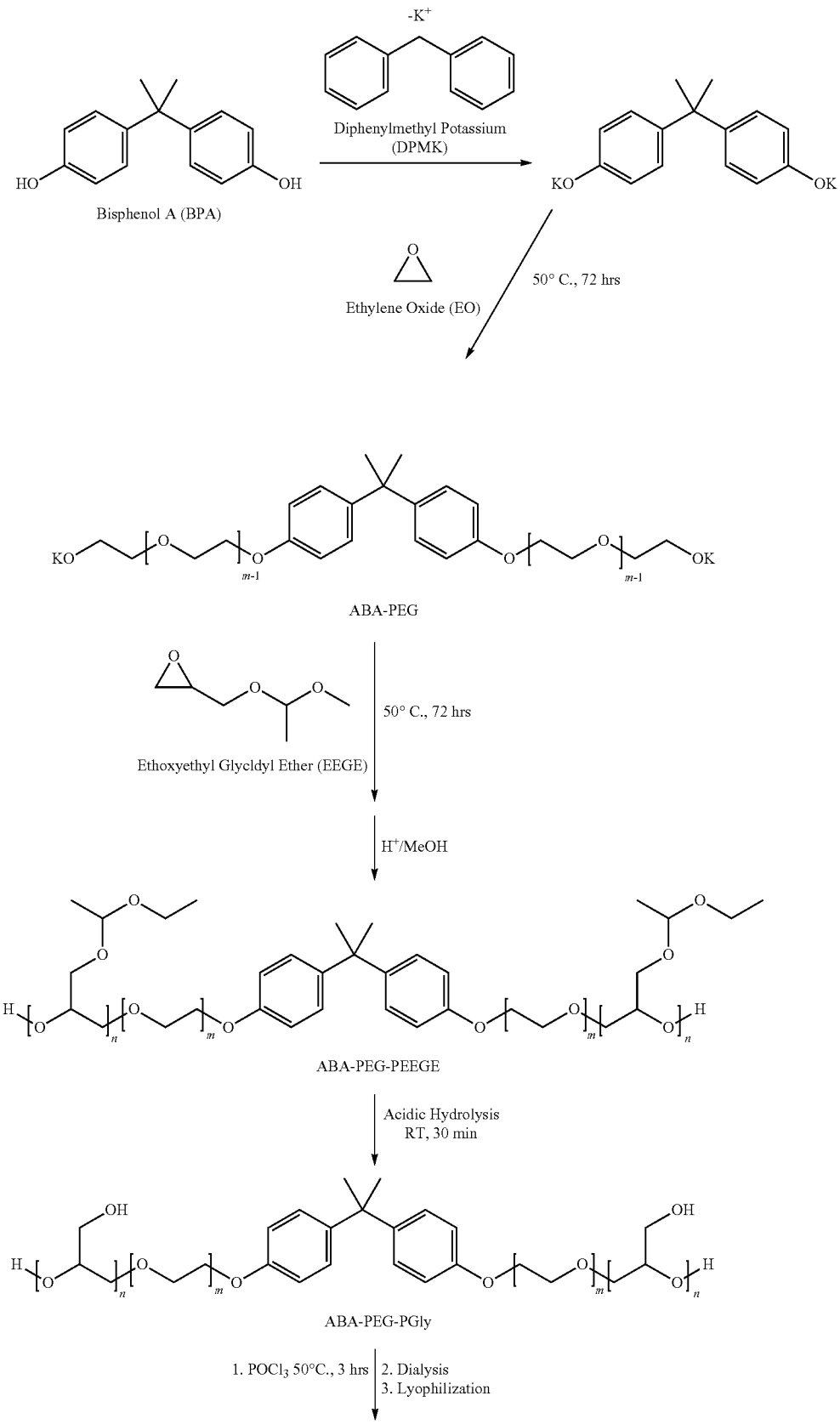

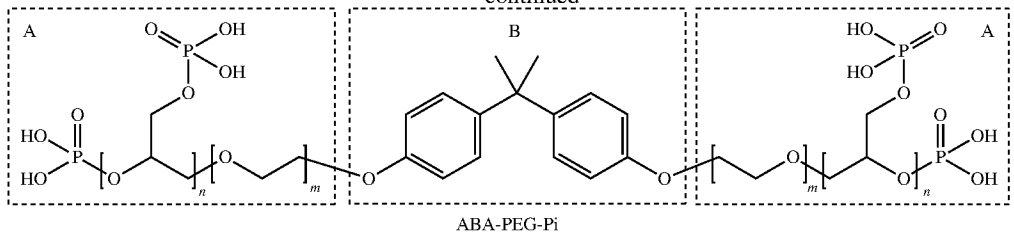

ABA-PEG-Pi

This strategy allowed access to a series of block copolymers with defined ABA architecture, which consisted of three distinctive segments: (i), B group represents the small, yet very hydrophobic bis-phenol A moiety at the polymer center. (ii), PEG blocks adjacent to the bi-aromatic center formed the inert spacer and the inner part of hydrophilic A groups. As an integral part of the architecture, the chain length of the PEG block played a key role in the hydrophobicity/hydrophilicity balance of the whole polymer. (iii), phosphorylated polyglycidol block acts as the outer part of hydrophilic A groups, offering biological functionality and defined phosphate content. Three ABA-PEG-Pis: ABA-PEG10k-Pi10, ABA-PEG16k-Pi14 and ABA-PEG20k-Pi20 were synthesized in this study. 10k, 16k and 20k corresponded to the different molecular weight of PEG block. By incorporating repeating units of phosphate accordingly (from 10, 14 to 20, respectively), almost identical molar concentration of phosphate can be maintained for each block copolymer (e.g., for 1 g of each block copolymer, the molar concentration of phosphate were 0.78, 0.77 and 0.80 mmol respectively for ABA-PEG10k-Pi10, ABA-PEG16k-Pi14 and ABA-PEG20k-Pi20).

Initiated from potassium bis-phenoxide, the sequential anionic ring-opening polymerization of EO and EEGE was successful. This can be confirmed by the chemical shifts seen in $^1$H-NMR spectra (FIG. 1A): a ($\delta$=1.60, 6H) and b ($\delta$=6.78, 7.09, 8H) are assigned to the dimethyl and aromatic groups of BPA, c~h ($\delta$=3.43-3.80) can be assigned to protons of the main chain and lateral chains, i ($\delta$=4.70, 1H), j ($\delta$=1.29, 3H) and k ($\delta$=1.19, 3H) are ascribed to the methyl protons of the EEGE moiety. Furthermore, the chain length of the PEG and PEEGE blocks could be varied by adjusting the feed ratio of EO and EEGE monomer to the initiator BPA, and the composition of the block copolymer can be determined by the integrals of specific signals from each block in $^1$H-NMR spectra. The degree of polymerization of PEEGE block ($N_{EEGE}$) can be calculated by the integration ratio:

$$N_{EEGE} = 8 * \frac{I_i}{I_b}$$

where $I_i$ and $I_b$ are the integration of Peak i and b in FIG. 1, respectively.
The degree of polymerization of PEG block ($N_{EG}$) was given by $$N_{EG} = 2 * \frac{I_{c\sim h} - 7 N_{EEGE} * I_i}{I_b}$$

where $I_{c\sim h}$ is the integration of Peak c~h in FIG. 1. Detailed molecular weights characterization results for all the samples are summarized in Table 1.

TABLE 1

Molecular characterization of PEG-based block copolymer with hydrophobic core.

| | | $M_n{}^a$ (kDa) GPC | $M_n$ (kDa) NMR | $D^b$ | $N_{EEGE}{}^c$ | $N_{hydroxyl}{}^d$ | $N_{phosphate}{}^e$ |
|---|---|---|---|---|---|---|---|
| ABA-PEG-PEEGE | ABA-PEG10k-E8 | 26.1 | 12.4 | 1.05 | 8.0 | | |
| | ABA-PEG16k-E12 | 31.7 | 17.8 | 1.07 | 11.6 | | |
| | ABA-PEG20k-E18 | 35.9 | 24.6 | 1.04 | 17.5 | | |
| ABA-PEG-PGly | ABA-PEG10k-G10 | 23.2 | 11.9 | 1.06 | | 10.0 | |
| | ABA-PEG16k-G14 | 27.8 | 17.1 | 1.06 | | 13.6 | |
| | ABA-PEG20k-G20 | 31.1 | 23.3 | 1.05 | | 19.5 | |
| ABA-PEG-Pi | ABA-PEG10k-Pi10 | 12.9 | 12.8 | 1.10 | | | 9.8 ± 0.2 |
| | ABA-PEG16k-Pi14 | 18.7 | 18.2 | 1.08 | | | 13.0 ± 0.8 |
| | ABA-PEG20k-Pi20 | 25.8 | 25.0 | 1.07 | | | 19.5 ± 0.5 |

Nomenclature of the polymers: Take ABA-PEG10k-ES/ABA-PEG10k-G10/ABA-PEG10k-Pi10 as examples, 10k is the designed molecular weight of PEG block; ES means the designed repeating units of EEGE block is 8; G10 means the designed repeating units of Glycerol is 10. Because hydrolysis of EEGE block released 8 alcohol groups, plus 2 primary alcohol groups at chain ends, made it 10 repeating units for Glycerol; Pi10 indicates the designed repeating units of phosphorylated Glycerol block is 10. Other polymers can be deduced in the same manner.

a: ABA-PEG-PEEGE and ABA-PEG-PGly samples were measured in THF against PS standards; ABA-PEG-Pi samples were measured in 0.1 M NaNO$_3$ against PEO standards.
b: Measured by GPC.
c: Calculated from NMR.
d: $N_{hydroxyl}$=$N_{EEGE}$+2 primary alcohol groups at chain ends, NMR confirmed the complete of the de-protection.
e: $N_{phosphate}$ of ABA-PEG-Pi samples were determined by phosphoric acid titration experiments.

EEGE was chosen to be the outer block, due to the advantages that: (i) it has similar main chain with PEG, can be co-polymerized with EO through anionic mechanism, (ii) this structural similarity also suggests that PEG-PEEGE should be non-toxic and safe, which is important when further developing ABA-PEG-PEEGE for biomedical applications, and (iii) the protective ethoxy ethylacetal groups can be easily removed by acidic hydrolysis, yielding pendant hydroxyl group in each repeating unit, offering perfect functionalization sites for phosphorylation. Complete hydrolysis could be verified by the disappearance of specific EEGE signals i, j and k, comparing FIG. 1A and FIG. 1B. Finally, phosphorylation was performed by the reaction between ABA-PEG-PGly samples with phosphorus oxychloride, which was shown to be highly effective in the inventors' previous work [3]. The existence of phosphate in ABA-PEG-Pi samples can be verified by the chemical shift δ=−0.18 ppm in $^{31}$P-NMR spectrum (FIG. 1D). The number-average molecular weights of ABA-PEG-Pi measured by GPC for ABA-PEG10k-Pi10, ABA-PEG16k-Pi14 and ABA-PEG20k-Pi20 were 12.9k, 18.7k and 25.8k, respectively, and corresponded well with those determined from NMR results also shown in Table 1 (12.8k, 18.2k and 25.0k, respectively), which implied that the degree of functionalization of the available hydroxyl groups was complete.

In order to further identify the degree of phosphorylation, phosphoric acid titration experiments were performed to identify the average number of phosphate groups per polymer chain. Briefly, 0.1M of sodium hydroxide (NaOH) solution was titrated into the ABA-PEG-Pi/PEG-Pi solution, and the pH changes monitored using a pH meter with automatic temperature compensation. FIG. 1E shows a typical titration curve, pH value of the solution increased with the gradual addition of NaOH (left axis), two buffer region (gray column area) were observed; after simply taking the first derivation (right axis), two equivalence points were clearly visualized. It shows the characteristic behavior of a diprotic acid, and the relatively broader peaks during the buffer region implied the behavior of poly(phosphoric acid) as well. These results are in accordance with the structure of phosphoric acid units on the polymer chain. The average number of phosphate groups per polymer chain $N_{phosphate}$ can be calculated by equation:

$$N_{phosphate} = \frac{[NaOH] * V_1}{m/M_n} \text{ or } N_{phosphate} = \frac{[NaOH] * V_2}{2m/M_n}$$

where [NaOH] is the concentration of sodium hydroxide solution, $V_1$ and $V_2$ are the volume of sodium hydroxide solution consumed at $1^{st}$ titration end and $2^{nd}$ titration end, respectively. m is the mass of ABA-PEG-Pi polymer used in the titration, and $M_n$ is the number average molecular weight of ABA-PEG-Pi polymer. Theoretically, the volume of NaOH solution consumed at $2^{nd}$ titration end ($V_2$) should be twice as that at the $1^{st}$ titration end ($V_1$), $V_2$ is a little bit lower than $2V_1$, this may be due to the dissociation constant difference between the phosphoric acid units at the chain ends and those far from the chain ends.

Through the above method, the average number of phosphate groups per polymer chain $N_{phosphate}$ for ABA-PEG10K-Pi10, ABA-PEG16K-Pi14 and ABA-PEG20K-Pi20 are 9.8±0.2, 13.0±0.8, and 19.5±0.5. These results confirm the assumption that the degree of phosphorylation of the available hydroxyl groups was complete.

Example 3

Figure 9:
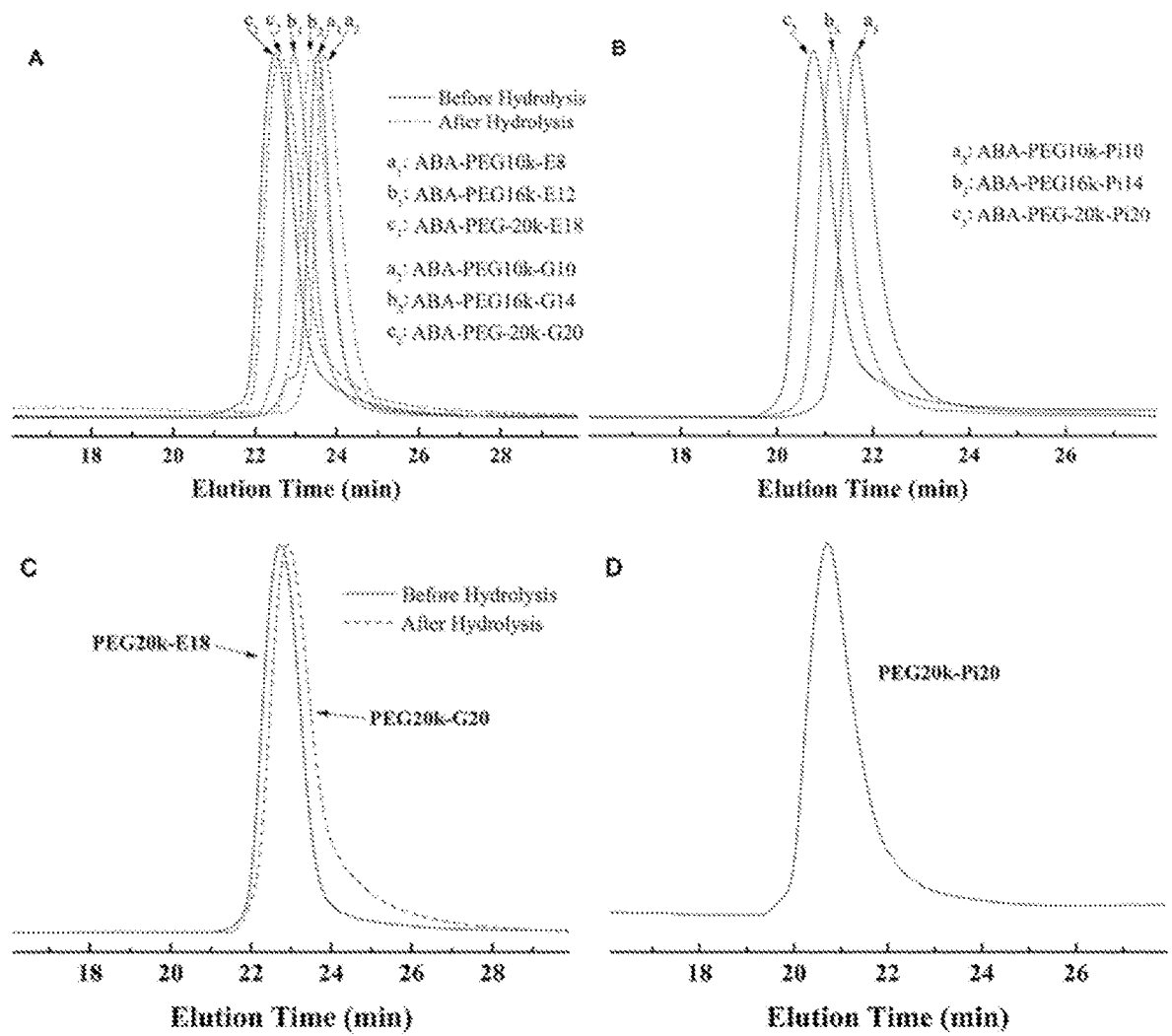
FIG. 9. GPC traces of (A) ABA-PEG-PEEGE, ABA-PEG-PGly in THF (35° C., 0.8 ml/min), (B) ABA-PEG-Pi in 0.1 M NaNO₃ (25° C., 1.0 ml/min), (C) PEG-PEEGE, PEG-PGly in THF (35° C., 0.8 ml/min) and (D) PEG-Pi in 0.1 M NaNO₃ (25° C., 1.0 ml/min).
Figure 10:
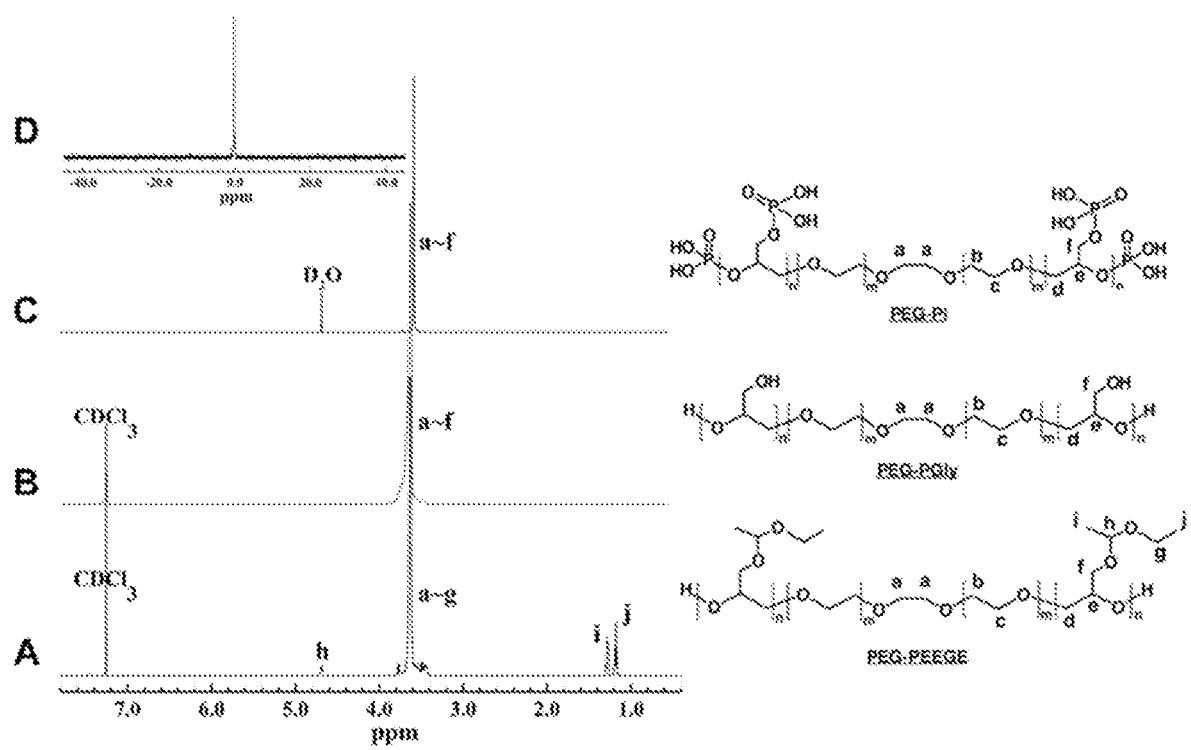
FIG. 10. $^1$H-NMR spectra of (A) PEG20k-E18, (B) PEG20k-G20, (C) PEG20k-Pi2O and (D)$^{31}$P-NMR spectrum of PEG20k-Pi2O.

Synthesis of phosphorylated PEG-based block copolymer without hydrophobic core (PEG-Pi). In order to demonstrate the structural importance of the hydrophobic moiety, another phosphate-containing PEG based block copolymers without hydrophobic core, namely, PEG-Pi was also synthesized for comparison. The only structural difference between PEG-Pi and ABA-PEG-Pi is the center moiety (FIG. 2): for PEG-Pi, it's ethylene glycol; whereas for ABA-PEG-Pi, it's BPA. As depicted in Scheme 2, the synthesis of PEG-Pi started from ethylene glycol, through the same sequential anionic ring-opening polymerization of EO and EEGE, hydrolysis and phosphorylation, produced the final product PEG-Pi. Only PEG20k-Pi20 was synthesized in this study. As with ABA-PEG20k-Pi20, 20k corresponded to the designed molecular weight of PEG block, 20 was the designed repeating units of phosphate incorporated on each chain. GPC elution curve analyses demonstrated the uniform composition in the synthesized polymers (FIG. 9). The polymerization, hydrolysis and phosphorylation were similarly monitored by NMR spectroscopy. The spectra are shown in FIG. 10. a~g (δ=3.43-3.80) can be ascribed to protons of the main chain and lateral chains, h (δ=4.70, 1H), i (δ=1.29, 3H) and i (δ=1.19, 3H) are assigned to the methyl protons of the EEGE moiety. The disappearance of signals h, i and j confirmed the complete of hydrolysis, and the chemical shift δ=−0.17 ppm in $^{31}$P-NMR spectrum verified the existence of phosphate in PEG20k-Pi20. The average number of phosphate groups per polymer chain $N_{phosphate}$ for PEG20k-Pi20 calculated from phosphoric acid titration experiment is 19.8±0.3, indicated nearly 100% of phosphorylation. The number-average molecular weights measured by GPC for PEG20k-E18, PEG20k-G20 and PEG20k-Pi20 were 36.5k, 31.6k and 26.2k, respectively, which are very close to those values of ABA-PEG20k-Pi20, making PEG20k-Pi20 an excellent analogue to ABA-PEG20k-Pi20. Detailed molecular weights characterization results, GPC elution curves and NMR spectra are summarized in Table 2 and FIGS. 9 and 10.

It is also important to note that, due to the use of a living anionic polymerization technique, the dispersity (Đ) of all these PEG-based block copolymers were kept narrow (<1.10), significant broadening of the corresponding GPC traces was not observed even after de-protection and phosphorylation (FIG. 9), indicating excellent control over molecular weight, architecture and the number of phosphate units that were desired for biological tests.

Example 4

Figure 3:
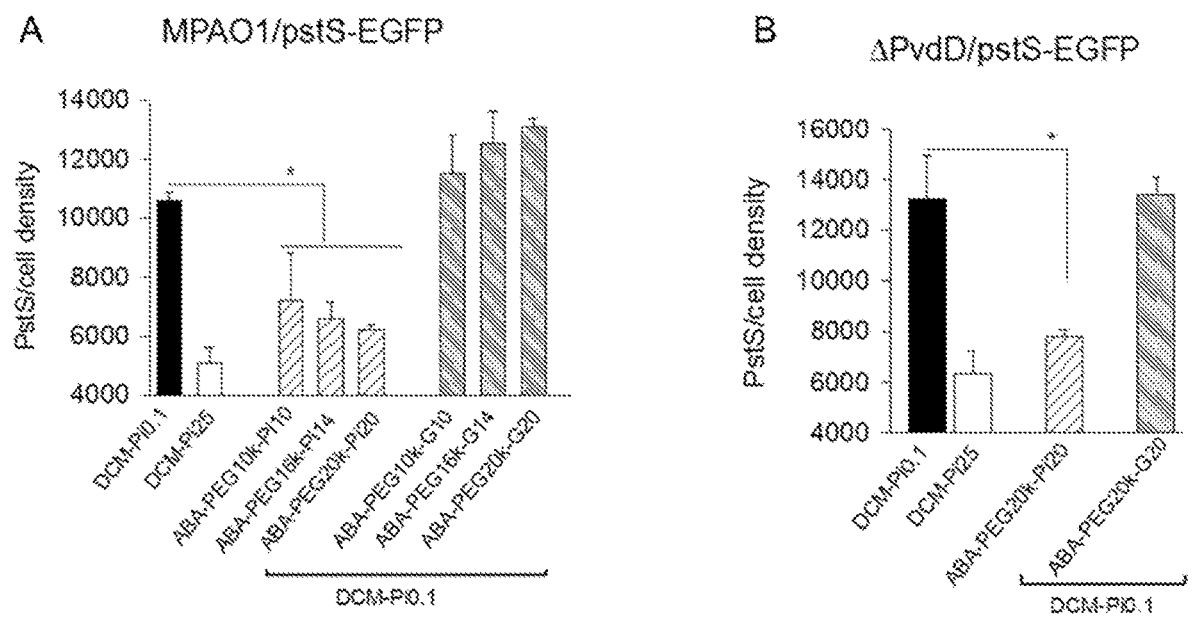
FIG. 3. ABA-PEG-Pis significantly decrease PstS expression in *P. aeruginosa*. PstS expression in MPAO1/pstS-EGFP (A), and APvdD/pstS-EGFP (B). n=3 per group, *p<0.01. Columns represent average values, and error bars-standard deviations. DCM-Pi0.1 indicates citrate medium containing limited quantities (0.1 mM) of inorganic phosphate, DCM-Pi25 indicates citrate medium containing sufficient quantities (25 mM) of inorganic phosphate.
Figure 11:
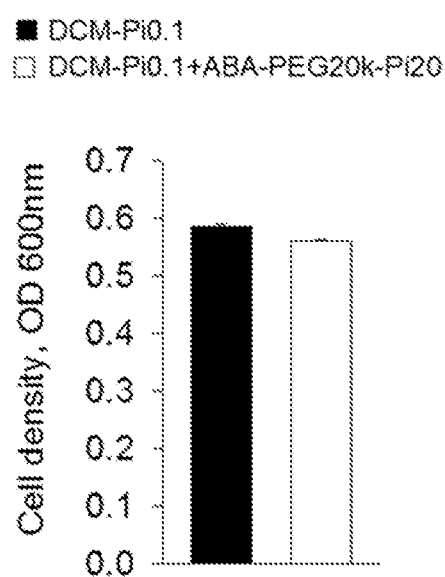
FIG. 11. ABA-PEG20k-Pi2O does not inhibit growth of *P. aeruginosa*. Absorbance at OD600 nm measured in overnight culture of *P. aeruginosa* MPAO1/psts-EGFP in DCM-Pi0.1 and DCM-Pi0.1 supplemented with 2 mM ABA-PEG20k-Pi20. Results present mean data of three biological replicates.

ABA-PEG-Pis inhibit phosphate signaling in *P. aeruginosa* under phosphate limiting conditions. Multiple biological tests were performed to assess the functionality of the synthesized polymers as anti-virulence compounds. Expression of the phosphate transport protein PstS in *P. aeruginosa* was used as a biomarker to determine phosphate availability of the various polymers. If PstS expression was increased, it served as a proxy indicating that extracellular phosphate was depleted and unavailable within the phosphorylated compound. On the other hand, if PstS was observed to be decreased, it indicated that *P. aeruginosa* detected sufficient phosphate availability in the test compound. PstS is the phosphate-binding component of the ABC-type transporter complex pstSACB involved in phosphate transport into the bacterial cytoplasm. PstS is known to be induced by phosphate limitation and suppressed in a phosphate rich extracellular environment. In order to track the expression of PstS, the inventors first constructed the pSensor-PstS-EGFP plasmid (see Material and Methods) that was electroporated in the *P. aeruginosa* MPAO1-P1 strain to get MPAO1-P1/pstS-EGFP reporter strain. The expression of pstS was detected by fluorescence (excitation 485/10, emission 528/20) normalized to cell density measured by the absorbance at 600 nm. As a control, PstS expression in *P. aeruginosa* grown in low phosphate and high phosphate defined citrated media (DCM) was used. Data indicated, as expected, that PstS expression was increased in low phosphate medium and was nearly completely suppressed in medium containing 25 mM of inorganic phosphate. All three phosphorylated polymers (ABA-PEG10k-Pi10, ABA-PEG16k-Pi14 and ABA-PEG20k-Pi20, 2 mM) (FIG. 3A) suppressed PstS expression suggesting that Pi was available for bacteria. In contrast, the non-phosphorylated parent polymers ABA-PEG10k-G10, ABA-PEG16k-G14, and ABA-PEG20k-G20 did not suppress PstS expression demonstrating that there was no effect of the nascent ABA structure on the PstS expression via some type of non-specific interaction (FIG. 3A). The inventors then performed reiterative experiments in which the inventors used ΔPvdD/pstS-EGFP strain, a pyoverdin-deficient mutant derivative of MPAO1-P1 harboring pSensor-PstS-EGFP. By using this mutant, the inventors verified that the decrease in fluorescence observed with ABA-PEG-Pis was indeed attributable to decreased PstS expression and not to the production of pyoverdin, a fluorescent compound that is also produced in this medium [23]. The pattern of PstS expression in ΔPvdD/pstS-EGFP was similar to that observed with the MPAO1-P1/pstS-EGFP (FIG. 3B). These data demonstrate that phosphorylated polymers suppress the main signal indicating phosphate limitation, i.e., PstS expression. Phosphorylated polymers did not inhibit bacterial growth (FIG. 11) which is in agreement with the inventors' previous data [3].

Figure 4:
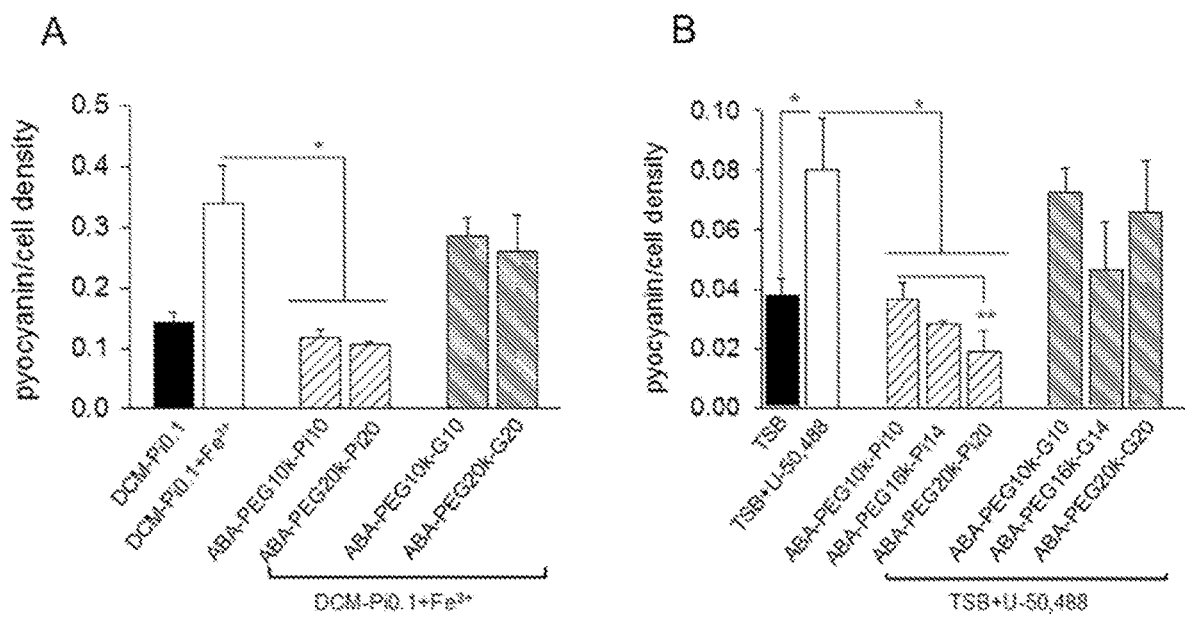
FIG. 4. ABA-PEG-Pis significantly decrease pyocyanin production in *P. aeruginosa*. (A), production of pyocyanin in *P. aeruginosa* MAPO1-P2 grown in phosphate/iron limited medium DCM-Pi0.1, phosphate limited medium DCM-Pi0.1+Fe$^{3+}$, 2 μM, and phosphate limited/iron enriched media supplemented with 1 mM phosphorylated and non-phosphorylated polymers. (B), production of pyocyanin in MPAO1-P1 in TSB supplemented with 0.2 mM U-50,488 in the presence or absence of phosphorylated and non-phosphorylated polymers. n=3 per group, *p<0.01. Columns represent average values, and error bars-standard deviations.

ABA-PEG-Pis significantly decrease pyocyanin production by *P. aeruginosa* under phosphate limited conditions and during exposure to opioids. One of the most distinguishing features of strains of *P. aeruginosa* is their production of pyocyanin, a water soluble blue green phenazine compound. Pyocyanin is one of the major toxins of *P. aeruginosa* that induces rapid apoptosis of human neutrophils, and thus defines the virulence of this highly lethal opportunistic pathogen. The production of pyocyanin is controlled by the quorum sensing system (QS), a central virulence circuit in *P. aeruginosa* and other pathogens. The PstS-PhoB phosphate regulon, a two component membrane regulator, is activated during phosphate limitation and is involved in the transcriptional activation of QS. Thus, enrichment of media with phosphate leads to suppression of pyocyanin production [23, 24]. Therefore, the inventors next tested if ABA-PEG-Pi can suppress pyocyanin production in *P. aeruginosa* in phosphate limited medium using DCM-Pi0.1. In this set of experiments, the inventors used a MPAO1-P2 strain that produces a higher amount of pyocyanin compared to the MPAO1-P1 strain [16]. In preliminary experiments, the inventors found that supplementation of media with iron increases pyocyanin production in this nutrient limited DCM media. Therefore, the inventors supplemented DCM with 2 $\mu$M $Fe^{3+}$ (1 $\mu$M $Fe_2(SO_4)_3$). Results demonstrated that both ABA-PEG10-Pi10 and ABA-PEG20-Pi20 significantly decreased pyocyanin production in *P. aeruginosa* MPAO1-P2 (FIG. 4A). The effect of non-phosphorylated compounds was significantly lower.

The inventors have demonstrated that endogenous opioid compounds are released into the intestine during physiologic stress and induce pyocyanin production via the quorum sensing (QS) system of virulence activation [17, 25]. The inventors established that the MPAO1-P1 strain is highly responsive to the synthetic kappa opioid U-50,488 in terms of pyocyanin production [17]. Consistent with previous results, the inventors again demonstrated that pyocyanin production was significantly increased in MPAO1-P1 when exposed to 200 $\mu$M of the kappa-opioid receptor agonist U-50,488 (FIG. 4B). All three ABA-PEG-Pis polymers reduced pyocyanin at the expected background level, with ABA-PEG20k-Pi20 being the most effective.

The paired molecular weight non-phosphorylated polymers were less effective in these experiments, again suggesting that that the polymers phosphate content is important for its suppressive effect on pyocyanin production.

Example 5

ABA-PEG-Pis attenuate animal mortality caused by *P. aeruginosa* exposed to opioids. The inventors developed two small animal models (i.e., *Caenorhabditis elegans* and mice) to create local phosphate depletion at sites of colonization of *P. aeruginosa*, and validated the fidelity between these models [23, 26].

Figure 5:
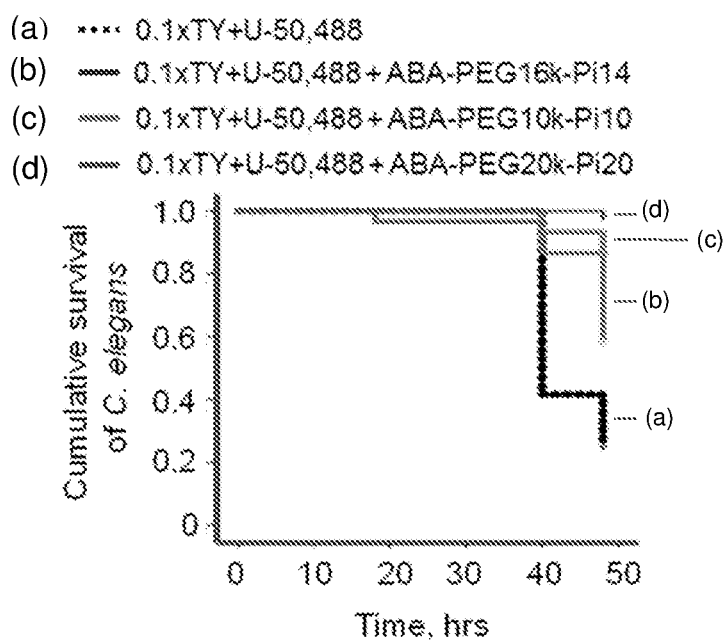
FIG. 5. Effect of each of the three phosphorylated ABA polymers on *C. elegans* survival. Experiments are performed on *C. elegans* nematodes feeding on *P. aeruginosa* in low nutrient media (0.1× TY) and exposed to opioids (U50,488) as a provocative agent known to enhance *P. aeruginosa* virulence. Kaplan-Meyer survival curves demonstrate a statistically significant (p<0.05) protective effect of all three polymers at 2 mM concentration when compared to the no treatment group. Results indicate that the ABA-PEG20k-Pi2O confers a superior protective effect compared to the remaining polymers (n=10 worms/plate (treatment group), 3 independent runs per group.
Figure 12:
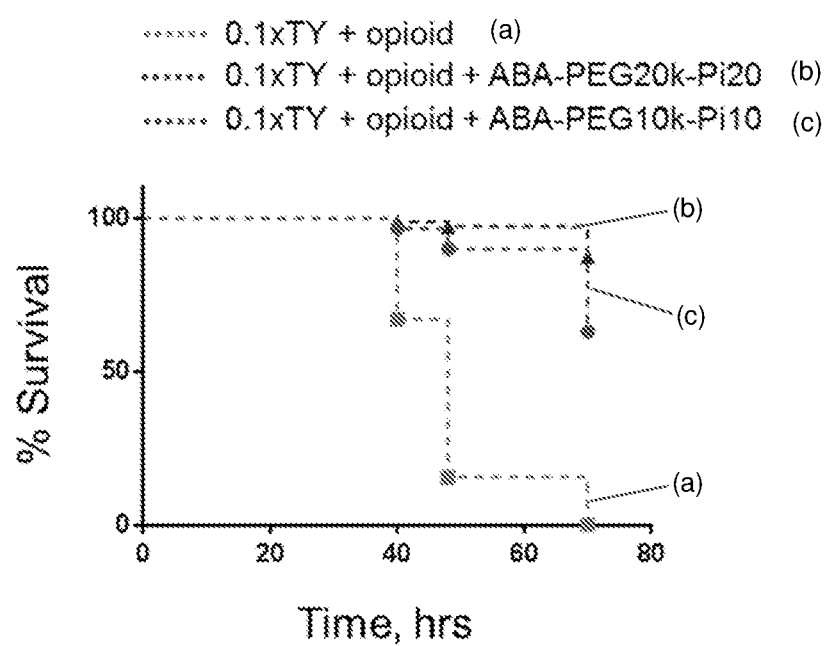
FIG. 12. Effect of phosphorylated ABA polymers on *C. elegans* survival. Experiments are performed on *C. elegans* nematodes feeding on *P. aeruginosa* in low nutrient media (0.1× TY) and exposed to opioids (U50,488) as a provocative agent known to enhance *P. aeruginosa* virulence. Kaplan-Meyer survival curves demonstrate a statistically significant (p=0.01, Log-rank Mantel-Cox test) protective effect of ABA-PEG20k-Pi20 compared to ABA-PEG10k-Pi10 at 5% concentration. Both polymers have significant protective effect compared to no-PEG group (p<0.0001, Log-rank Mantel-Cox test). Results indicate that the ABA-PEG20k-Pi20 confers a superior protective effect compared to the remaining polymers (n=10 worms/plate (treatment group), 3 independent runs per group).

Therefore, in current work the inventors have used the *C. elegans* model in which the opioid-induced lethality of *P. aeruginosa* can be suppressed by the delivery of inorganic phosphate [18]. In order to test the in vivo efficacy of the de novo synthesis Pi-PEG compounds the inventors created conditions of both opioid exposure and phosphate limitation. Results indicated that all three ABA-PEG-Pi polymers, at equal concentrations 2 mM effectively decreased *C. elegans* mortality (FIG. 5) with the ABA-PEG20k-Pi20 displaying the greatest degree of protection. Since ABA-PEG20k-Pi20 carries the highest phosphate at equal molarity, to verify that the protective effect is not dependent on phosphate concentration, the inventors performed reiterative experiments comparing ABA-PEG10k-Pi10 to ABA-PEG20k-Pi20 at concentrations of 5 wt %. At the same weight concentration, ABA-PEG20k-Pi20 and ABA-PEG10k-Pi10 contain nearly equal quantities of phosphate. Results demonstrated that ABA-PEG20k-Pi20 still exhibited a significantly higher protective effect compared to ABA-PEG10k-Pi10 (FIG. 12), suggesting that the higher molecular weight may influence the greater protective effect of ABA-PEG20k-Pi20.

Figure 2:
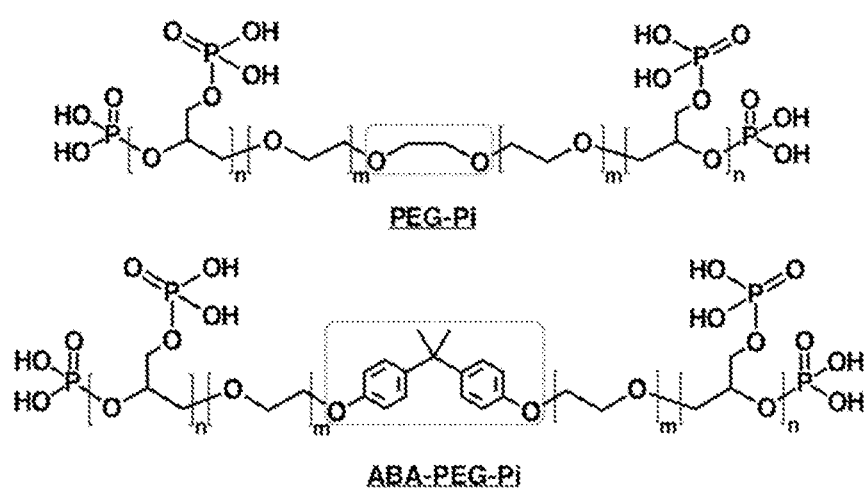
FIG. 2. Comparison of the chemical structure of phosphate-containing PEG-based block copolymers: ABA-PEG-Pi with the hydrophobic core BPA and PEG-Pi without BPA.
Figure 6:
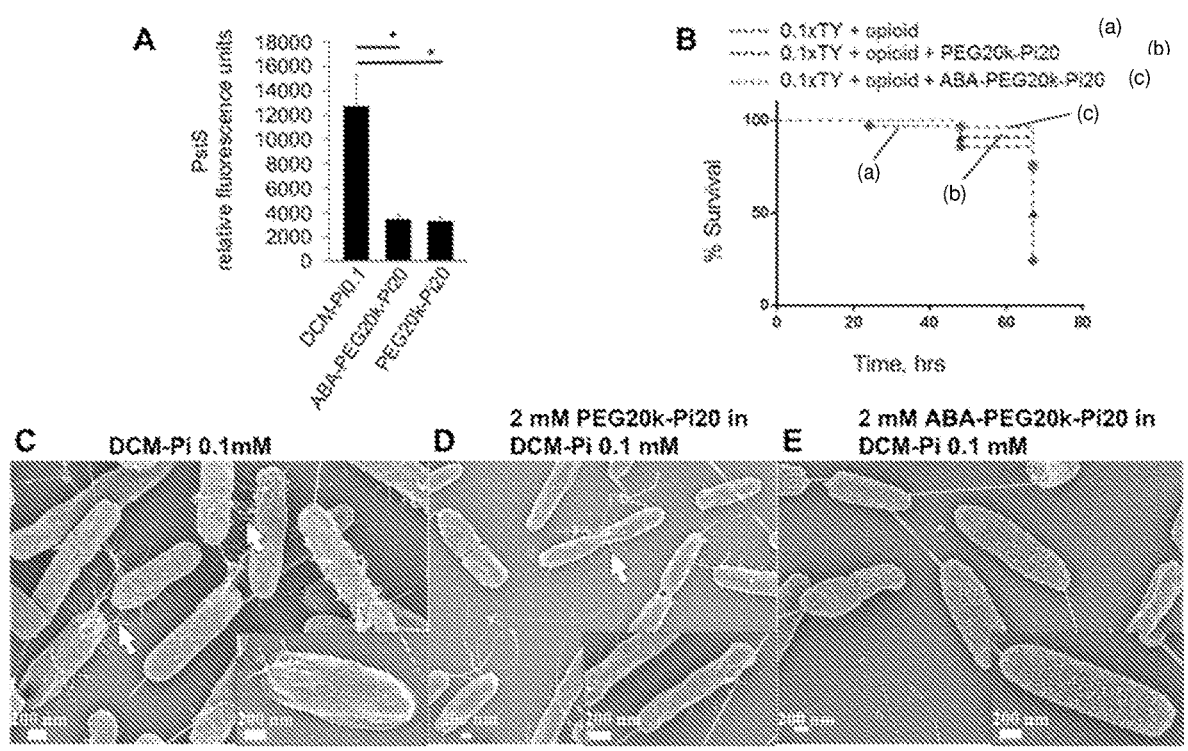
FIG. 6. The hydrophobic core BPA in ABA-PEG20k-Pi2O significantly contributes to bacterial coating and its in vivo protection against lethality. (A), PstS expression. N=3/group, *p<0.001. (B), *C. elegans* survival. N=60/group, p<0.0001 between groups (Long-rank (Mantiel-Cox) test). (C-E), Scanning electron microscopy images of *P. aeruginosa* cultured in different media. The bacteria were first cultured in different media for several hours, then immediately after washing with buffer solution, dried in a critical point dryer, coated with Pt/Pd and images taken. Arrows indicate pili-like filaments. (C), cultured in phosphate-limited (DCM Pi-0.1 mM) media only, (D) cultured in DCM Pi-0.1 mM containing 2 mM PEG20k-Pi2O and (E) cultured in DCM Pi-0.1 mM containing 2 mM ABA-PEG20k-Pi2O.

The hydrophobic core BPA in ABA-PEG20k-Pi20 significantly contributes to bacterial coating and its in vivo protection against lethality. In order to confirm the hypothesis that it is the unique ABA structure of ABA-PEG20k-Pi20 that plays a significant role in its protective capacity, the inventors synthesized PEG20k-Pi20. This polymer has a similar structure to ABA-PEG20k-Pi20 but lacks the hydrophobic core (FIG. 2). As presented in FIG. 6A, results showed that both phosphorylated polymers suppressed PstS expression to the same degree, demonstrating that both can serve as phosphate delivery molecules. However, in *C. elegans* experiments, the protective effect of amphiphilic ABA-PEG20k-Pi20 is significantly greater compared to the hydrophilic PEG20k-Pi20 molecule (FIG. 6B). Because the inventors have previously demonstrate that ABA-PEGs may adhere to and shield the bacterial surface, the inventors next tested whether the coating capacity of ABA-PEG20k-Pi20 and PEG20k-Pi20 are different. This was performed using scanning electron microscopy (SEM) on *P. aeruginosa*. Bacteria were cultured in different media for several hours, then immediately after washing with buffer solution, they were dried in a critical point dryer and coated with Pt/Pd and then images taken. FIGS. 6C, 6D to 6E, display images of

*P. aeruginosa* cultured in phosphate-limited (DCM Pi-0.1 mM) media only, cultured in DCM Pi-0.1 mM containing 2 mM PEG20k-Pi20 and cultured in DCM Pi-0.1 mM containing 2 mM ABA-PEG20k-Pi20, respectively. SEM images showed pili-like filaments in FIGS. 6C-D (shown by arrows), while in FIG. 6E, pili-like filaments disappeared when bacteria were co-incubated in the presence of ABA-PEG20k-Pi20. These finding suggest that motility appendages, key structures involved in virulence, are influenced by the composition of the two compounds [27]. Intriguingly, in the presence of ABA-PEG20k-Pi20, the surface of bacterial cells displayed a distinct rugged appearance. Although speculative, it is possible that the hydrophobic linkage BPA acts as an anchor inserting itself into the alkyl chain region of bacterial membrane thus firmly attaching the ABA-PEG20k-Pi20 polymer to the bacterial cell surface. In this way, amphiphilic block copolymer like ABA-PEG20k-Pi20 may be more advantageous as bacterial surface coating agents and hence more protective in vivo. Further biophysical experiments are in progress to detail the interactions between phosphorylated block copolymer and bacterial membranes.

Linear phosphorylated block copolymers with a defined ABA structure were synthesized de novo and their anti-virulence activity verified by biological analyses using *P aeruginosa* as a test pathogen. See the schematic illustrated in FIG. 7. Results indicated that all phosphorylated polymers prevented phosphate signaling in *P. aeruginosa*, confirming that they can serve as phosphate delivering molecules. In vivo, using *C. elegans* killing assay, ABA-PEG20k-Pi20 appeared to be most protective compound when compared to ABA-PEG-Pis with a lower molecular weight and PEG-Pi polymers without the hydrophobic core. Scanning electron microscopy analysis demonstrated that in the presence of the ABA-PEG20k-Pi20 structure, bacterial cell surfaces displayed distinct characteristics, a finding that may explain its enhance activity in vivo. The ability to vary the hydrophobic moiety and the length of PEG spacer while controlling the functionalization of the outer block, synthesis of this ABA tri-block copolymer represents a versatile platform for anti-virulence applications of this design against highly lethal and drug resistant pathogens.

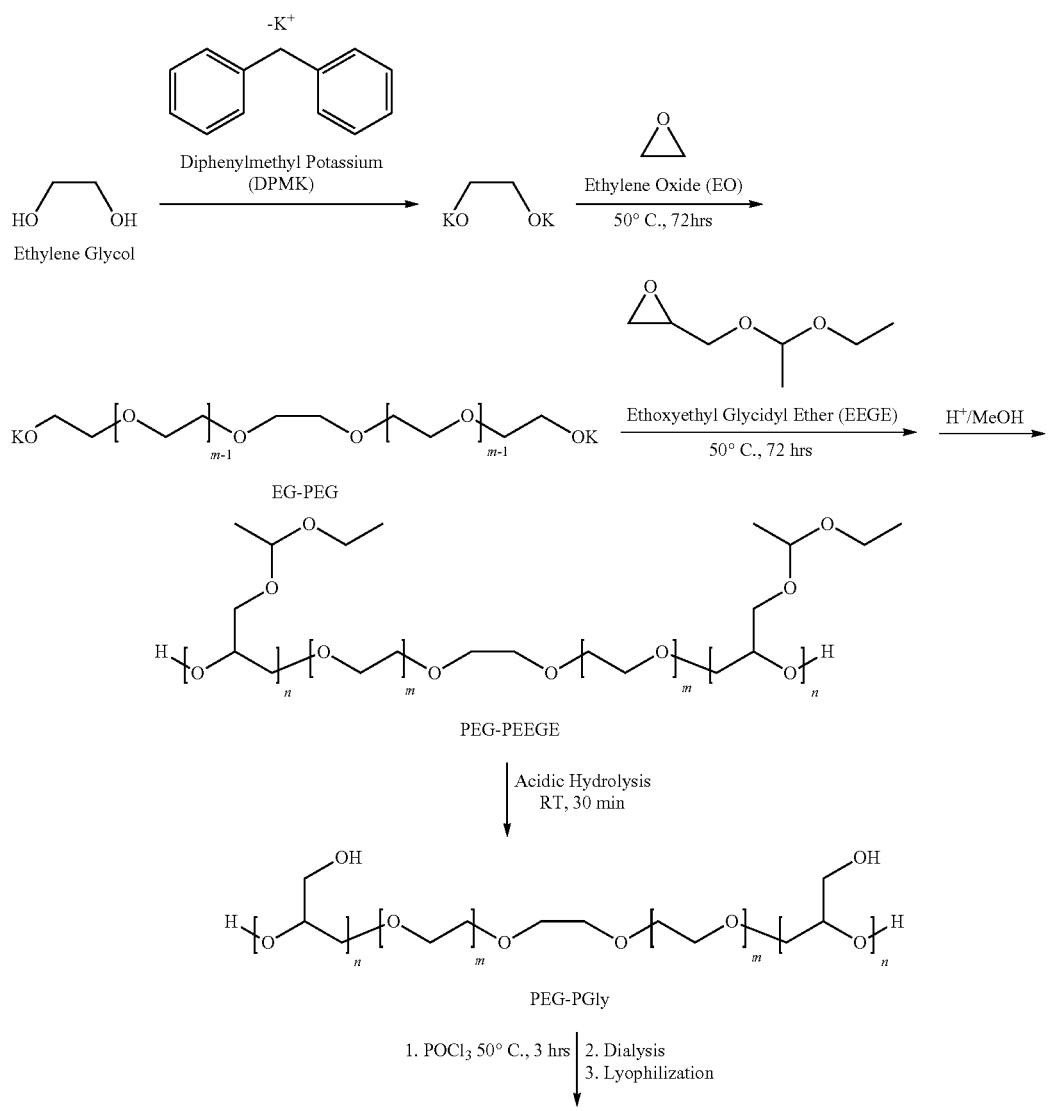

Scheme 2. Synthetic strategy of PEG-Pi block copolymers.

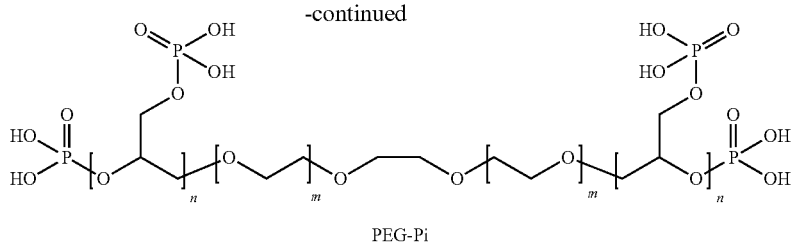

PEG-Pi

TABLE 2

Molecular characterization of PEG-based block copolymer without hydrophobic core.

| | | $M_n{}^a$ (kDa) GPC | $Đ_b$ | $N_{phosphate}{}^e$ |
|---|---|---|---|---|
| PEG-PEEGE | PEG20k-E18 | 36.5 | 1.04 | |
| PEG-PGly | PEG20k-G20 | 31.6 | 1.09 | |
| PEG-Pi | PEG20k-Pi20 | 26.2 | 1.09 | 19.8 ± 0.3 |

Nomenclature of the polymers: For PEG20k-E18/PEG20k-G20/PEG20k-Pi20, 20k is the designed molecular weight of PEG block, E18 means the designed repeating units of EEGE block is 18, G20 means the designed repeating units of Glycerol is 20, after hydrolysis of EEGE block, Pi20 means the designed repeating units of phosphorylated Glycerol block is 20.
a: PEG-PEEGE and PEG-PGly samples were measured in THF against PS standards; PEG-Pi was measured in 0.1M NaNO₃ against PEO standards.
b: Measured by GPC.
c: $N_{phosphate}$ of PEG-Pi was determined by phosphoric acid titration experiments.
e: $N_{phosphate} = N_{hydroxyl}$, assume the degree of phosphorylation reached 100% based on the fact that number-average molecular weights of Pi-ABA-PEG samples from GPC corresponded well with that from NMR results.

Example 6

The role of activated plasminogen (PLG) in anastomotic leak. To demonstrate the role of activated plasminogen (PLG) in anastomotic leak, a microbe-mediated disorder, fluorogenic PLG activity and collagenase assays were performed in the presence of collagenolytic *E. faecalis* (E44), in the presence or absence of PLG, the presence or absence of its activator urokinase, and the presence or absence of its inhibitor tranexamic acid (TXA). Co-incubation of E44 with murine macrophages (RAW267.3) was performed for studies involving conditioned media. Twenty-week-old male C57BL/6 mice underwent the validated model of E44-induced AL that includes preoperative antibiotics to defaunate the colon, surgical transection and anastomosis of the colon and introduction of E44 in 10% glycerol to the surgical site via rectal enema on postoperative day 1. The mice were treated with 0.75 mg/kg TXA or vehicle control via rectal enema on postoperative days 1, 2 and 3. Anastomotic healing was assessed blindly using a validated anastomotic healing score (AHS): 0=uncomplicated healing, 1=flimsy adhesions, 2=dense adhesions, 3=abscess, and 4=gross anastomotic disruption. AL was defined as AHS 3 or above.

Figure 13:
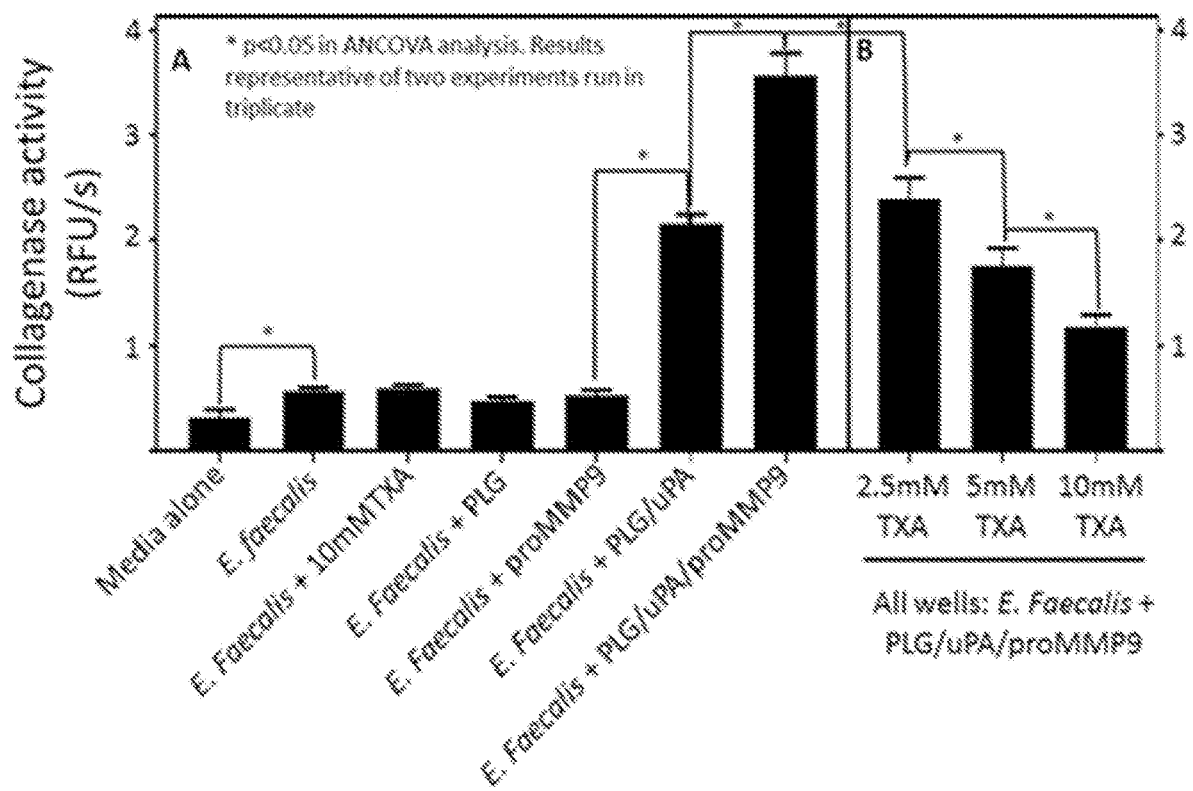
FIG. 13. *E. faecalis* that cause AL in vivo utilize plasminogen and MMP9 synergistically to degrade collagen in vitro. This process is competitively inhibited with TXA. Fluorescently tagged type IV collagen-degrading activity by collagenolytic *E. faecalis* E44 in the presence of various tissue proteases. Results were re-demonstrated with Type I collagen. A) The addition of PLG and its endogenous activator urokinase (uPA) significantly increased collagen degradation. This effect was further amplified in the presence of proMMP9. B) E44 collagen degradation with PLG, uPA and MMP9 was inhibited in a concentration-dependent manner by tranexamic acid.
Figure 14:
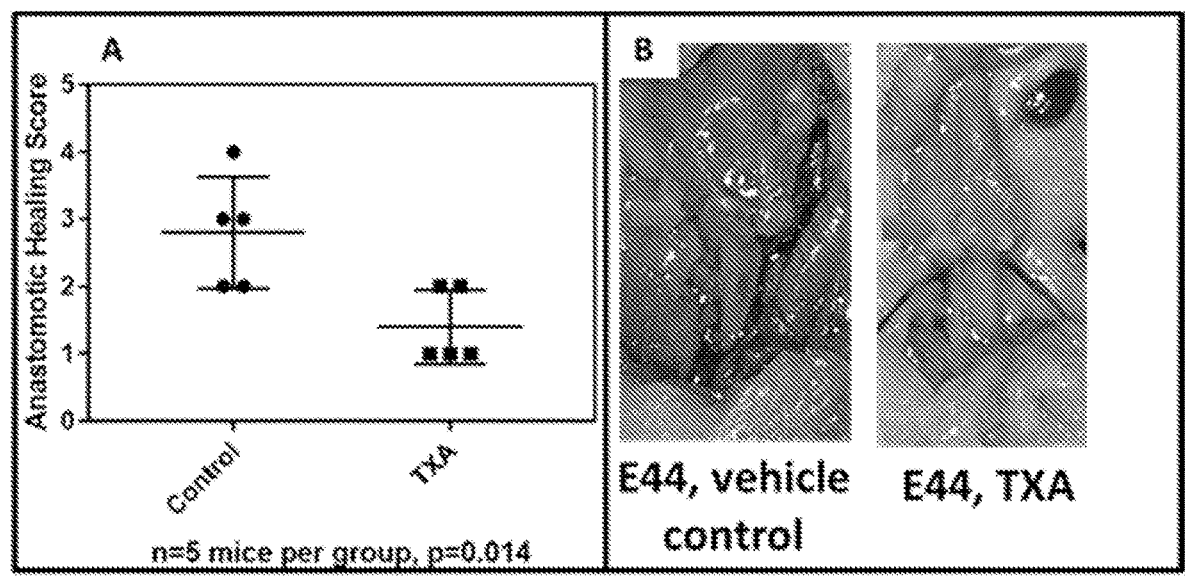
FIG. 14. Tranexamic acid prevents pathogen-induced anastomotic leak in vivo. A) Summary data of anastomotic healing scores (AHS) of 5 mice in each treatment group. Mean AHS was 2.8 in the vehicle group compared to 1.4 in the TXA group (p=0.014, Student's t-test). Mice were scored on postoperative day 8 after colorectal anastomosis followed by introduction of collagenolytic *E. faecalis* and either TXA 0.75 mg/kg or vehicle control to the surgical site via rectal enema.. B) Representative photographs of the mouse colon on postoperative day 8. The control mouse in the left panel demonstrates a dilated proximal colon, significant local inflammation and gross disruption of the anastomosis (AHS 4). The mouse that received TXA suffered only flimsy adhesions to the surgical site (AHS 1) but retained colonic function with no signs of leak.

The results showed that E44 alone activated PLG in a concentration-dependent fashion (reaction velocity increased by 0.32 RFUs per E44-colony-forming unit, $R^2=0.99$). E44 synergistically activated PLG and proMMP9, i.e., pro-matrix metalloproteinase 9 (also referred to as pro-matrix metallopeptidase 9), demonstrating amplified collagen degradation in the presence of both PLG and proMMP9 (FIG. 13A). When macrophages were plated with E44, a direct correlation was observed between PLG activity and multiplicity of infection (MOI) (without E44 36.9±2.9 AU; MOI2 40.6±3.5; MOI10 80.9±3.6, p<0.01). Subsequently, collagenolytic activity was increased in a MOI-dependent fashion (no E44 28.8±1.2 AU; MOI 10 35.8±1.4 p<0.01). Each process was inhibited by TXA in a concentration-dependent fashion (FIG. 13B). In the model of E44-induced AL, 5 mice per group received TXA or vehicle control. All mice survived until sacrifice on postoperative day 8. Overall healing (AHS) was significantly superior in the group that received TXA compared to vehicle control (FIG. 14).

This disclosure provides the first report of PLG activation in *E. faecalis*. The pathogenic strain E44 also induces PLG activation and collagen degradation in macrophages, the most abundant inflammatory cell in the colonic submucosa. TXA competitively inhibits this process in vitro and rescues pathogen-mediated AL in vivo. The data disclosed herein indicate that the molecular pathogenesis of anastomotic leak involves microbial activation of PLG, which drives an iterative loop of proteolytic activation with MMP9, amplifying collagenolytic activity to supraphysiologic levels. That this process can be suppressed by TXA establishes a therapeutic role for this inexpensive and FDA-approved agent to high risk patients scheduled or undergoing anastomotic surgery.

Example 7

Collagenolytic activity of *E. faecalis*. Experiments employed an *E. faecalis* strain (E44) with a collagenolytic, tissue-destructive phenotype that was isolated from leaking anastomotic tissues in mice [33]. The strain was tested for its ability to cleave collagen types I and IV, the subtypes critical for anastomotic integrity, both in the presence and absence of host extracellular matrix proteases. A synergistic effect was observed between E44, PLG and MMP9 (FIG. 15A,B) and collagen degradation was inhibited by TXA, which prevents activation of PLG but not MMP9 (FIG. 15C). These data indicate that PLG activation plays a critical role in the synergistic degradation of collagen by *E. faecalis* and host extracellular matrix proteases. PLG is mainly produced in the liver and diffuses into colonic tissue at low micromolar concentrations while tissue MMP, present in nanomolar concentrations, is mainly derived from resident macrophages. RAW 267.4 murine macrophages are co-incubated with E44, reasoning that bacteria and macrophages regularly co-interact in healing gut tissue. Macrophages at baseline bound PLG on the cell surface receptor alpha enolase (ENO1), where it was cleaved and activated by macrophage-secreted urokinase (uPA). The expectation was that *E. faecalis* would increase PLG binding and activation by macrophages. To confirm the expectation, naïve macrophages were stimulated with conditioned media from E44 overnight culture. Experiments demonstrated that conditioned medium of E44 (secretome, E44s) profoundly stimulated macrophages to activate PLG. This effect was inhibited by TXA (FIG. 16A). *E. faecalis* secreted factors that likely stimulated secretion of plasminogen activators in macrophages and/or ENO1 receptor expression on the cell surface.

It was then tested whether macrophage collagen degradation activity is enhanced by stimulation with *E. faecalis*. Conditions from the above experiment (RAW/E44 s) with naïve RAW macrophages were used. PLG and MMP9 were included in the reaction. Degradation of collagen was enhanced by secreted factors produced during the co-interaction of RAW and E44s. This effect again was attenuated by TXA (FIG. 16B). Thus, TXA was identified as an inhibitor of pathogen-mediated supraphysiologic collagen degradation in all studies. Finally, to investigate the mechanism of PLG activation by *E. faecalis*, a parent collagenolytic strain isolated from a patient with AL (V583) was used, along with its mutant derivative (DDGelE/Spr) with secretory collagenolytic factors serine protease (Spr) and gelatinase (GelE) genetically removed. The acellular secretome of each strain was assessed for PLG activation, which was significantly higher in the parent than the mutant strain (5.93±0.48 AU versus 4.00±0.35 AU, p<0.01). The results of this experiment indicated that either GelE or Spr, both expressed under surgical conditions, had a partial role in *E. faecalis*-mediated PLG activation. The data demonstrate that *E. faecalis*-induced collagen degradation is directly dependent on the availability of PLG and involves the availability of active MMP9. In the pathogen-induced AL model, *E. faecalis* is a disordering agent that drives an interactive loop of collagen degradation, triggered by PLG over-activation. In the model, activation of plasminogen by bacteria sets up iterative activation of MMP9 and further downstream PLG activation leading to a burst of excessive collagen degradation. Attenuating this cycle with TXA prevents supraphysiologic collagen degradation and, thus, pathogen-mediated AL. The convergence of multiple pathogens on PLG and its interconnectedness to MMP9 during wound healing, forms the basis of some of the methods disclosed herein that address the supraphysiological levels of PLG activated by pathogenic bacteria in AL and the pharmacological suppression of that activation with plasminogen inhibitors such as TXA and aminocaproic acid (e.g., F-aminocaproic acid) to treat or reduce the risk of AL. The data provide critical evidence of the essential role of the PLG system in AL. This finding provides a targetable mechanism underlying this common and lethal condition.

Example 8

Pathogen-mediated PLG activity in anastomotic tissues. An experiment was designed and to quantify and localize pathogen-mediated PLG activity in anastomotic tissues of mice with AL. Pathogens that cause AL activate PLG to supraphysiologic levels, leading to excessive collagen degradation at the anastomotic site. To date, the binding and activation of PLG has been considered a characteristic of pathogenic bacteria, not commensal strains [42]. Tissue PLG and MMP9 are both regularly exposed to bacteria during injury and each activates the other in an iterative loop pathway. Poor healing has been shown within multiple tissue sites when PLG is supraphysiologically activated (i.e., leading to excess collagen degradation) [43]. The following experiments demonstrate that pathogen-mediated PLG activation is a critical step in the collagenolytic cascade that precedes AL. The experiments demonstrate that, in vitro and in vivo, PLG is excessively activated at the surgical site in the established model of anastomotic leak, compared to its physiologic activity when healing proceeds normally.

The surgical procedure used in these experiments conformed to the validated model of physiologically healing colorectal anastomosis and pathogen-mediated leak (8), in which mice are subjected to transection of the colon and anastomosis. Collagenolytic *E. faecalis* (E44) (to induce AL) or vehicle control (for healing anastomoses) are introduced to the anastomosis via enema during surgery and on postoperative day 1 (POD1). Mice are sacrificed for tissue analysis at various time points (i.e., POD 2, 4, 6).

A mechanistic evaluation of pathogen-mediated collagen degradation is undertaken both in vitro and ex vivo: PLG activity in various tissue homogenates and culture conditions is assessed through fluorogenic plasmin generation assays, using a validated method [44]. Similarly, fluorescein-tagged gelatin, type 1 collagen, and type 4 collagen degradation assays are used. Various strains of microbes known to cause AL are tested, beginning with Efaecalis and including Pseudomonads and *Serratia*. Controls include non-collagenolytic strains that do not cause AL. From these studies, it is expected that collagenolytic strains will induce significantly more PLG activity and collagen degradation across the conditions examined. Specific MMP9 activity will be assessed with a commercially available fluorogenic assay. Using the above methods, each step in the iterative system is probed kinetically.

Plasminogen activation in vivo is assessed using 8-week-old C57BL/6 mice that are injected intraperitoneally with FITC-labeled PLG and subjected to the model of physiologically healing anastomosis, or pathogen-mediated AL. PLG binding at the surgical site is quantified using endpoint frozen sectioning at various time points after surgical anastomosis. Immunofluorescence of anastomotic tissue is performed in axial sections for co-localization of macrophages and detection of the PLG receptor alpha enolase (ENO1). Anastomotic tissue is homogenized using a 3D bead homogenizer and normalized for weight. ELISA for PLG and its activators, along with plasmin generation assays are performed on homogenized tissue and plasma is collected at the time of sacrifice. Longitudinal and quantitative monitoring of the resolution of fibrin deposition within the wound functions as a surrogate marker for local PLG activity using a fibrin-targeted peptide [45](FTP11-Cy5.5) via fluorescence on the Maestro In-Vivo Fluorescence System. In vitro kinetics of PLG activity may differ in the absence of its canonical substrate, fibrin clot. As such, bacterial interactions with PLG may depend on the presence of fibrin as well. Additional studies utilizing a fibrin clot created in vitro may be performed to more closely approximate in vivo kinetics. The presence of fibrin at the surgical site is a surrogate marker of PLG's fibrinolytic activity and may not directly correlate with PLG activity. Alternative assays utilizing labeled PLG and quantitative studies of PLG activity in homogenates of the tissue in question may be used.

Example 9

Figure 15:
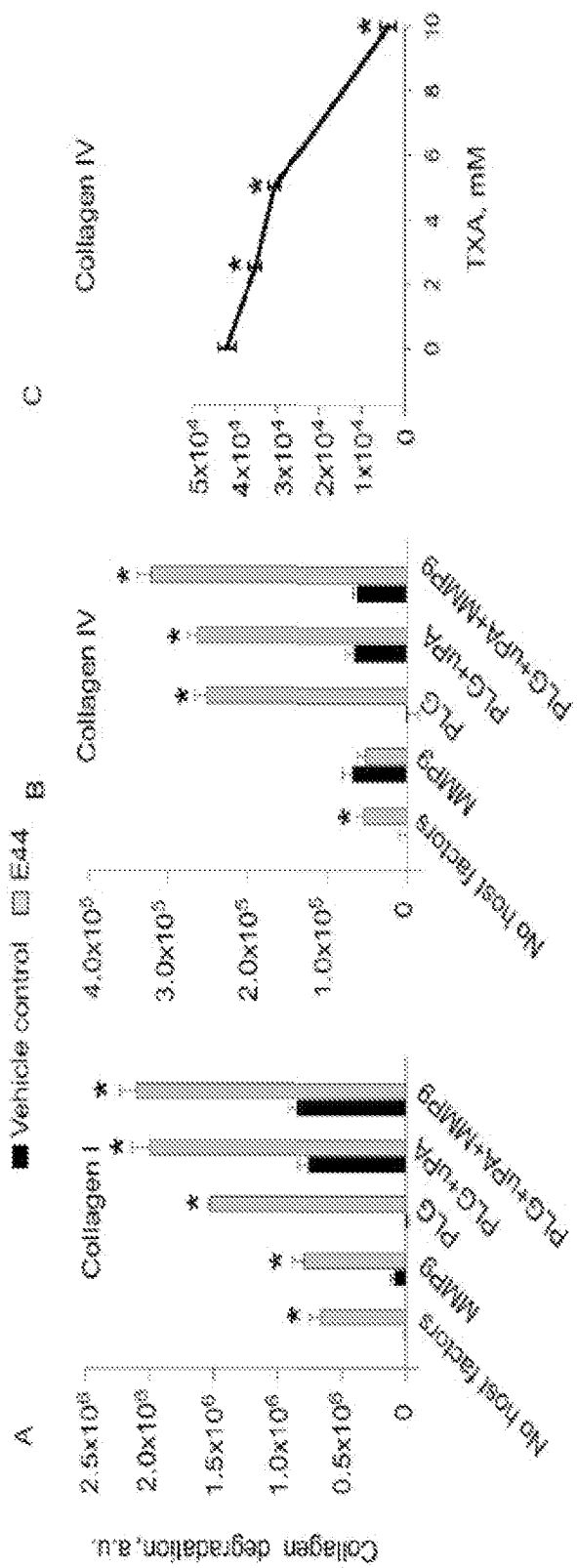
FIG. 15. Synergistic degradation of collagen by *E. faecalis* E44 and host proteases is inhibited by tranexamic acid (TXA). Collagenolytic *E. faecalis* strain E44 alone degrades fluorescently tagged collagen I (A) and IV (B) at 8 hours incubation. Degradation is greater at physiologic concentrations of PLG (250 nM) compared to physiologic levels of proMMP9 (1 nM) and enhanced with the addition of the PLG activator urokinase (uPA). *p<0.05, n=6/group. (C), The synergistic collagen IV degradation by E44+PLG+uPA+MMP9 is inhibited by TXA, a known inhibitor of PLG activation.
Figure 16:
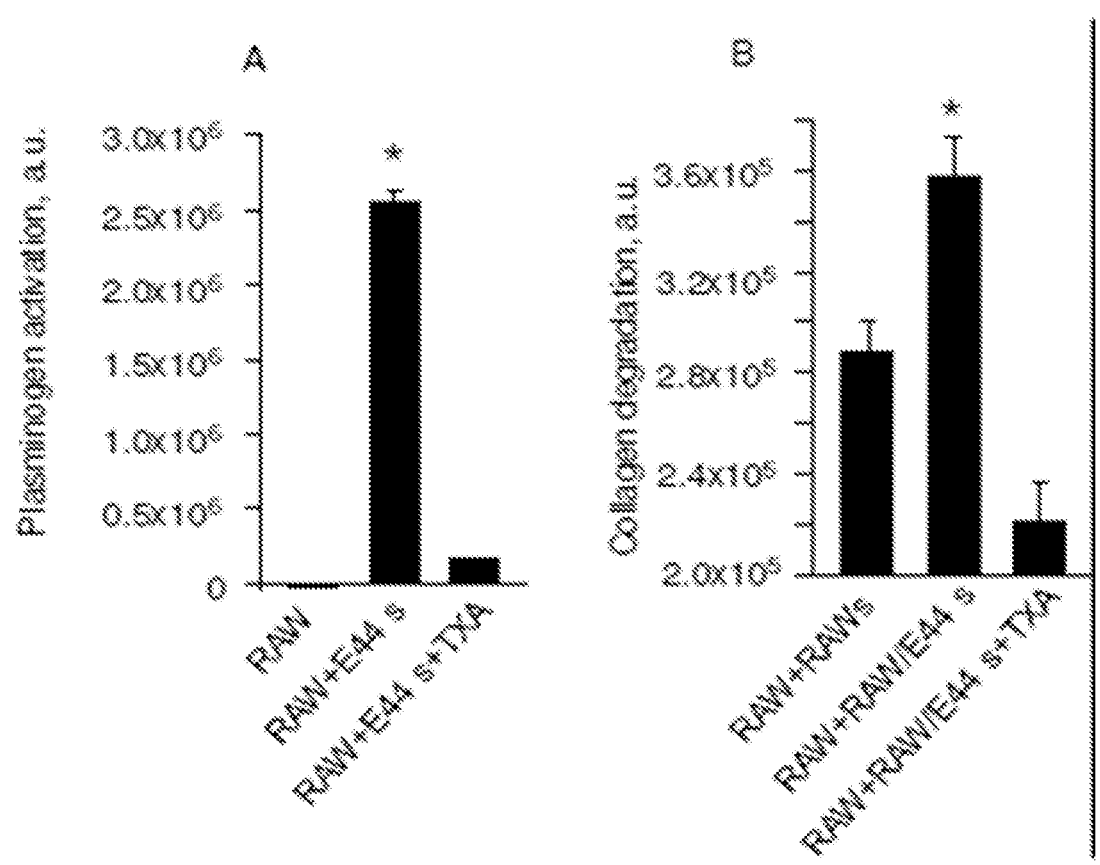
FIG. 16. TXA abrogates the stimulating effect of *E. faecalis* on the ability of macrophages to activate PLG and degrade collagen. (A), *E. faecalis* E44 was grown in TY media overnight, and cell-free conditioned media (E44s) was applied to RAW macrophages for 4 hours. PLG, 250 nm, was included in the reaction. TXA, 10 mM, was added when needed. PLG activation was measured by fluorogenic substrate cleavage. "RAW" column is naïve RAW. *p<0.05, n=6/group. (B), Conditioned media after co-interaction of macrophages with *E. faecalis* E44 (named RAW/E44s) was applied to naïve RAW macrophages for 4 hours. PLG, 250 nm, and MMP9, 1 nM, were in all reactions. TXA, 10 mM, was added when needed. "RAW+RAWs" column is naïve macrophages incubated with conditioned media of RAW macrophages (no *E. faecalis* E44). *p<0.05, n=6/group.
Figure 17:
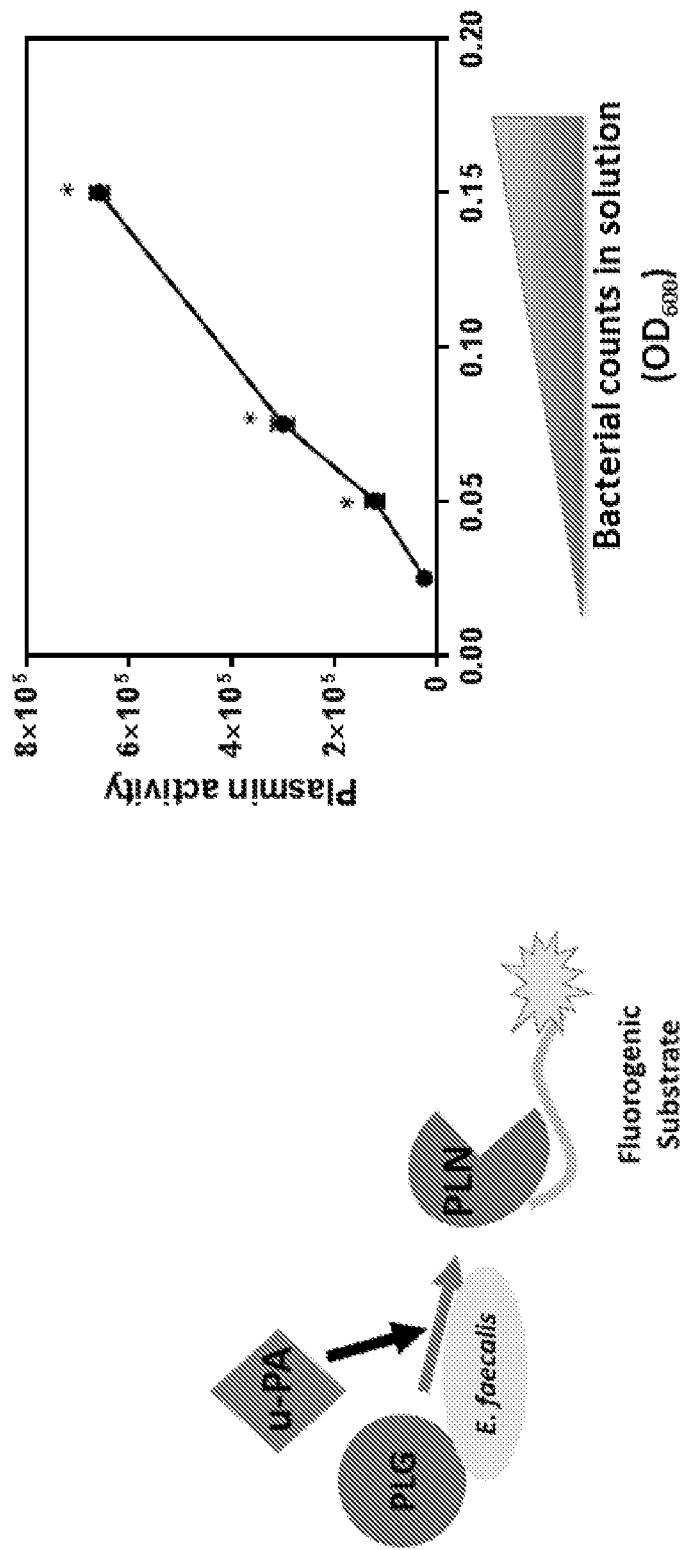
FIG. 17. Plasminogen activation in *E. faecalis*, known to cause leak, has not been described. To test the ability to activate plasminogen, the inventors used a fluorogenic assay with a substrate specific to active plasmin, in the presence of its activator urokinase, shown here as uPA. When *E. faecalis* was added, the results showed that plasmin activity was directly related to the amount of *Enterococcus* in solution, which indicated that the *E. faecalis* E44 strain was capable of activation.

Mechanism of PLG inhibition. Experiments are also contemplated to investigate the mechanism of PLG inhibition as a therapy for the treatment or reduction of risk in developing AL, for example in mice. TXA prevents AL in mice through inhibition of PLG and collagen degradation. The PLG system has been partially targeted with various degrees of success for treatment of systemic bacterial infections, but direct local inhibition of bacterial PLG activation to reduce virulence has not been attempted. Data disclosed herein demonstrate that TXA inhibits bacterial collagen degradation in the presence of PLG (FIGS. 15, 16). The pathogen-mediated iterative loop of collagen degradation depends on microbial activation of PLG and the cyclic downstream activation of MMP9. TXA inhibition of PLG intervenes in the loop involving MMP9 and prevent AL in vivo. The pharmacokinetics of systemically delivered TXA in human surgery are well described and dosing protocols will be matched as closely as possible to clinical conditions [46].

The experimental design involves FITC-labeled PLG being used to assess cell surface binding of PLG by pathogens and stimulated macrophages using fluorescent microscopy. TXA and antibodies to known bacterial PLG receptors are used to inhibit binding and further elucidate the mechanism of PLG activation in collagenolytic E. faecalis. Functional tissue invasion is assessed by exploring the ability of TXA to reduce the relative invasiveness of leak-causing E. faecalis strains, with the ability being measured by examining the ability of the strains to penetrate model extracellular matrix (Matrigel and collagen I) and by assessing their killing effect on C. elegans [45]. E44 and other strains known to cause AL will undergo penetration assays in the presence and absence of PLG and TXA, with the expectation that penetration will be enhanced in the presence of PLG and diminished by TXA.

Prevention of AL using TXA: Models of healing anastomosis and pathogen-mediated leak, as described above with slight modification, are used to examine the prevention of AL by TXA. Four groups of mice undergo surgery, n=10 per group. Two groups undergo physiologically healing anastomoses with either TXA or vehicle control, given via rectal enema at various time points. Two groups undergo the model of pathogen-mediated AL with E44, along with either TXA or vehicle control. Mice are observed clinically and sacrificed if moribund. All mice are sacrificed for necropsy on POD10 (post-operative day 10). Primary outcomes are overall survival, and both gross and histologic analyses of anastomotic tissue for evidence of leak and collagen content. Anastomoses are evaluated using a validated Anastomotic Healing Score (AHS) [47]. Temporary ablation of PLG activity using TXA is expected to lead to improved survival and decreased AHS, indicating improved anastomotic healing. Pharmacologic knock-down of PLG antigen is accomplished using antisense oligonucleotides (ASO) specific for PLG (Ionis pharmaceuticals, CA, USA) as previously described [48]. Three groups (high dose PLG-ASO, low dose PLG-ASO and control nonspecific ASO), of mice undergo the pathogen-mediated AL protocol with E44, with 5 mice per group. Survival and anastomotic healing is assessed as described above. Knock-down of PLG expression is confirmed with plasma ELISA. It is expected that systemic ablation of PLG expression will rescue AL in a fashion similar to pharmacologic inhibition with TXA.

Example 10

E. faecalis binds PLG and increases its activity in solution with urokinase (uPA). Data disclosed herein shows that supraphysiologic activation of the host PLG system is an important step in the pathogenesis of pathogen-mediated anastomotic leak (AL), and that tranexamic acid (TXA), applied locally to an anastomosis, can act as an anti-infective agent by dampening pathogen-mediated plasminogen (PLG) activation and downstream collagen degradation.

Figure 31:
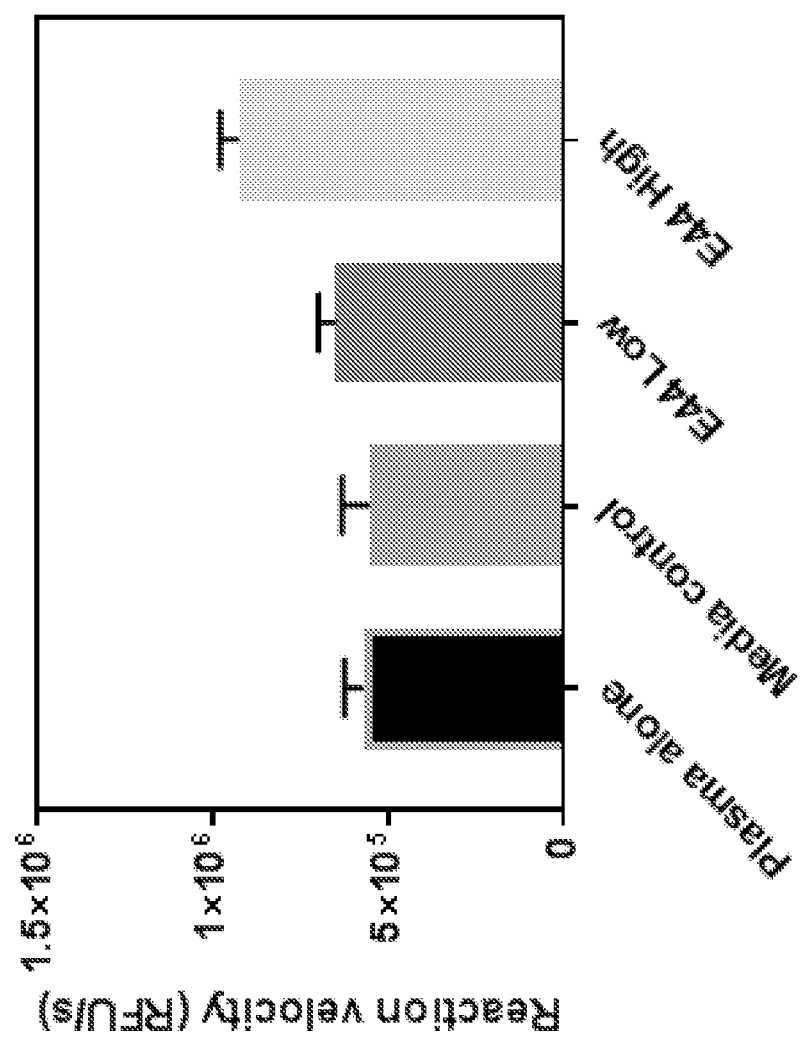
FIG. 31. Microbial pathogens activate PLG in a dose-dependent manner. Plasminogen activation assays were performed by measuring the rate of plasmin generation in mouse plasma, in bacterial growth media, in the presence of a low concentration of collagenolytic *E. faecalis*, and in the presence of a high concentration of collagenolytic *E. faecalis*.
Figure 32:
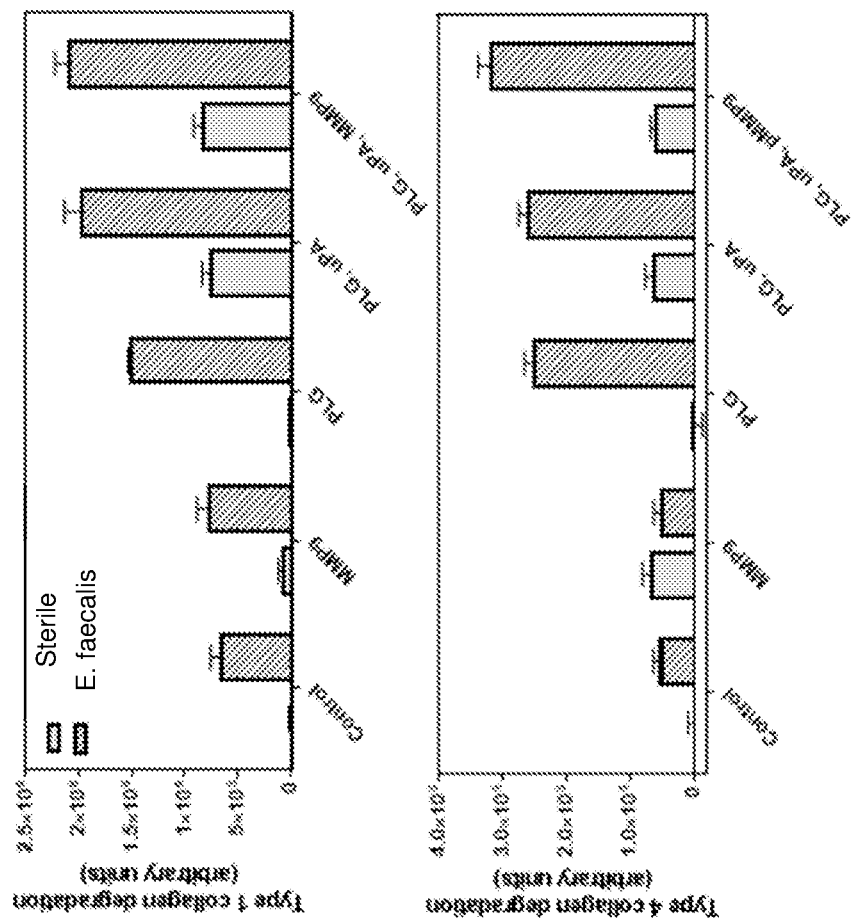
FIG. 32. Effect of collagenolytic *E. faecalis* E44 on degradation of various collagen types in various backgrounds.
Figure 33:
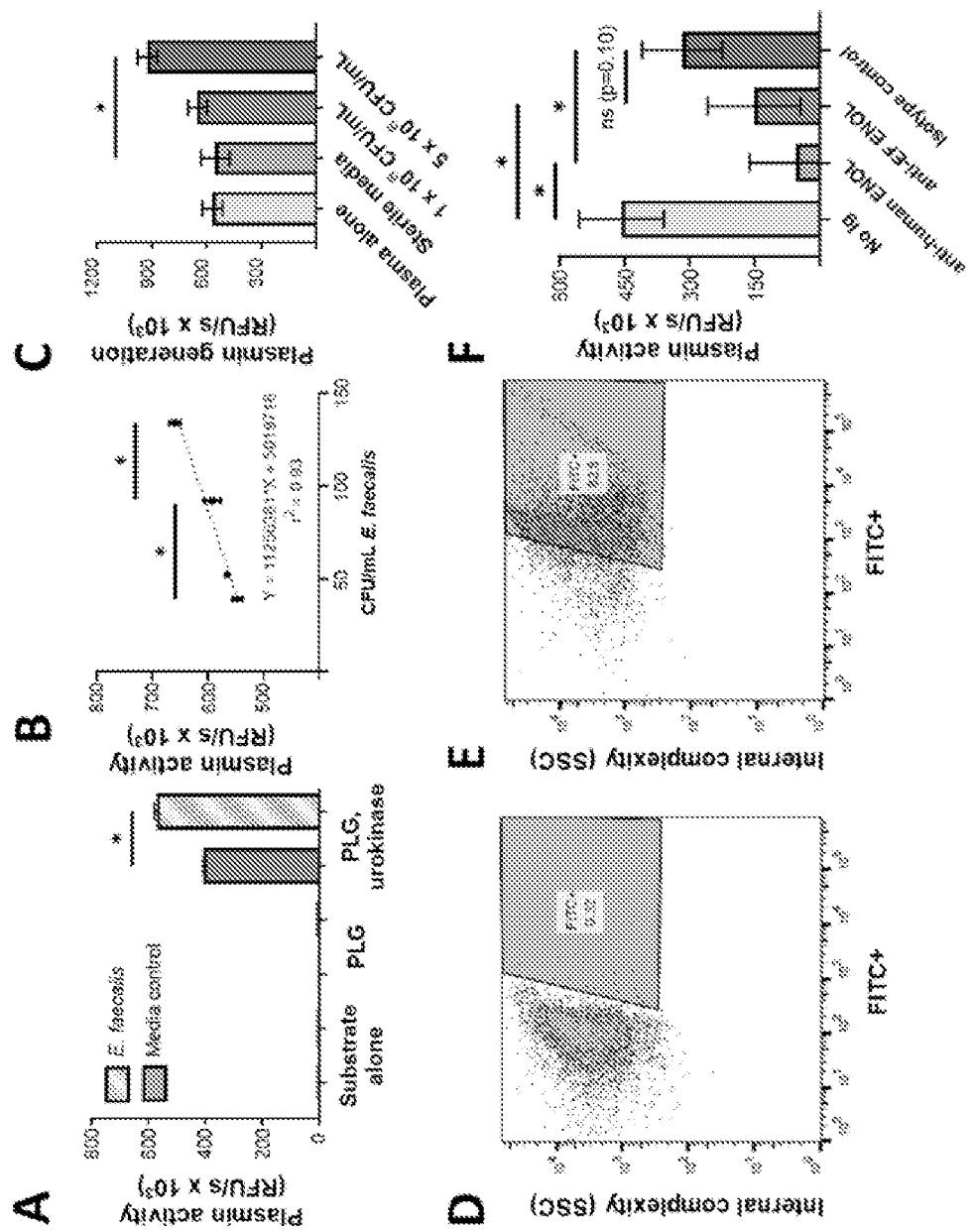
FIG. 33. *E. faecalis* bind human PLG and contribute to urokinase-based activation. A) Plasmin activity assay in media with or without the addition of PLG and uPA. *E. faecalis* significantly increased plasmin activity compared to sterile media control (* $p<0.01$, ANCOVA). B) Plasmin activity assay in the presence of uPA and increasing concentrations of *E. faecalis* demonstrates a direct relationship between bacterial concentration and plasmin activity (* $p<0.01$, ANCOVA). C) Plasmin generation assay in human platelet-poor plasma demonstrates *E. faecalis* increases plasmin generation in the presence of a full complement of human activators and inhibitors (* $p<0.01$, ANCOVA). D) Flow cytometric analysis of 10,000 *E. faecalis* cells exhibiting minimal autofluorescence. E) After incubation with FITC-labeled PLG and washing, 82.6% of *E. faecalis* demonstrated surface-bound FITC-PLG. F) Plasmin activity assay demonstrating that anti-human enolase and a polyclonal antibody raised in rabbits against a C-terminal peptide of enterococcal enolase inhibit plasmin activation (* $p<0.05$, ANCOVA). Error bars indicate means±SD. All data are representative of three separate experiments, each run in triplicate.
Figure 41:
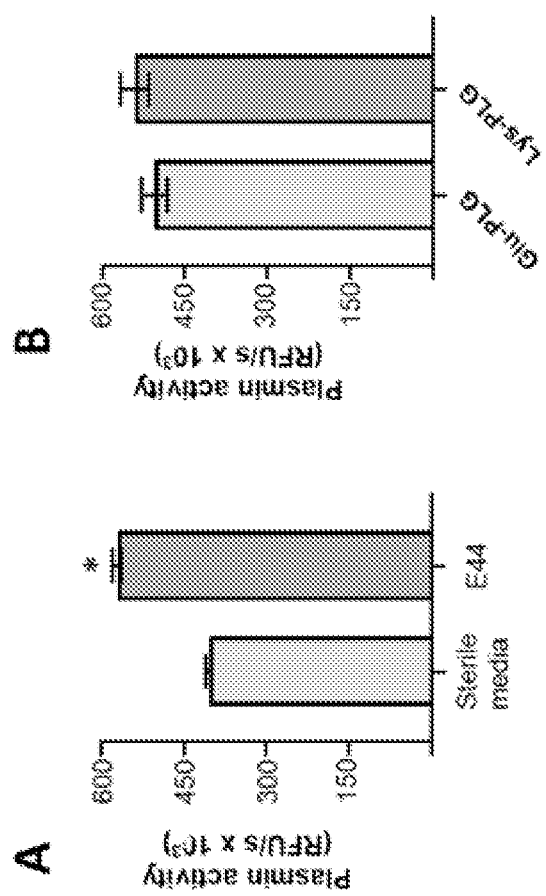
FIG. 41. Enterococcal strain and plasminogen isotype-specific results for PLG activation. A) All strains of *E. faecalis* tested activate PLG in the presence of active uPA (*p<0.05 ANCOVA). B) V583 *E. faecalis* in the presence of active uPA activates the glu and lys-isoforms of human PLG with similar avidity. Error bars indicate means±SD. All data are representative of three separate experiments, each run in triplicate.

The collagenolytic E. faecalis strain V583, known to have a causative role in AL in rodents, was tested to determine if it could activate PLG using fluorogenic kinetic assays. Results demonstrated that plasmin activity was observed only when uPA was co-incubated with PLG and E. faecalis V583 (FIG. 33A) indicating that PLG activation by E. faecalis depends on surface binding and cleavage-based activation by uPA, as described in other PLG-activating species(24'). E. faecalis induced PLG activation in the presence of u-PA in a concentration-dependent manner (FIG. 33B). These results were reproduced using another collagenolytic strain of E. faecalis, E44 (FIG. 41A). To determine whether V583 induces plasmin activity in the presence of native PLG activators and inhibitors, plasma-based plasmin generation assays were performed. The addition of low concentrations of V583 to human platelet-poor plasma induced significantly more plasmin activity than controls (FIG. 33C and FIG. 31). Differential binding and activation of the glu- and lys-isoforms of human PLG has been reported in some bacterial species (25'). V583 in a purified system with uPA activated both the glu- and lys-isoforms of PLG with similar avidity (FIG. 41B).

Figure 18:
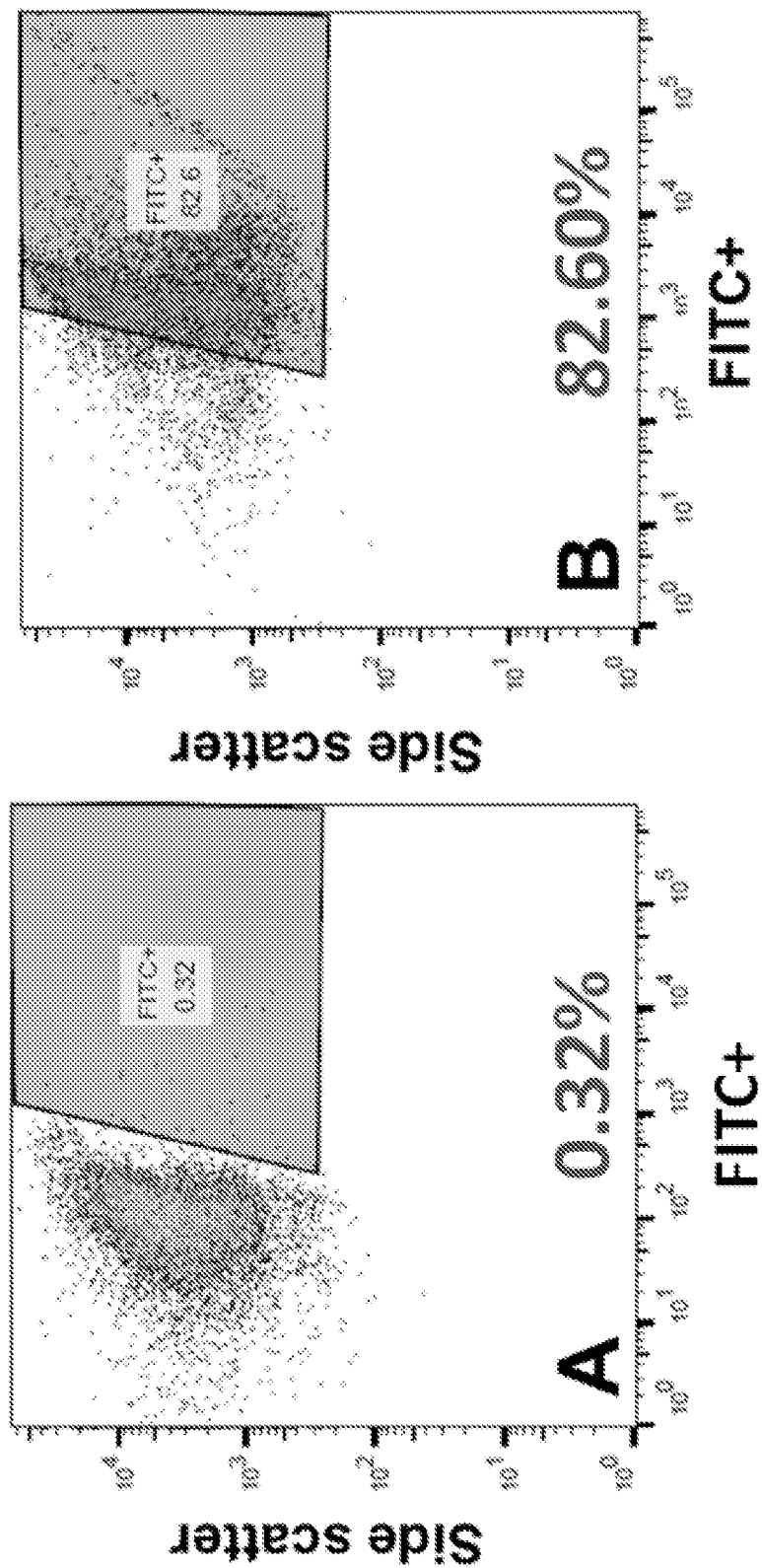
FIG. 18. Flow cytometry was used to localize PLG to the cell surface, the normal site of activation in other bacterial species. In the figure, bacteria inside the grey area are bound to fluorescently-labeled PLG, while bacteria outside the grey area are not bound. A) shows the negative control without labeled PLG. B) illustrates that 83% of cells had surface-bound tagged PLG after a one-hour incubation.
Figure 24:
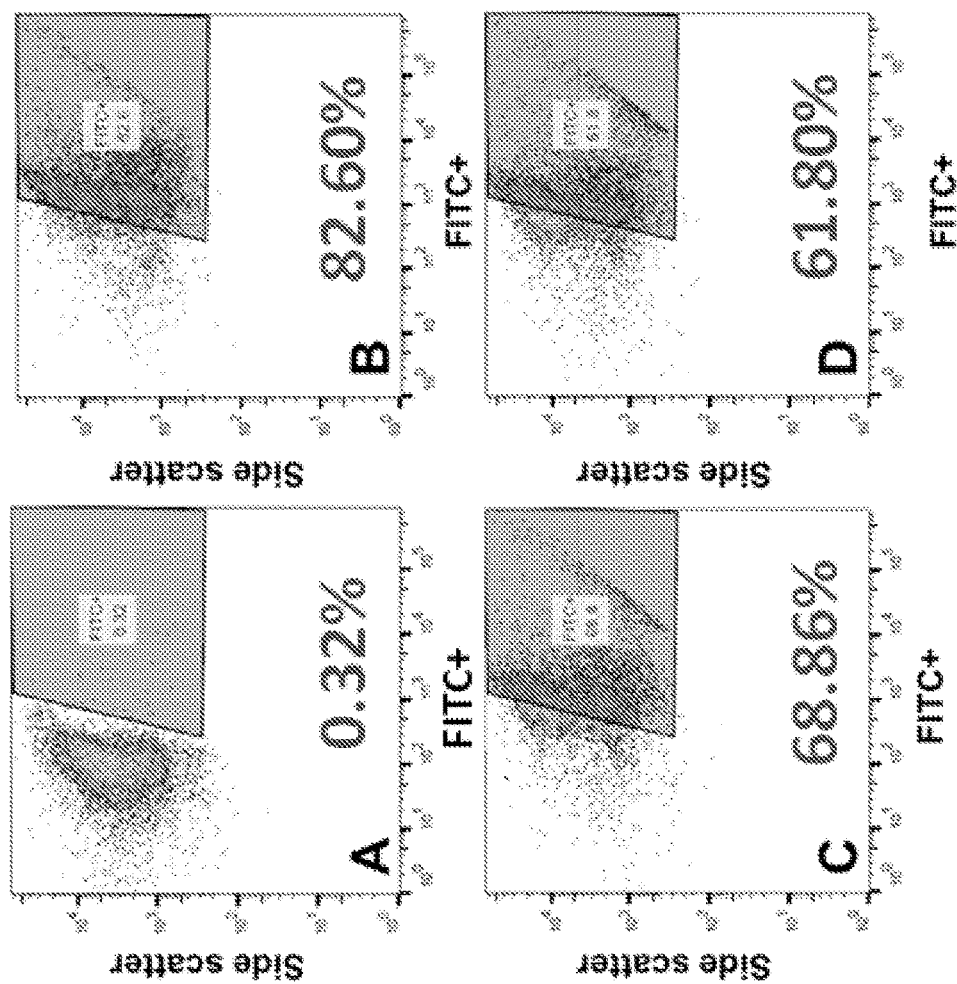
FIG. 24. *E. faecalis* binds PLG on the cell surface. Flow cytometry of fluorescein-labeled PLG bound to *E. faecalis*. The enclosed region demonstrates bacteria bound to fluorescently-labeled PLG. Panel A represents the negative control of unlabeled PLG. Panel B represents the population of bacteria incubated with labeled-PLG after 1 hour incubation. Panels C and D reflect the binding of labeled PLG to *E. faecalis* in the presence of tranexamic acid (TXA) functioning as an inhibitor of PLG activation.
Figure 25:
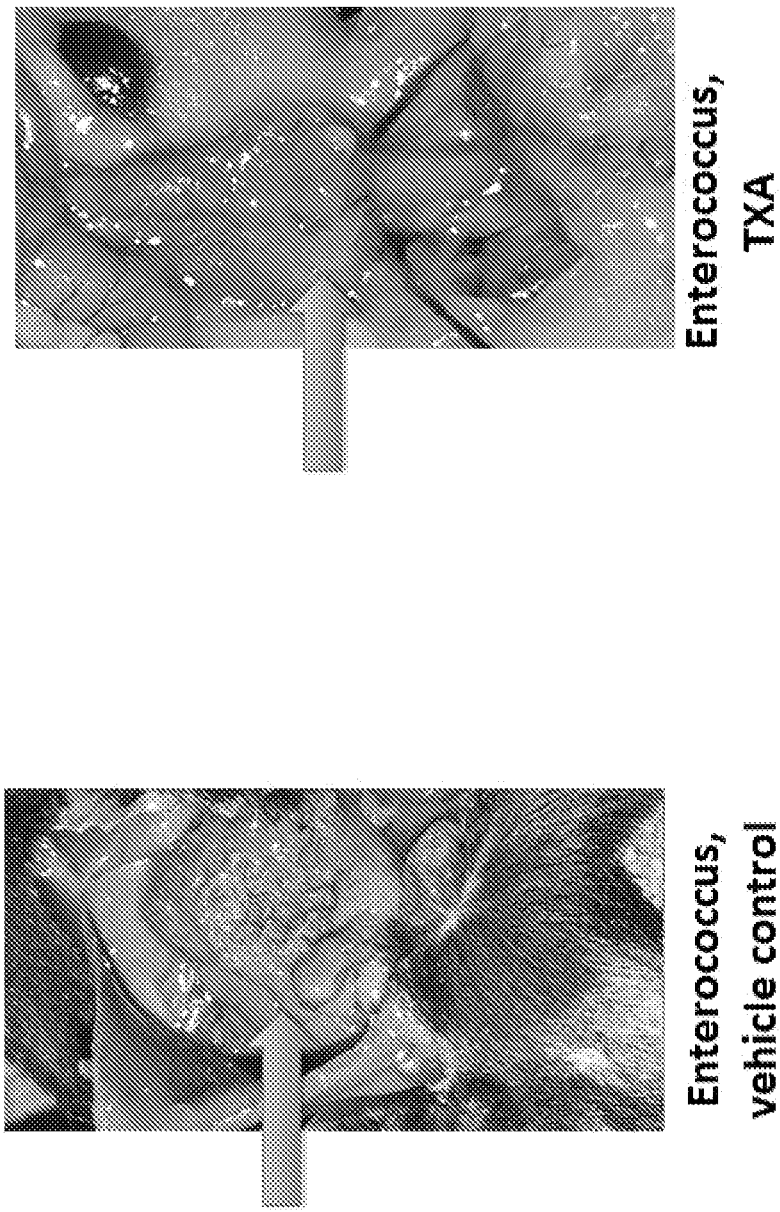
FIG. 25. Effect of PLG inhibitor in vivo. After exposure to antibiotics, mice underwent a colon transection and surgical anastomosis followed by introduction of collagenolytic *E. faecalis* V583 via rectal enema with either TXA or vehicle control on post-operative day (POD) 1,2 and 3. Images of the colonic anastomosis from POD 8. The left panel shows an image of the colonic anastomotic site in a mouse that received *E. faecalis* in vehicle control, which reveals a dilated proximal colon with gross disruption of the anastomosis. The right panel shows an image of the colonic anastomotic site in a mouse that received *E. faecalis* in a TXA solution, which reveals flimsy adhesions to the surgical site but a patent anastomosis and functional colon.

Next, the ability of E. faecalis to bind PLG on the cell surface was tested. V583 was incubated for one hour with FITC-labeled PLG, followed by centrifugation, washing with phosphate-buffered saline (PBS), and re-suspension. Flow cytometry was used to quantify surface-bound FITC-PLG. V583 incubated with non-labeled PLG demonstrated negligible autofluorescence (FIG. 33D, FIG. 24, and FIG. 18). V583 incubated with FITC-PLG demonstrated a significant right shift in fluorescence and 82.6% cellular binding positivity (FIG. 33E, FIG. 24 and FIG. 18).

PLG was known to bind to poly-lysine motifs at the C-terminus of surface exposed a-enolase on bacterial and eukaryotic cells, followed by uPA-based activation (26'). a-enolase is expressed on the surface of E. faecalis (20'). The inventors therefore attempted to inhibit PLG activation using either rabbit anti-human a-enolase IgG specific to the C-terminus, or rabbit IgG raised against a 16-amino-acid peptide from the C-terminus of E. faecalis. Immunologic cross-reactivity between human and bacterial enolase due to the highly conserved structure of this essential metabolic enzyme (27') allowed the inventors to use both antibodies. Nonspecific rabbit IgG was a negative control. Anti-human enolase significantly decreased plasmin activity compared to isotype controls, and anti-enterococcal enolase decreased plasmin activity compared to the absence of antibody, and approached but did not reach a statistically significant difference from isotype controls (FIG. 33F).

Example 11

Figure 34:
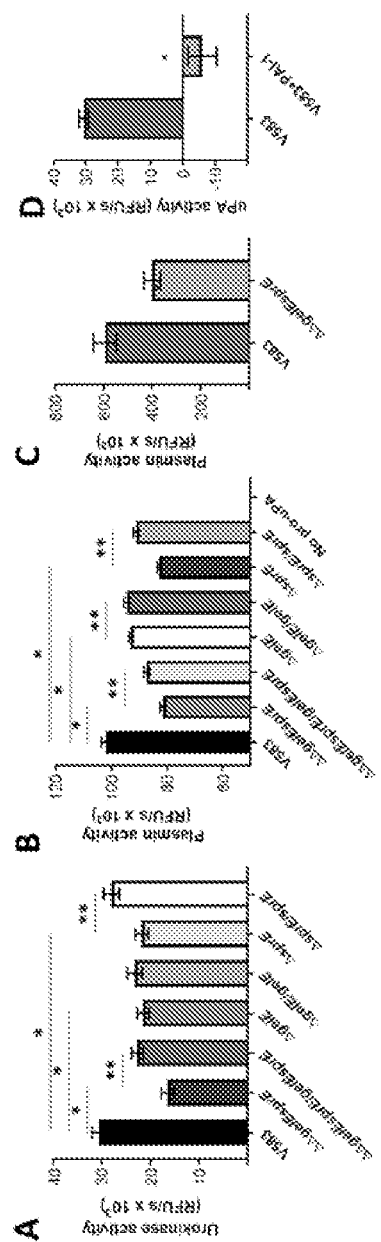
FIG. 34. Activation of pro-urokinase and PLG by *E. faecalis* depends partially on gelatinase E and serine protease. A) pro-uPA activation assay in the presence of live *E. faecalis* V583. uPA activity was diminished in mutants deficient in GelE (ΔgelE), SprE (ΔsprE), or both (ΔΔgelEsprE) and recovered in complemented mutants ΔsprE/sprE and ΔΔgelEsprE/gelEsprE (* $p<0.05$ for deficient mutants versus parent strain. ** $p<0.05$ for complemented mutants versus deficient strain, ANCOVA). B) Downstream PLG activation in the presence of live *E. faecalis* and pro-uPA depends partially on expression of GelE and SprE as demonstrated in both knockout and complemented strains (* $p<0.05$ for deficient mutants versus parent strain; ** $p<0.05$ for complemented mutants versus deficient strain, ANCOVA). C) PLG activation in the presence of pro-uPA and *E. faecalis* V583 or ΔΔgelEsprE when using acellular filtered conditioned media, confirming a dependence on secreted factors (* $p<0.05$, ANCOVA). D) pro-uPA activation by V583 was completely inhibited by the human uPA inhibitor PAI-1 (* $p<0.01$, ANCOVA). Error bars indicate means±SD. All data are representative of three separate experiments, each run in triplicate.

Activation of the PLG system by E. faecalis depends on expression of Gelatinase E (GelE) and Serine protease (SprE). uPA, the principal activator of PLG in tissue, is secreted by inflammatory cells as the pro-uPA zymogen, which is cleaved by host or bacterial proteases to its more active two-chain form(24'). The parent strain V583 and mutants deficient in the proteolytic virulence factors GelE and SprE were incubated with pro-uPA. uPA-specific activity was measured kinetically with a fluorogenic assay. V583 demonstrated the ability to cleave and activate pro-uPA. This ability was diminished in strains that did not express the virulence factors GelE (ΔgelE) or SprE (ΔsprE). The largest effect was observed in double-mutant strains deficient in both factors (ΔΔgelEsprE). The ability to activate pro-uPA was restored when these factors were reintroduced in plasmid-based complemented mutants (ΔgelE/gelE, ΔsprE/sprE, ΔΔgelEsprE/gelEsprE) (FIG. 34A). Consequently, downstream PLG activation in the presence of pro-uPA depended on expression of both GelE and SprE (FIG. 34B). To confirm this effect was mediated by secreted factors, the results were replicated in conditioned media (CM) from the stationary phase of growth for both V583 and ΔΔgelEsprE. CM from ΔΔgelEsprE compared to V583 had a reduced ability to activate PLG in the presence of pro-uPA (FIG. 34C). Activation of pro-uPA by V583 was fully inhibited by the human inhibitor plasminogen activator inhibitor 1 (PAI-1) provided in equimolar quantities to uPA (FIG. 34D).

Example 12

Impact of E. faecalis on inflammatory cell PLG activation. Macrophages are the most abundant inflammatory cells in the colon and aggregate at sites of injury such as an anastomosis (28'). Under normal healing conditions, an early burst of inflammatory-mediated proteolytic activity occurs in response to tissue injury, followed closely by inhibitory regulation (29'). Therefore, the inventors investigated the impact of E. faecalis on PLG activation in murine monocyte/macrophage cell lines using kinetic plasmin activity assays in the presence of added PLG and uPA.

Figure 35:
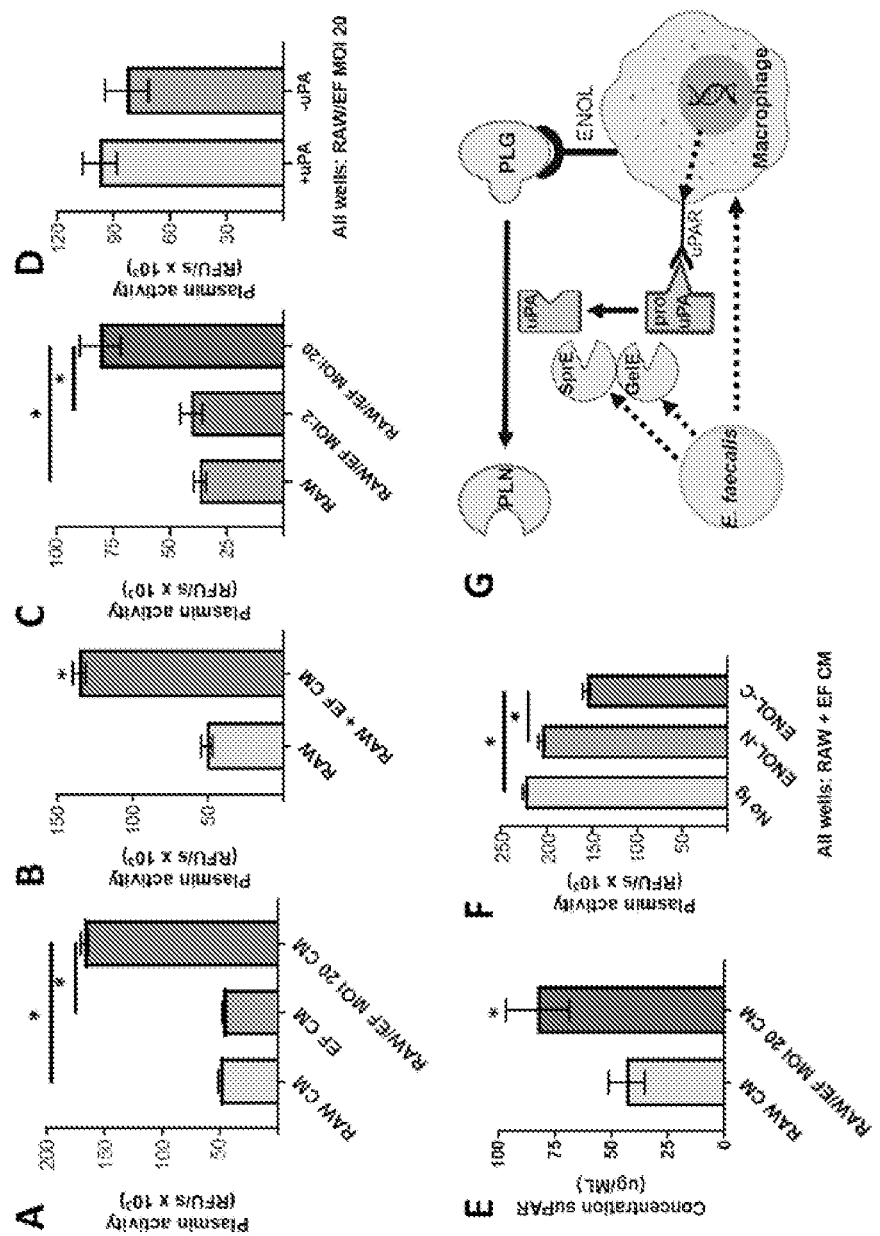
FIG. 35. *E. faecalis* induces PLG activation and suPAR release in murine macrophages. A) Conditioned media from RAW 267.4 macrophages co-cultured with live *E. faecalis* V583 activates PLG to a greater degree than CM from either cell line cultured alone in this plasmin activity assay with added PLG and uPA (* p<0.01, ANCOVA). B) Filtered bacterial CM added to the culture medium of live RAW 267.4 macrophages induced significantly more PLG activation than controls treated with sterile non-conditioned media after a 6-hour incubation (* p<0.01, ANCOVA). C) RAW 267.4 macrophages co-cultured with live V583 activate significantly more PLG at a multiplicity of infection of 20 than macrophages cultured alone or with V583 at a MOI of 2 (* p<0.01, ANCOVA). D) Incubated with V583 at a MOI of 20, plasmin activation by RAW 267.4 macrophages was not significantly enhanced by supplemental 5 nM uPA, indicating that macrophages exposed to bacteria secrete endogenous PLG activators. E) Incubation of RAW 267.4 cells with live V583 induces expression and release of the soluble urokinase receptor (suPAR) as measured by ELISA of conditioned media (* p<0.05, Student's t-test). F) Plasmin activity assay of macrophages stimulated with V583 CM followed by incubation with antibodies directed against the N- and C-terminals of human alpha-enolase. Incubation with antibodies directed at the C-terminus significantly diminished PLG activation (* p<0.01, ANCOVA). G) Schematic of a proposed mechanism for increased plasmin generation by macrophages after exposure to *E. faecalis*, independent of intrinsic PLG system activation by *E. faecalis*. Error bars indicate means±SD. All data are representative of three separate experiments, each run in triplicate.
Figure 42:
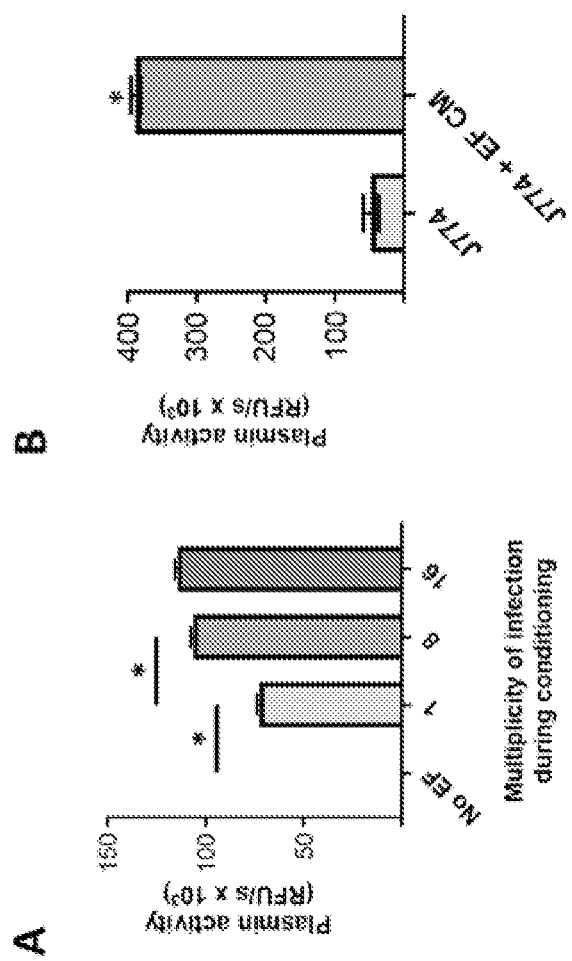
FIG. 42. *E. faecalis*-induced plasmin generation in murine monocyte-macrophages. A) Conditioned media from *E. faecalis* co-cultured with J774.2 cells, a second monocyte-macrophage cell line, stimulates PLG activation in a manner dependent on the amount of *E. faecalis* present in co-culture, and stimulation begins to plateau at a multiplicity of infection between 8 and 16 (*p<0.05 ANCOVA). B) Conditioned media from *E. faecalis* stimulates plasmin activation in live J774.2 monocyte-macrophages (*p<0.01 ANCOVA). Error bars indicate means±SD.

CM from RAW 267.4 macrophages co-cultured with V583 induced more plasmin activity than CM from either cell line cultured separately (FIG. 35A). This finding was re-demonstrated in a second murine monocyte-macrophage cell line, J774.2, and demonstrated a direct relationship with the amount of V583 present in co-culture (FIG. 42A, FIG. 31). RAW macrophages were then treated with CM from V583 and after a 6-hour incubation observed significantly more plasmin activity from treated cells than controls treated with sterile media. This finding was generalizable to J774.2 monocyte-macrophages as well (FIG. 42B). In live co-culture, RAW macrophages and V583 demonstrated increased PLG activation at a relatively low multiplicity of infection (MOI) of 20 ($10^4$ RAW 267.4 with $2\times10^5$ V583 at initial seeding); however, this effect was not observed at a lower MOI of 2 (FIG. 35C). As macrophages constitutively produce and activate pro-uPA, it was notable that when grown with V583 at a MOI of 20 and incubated with PLG, the elimination of added uPA from the reaction did not significantly decrease PLG activation (FIG. 35D).

The uPA receptor (uPAR) binds pro-uPA and facilitates cleavage to the active form and co-localization with PLG. It is expressed by stimulated macrophages, and released as a soluble form (suPAR) by active plasmin (30'). To further investigate the mechanism of E. faecalis-induced PLG activation on macrophages, ELISAs were performed to look for suPAR in CM from macrophages incubated overnight with live V583 (MOI 20) and PLG. Results showed increased levels of suPAR antigen in CM from macrophages incubated with V583 compared to sterile controls (FIG. 35E). a-enolase serves to co-localize PLG with uPAR-bound uPA on the macrophage surface (31'). RAW 267.4 macrophages stimulated by V583 CM were exposed to rabbit anti-human enolase IgG. Incubation with antibody raised against the exposed C-terminus of the receptor diminished plasmin activation, where control antibody specific to the N-terminus of alpha enolase had no effect (FIG. 35F).

Example 13

Figure 19:
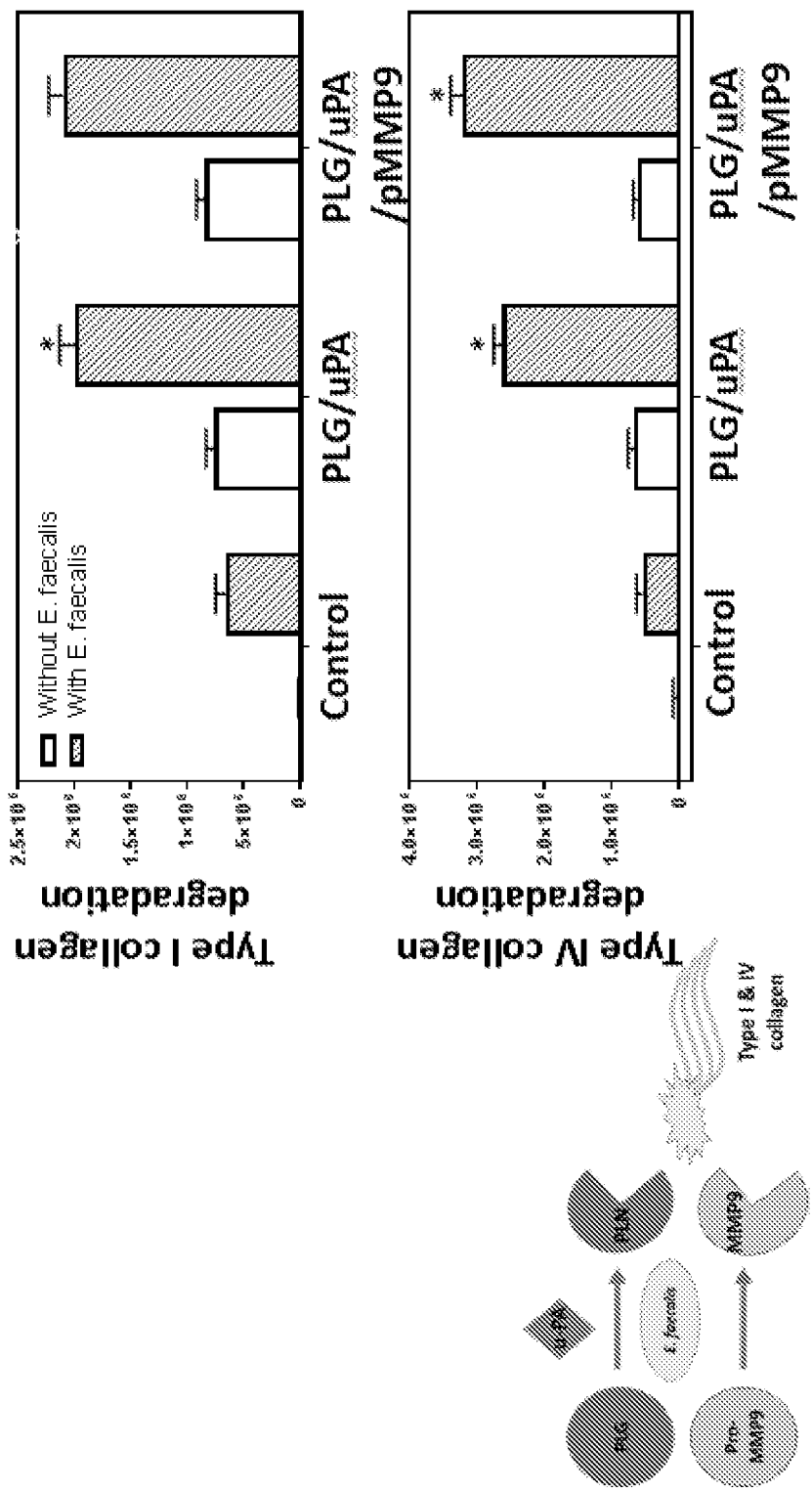
FIG. 19. *E. faecalis* causes anastomotic leak through activation of proMMP9 and collagen degradation. Knowing that plasmin itself cleaves collagen, it was expected that *E. faecalis* would also use plasminogen as a tissue-destructive virulence factor. A fluorogenic assay was used to confirm that *E. faecalis* used plasminogen in this matter with tagged types I and IV collagen. The inventors controlled for all variables in this reaction. In all conditions, *E. faecalis* alone was able to degrade Types I and IV collagen. However, in the presence of plasminogen and urokinase (uPA) at concentrations found in colonic tissue, the bacteria degraded collagen between 3 and 5 times more efficiently. In the case of type 1 collagen, Plasminogen accelerated degradation independent of MMP9. When type IV collagen was tested, a synergistic effect was observed between PLG and MMP9. These results indicate that host plasminogen enhances the tissue destructive phenotype of *E. faecalis*.
Figure 20:
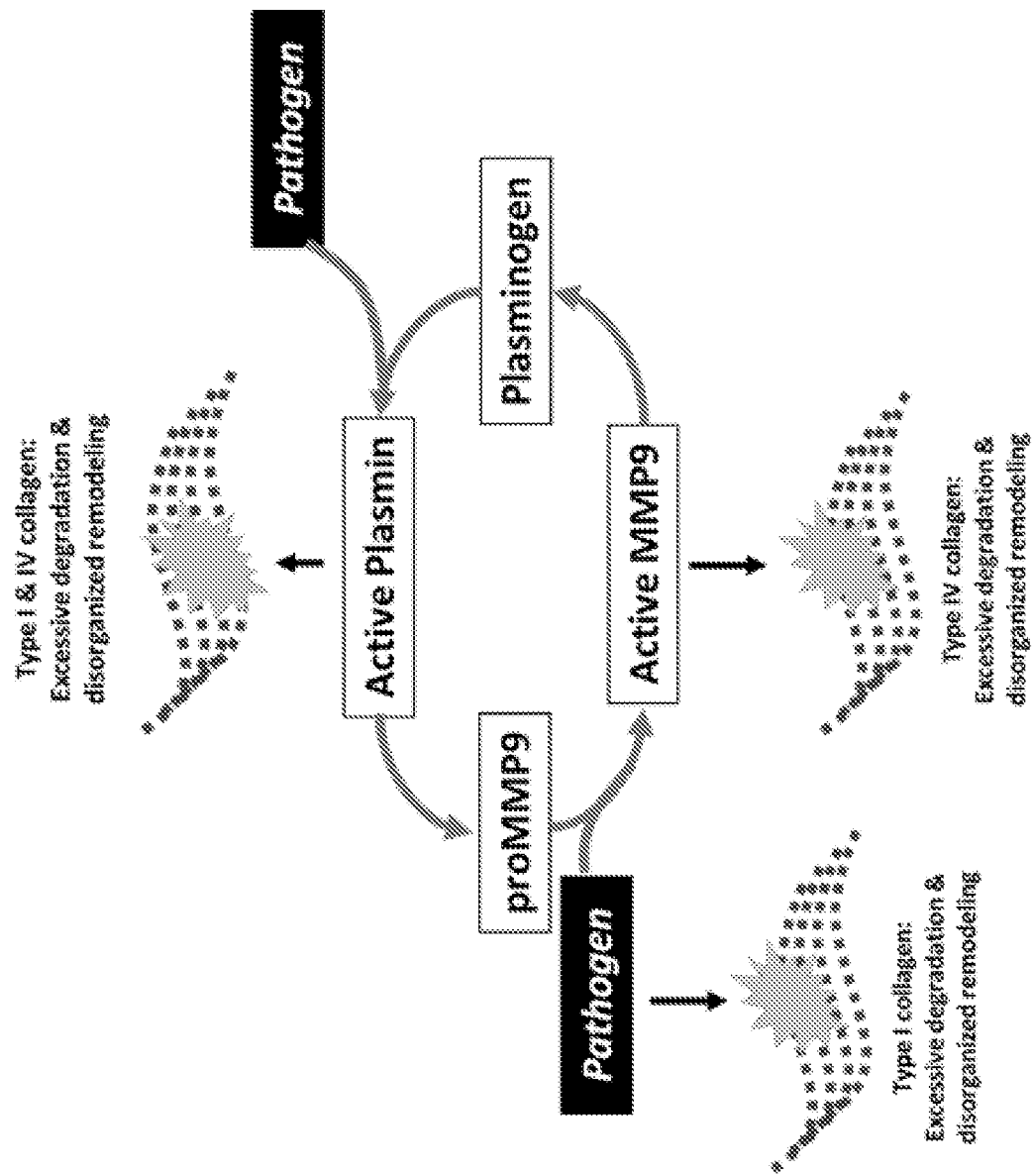
FIG. 20. A molecular model accounting for the data resulting from the experiments disclosed herein is provided, in which an iterative loop of dysregulated tissue protease activation is driven by the pathogens that cause AL, leading to excessive collagen degradation and failure of healing in a surgical anastomosis.
Figure 21:
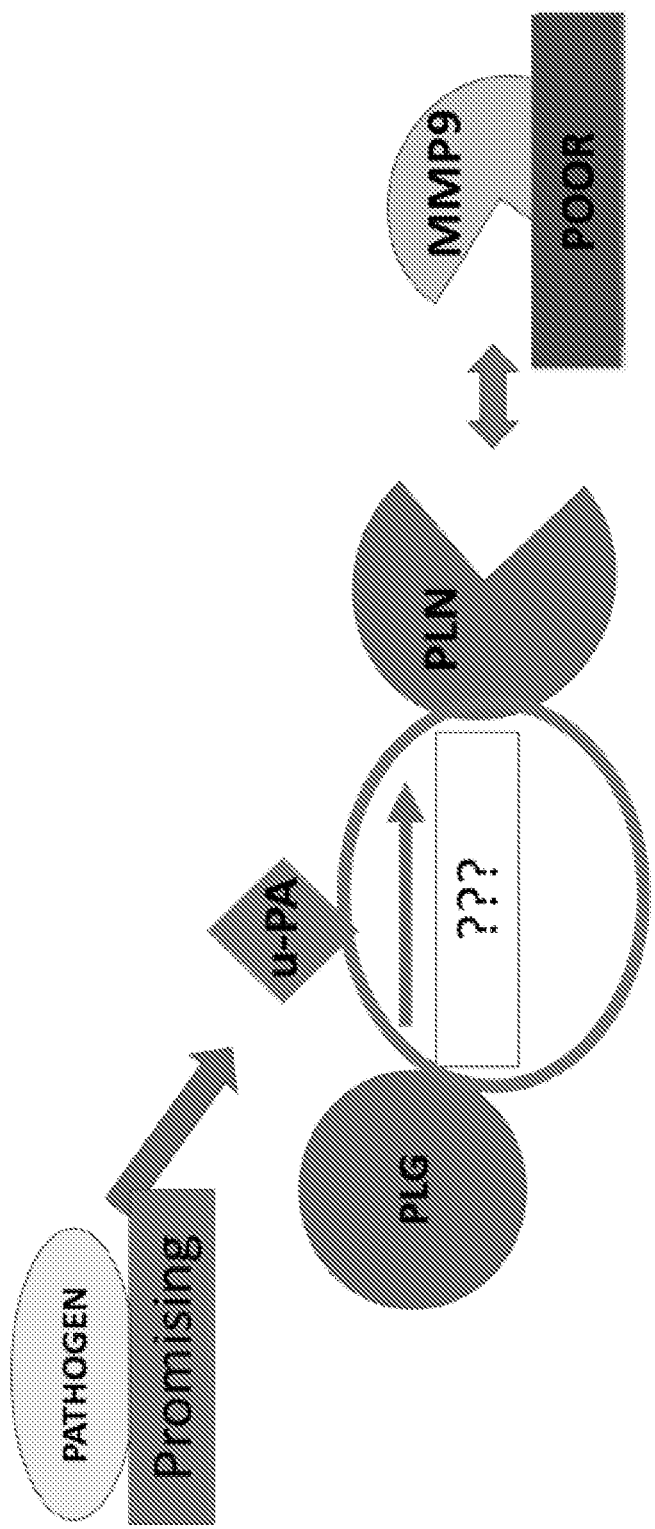
FIG. 21. *E. faecalis* causing AL in vivo uses PLG to degrade collagen in vitro, and PLG induces macrophages to perform similarly at much higher levels than they do in the absence of pathogen. A model for targeting this pathway in a cost-effective manner is presented, with a preference for controlling the pathway by controlling PLG activation rather than MMP9 activation, although either or both points in the pathway are amenable to control.
Figure 22:
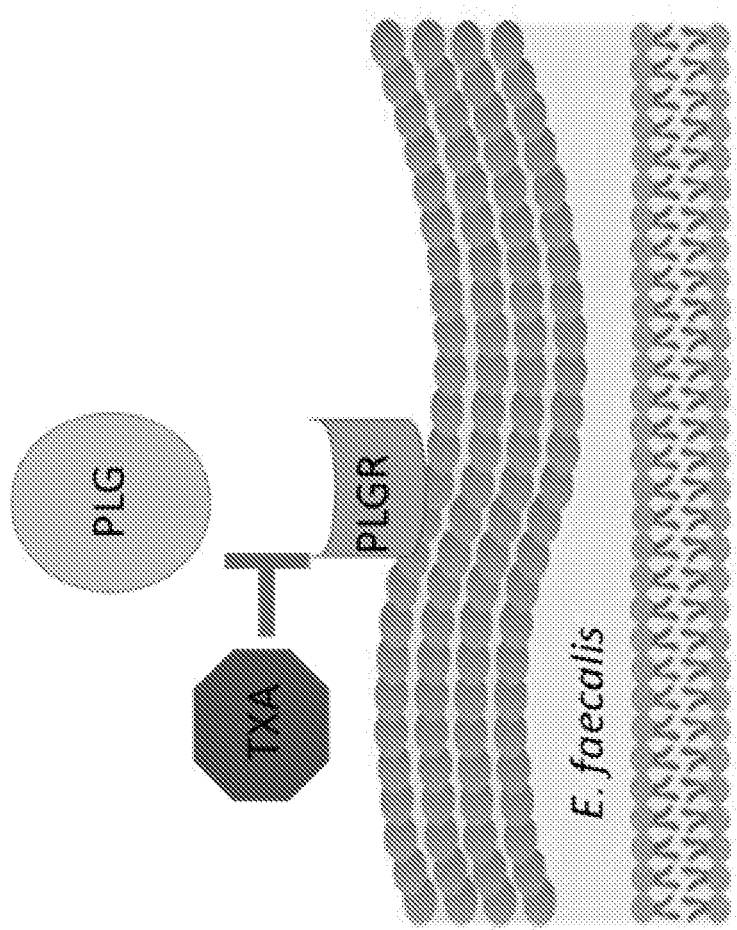
FIG. 22. A model for a method of treating or reducing the risk of developing anastomotic leak is provided wherein the therapeutic is tranexamic acid (TXA), an exemplary PLG inhibitor. TXA is inexpensive and FDA approved for use in elective surgery. TXA, like other PLG inhibitors, is used to inhibit bacterial PLG activation at the surgical site. PLG inhibitors prevent PLG from being bound and activated on the surface of microbes that would use it to degrade collagen.
Figure 36:
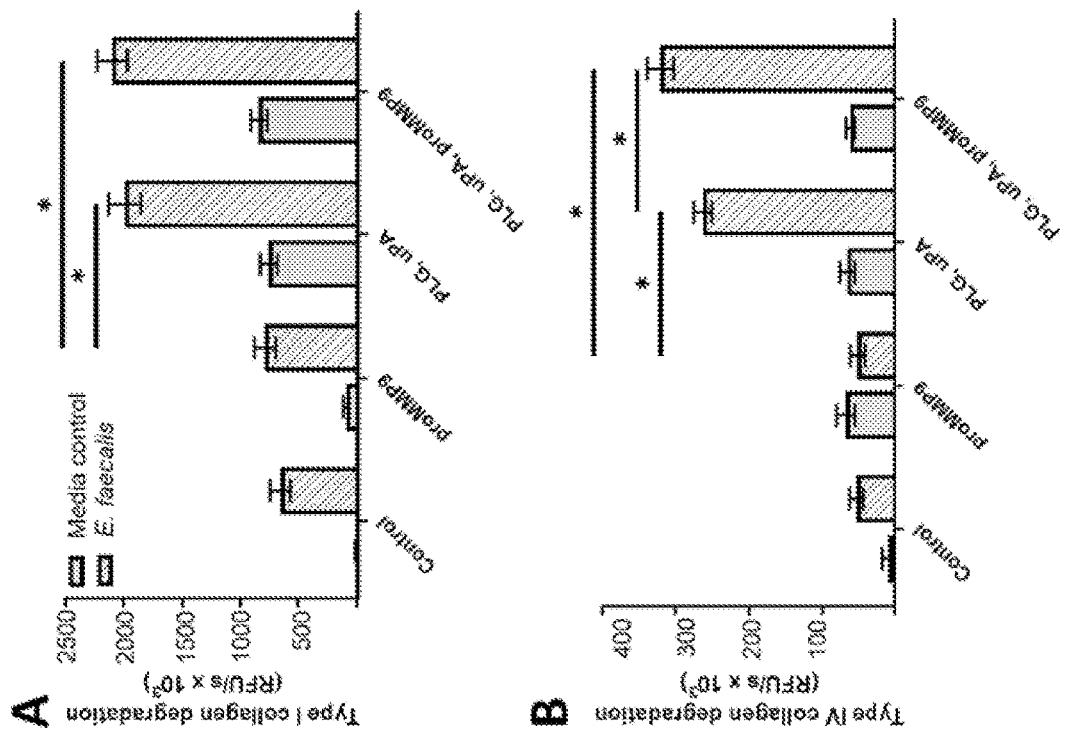
FIG. 36. In vitro collagen degradation by *E. faecalis* is enhanced by the presence of PLG and uPA. A) Collagen degradation assay demonstrating *E. faecalis* V583 alone degrades fluorescein-labeled type I collagen as expected. Significantly enhanced degradation was observed with the addition of PLG and uPA. Collagen degradation in the presence of V583, PLG and uPA exceeded the additive levels of the components of this reaction (bacteria alone plus PLG/uPA alone). The impact of additional proMMP9 to this reaction was negligible (* p<0.01, ANCOVA). B) Fluorescein-labeled type IV collagen degradation assay. Again, *E. faecalis* alone demonstrated collagenolytic activity, enhanced in the presence of PLG with uPA. In this case, the addition of pro-MMP9 induced further degradation in the presence of PLG, uPA and *E. faecalis*, whereas degradation was unchanged in this reaction under sterile conditions (* p<0.01, ANCOVA). Error bars indicate means±SD. All data are representative of three separate experiments, each run in triplicate.

Co-interaction of E. faecalis with u-PA, PLG and pro-MMP9 creates a synergistic loop leading to enhanced degradation of collagen. V583 was incubated with fluorescently labeled type I or type IV collagen, in a purified system complemented with PLG, active uPA, and pro-MMP9 at physiologic concentrations. The presence of V583 increased type I and IV collagen degradation after a 6-hour incubation. Pro-MMP9 alone did not increase bacterial collagen degradation. The presence of PLG with uPA increased degradation of both types I and IV collagen 3-fold. Collagen degradation in the presence of V583, PLG and uPA was greater than the additive activities of sterile PLG with uPA and that of V583 alone, indicating synergistic degradation when E. faecalis is exposed to PLG with uPA. Additive collagen degradation between PLG and pro-MMP9 was observed in the case of type IV but not type I collagen (FIG. 36A, B, FIG. 15 and FIG. 19).

Example 14

Figure 43:
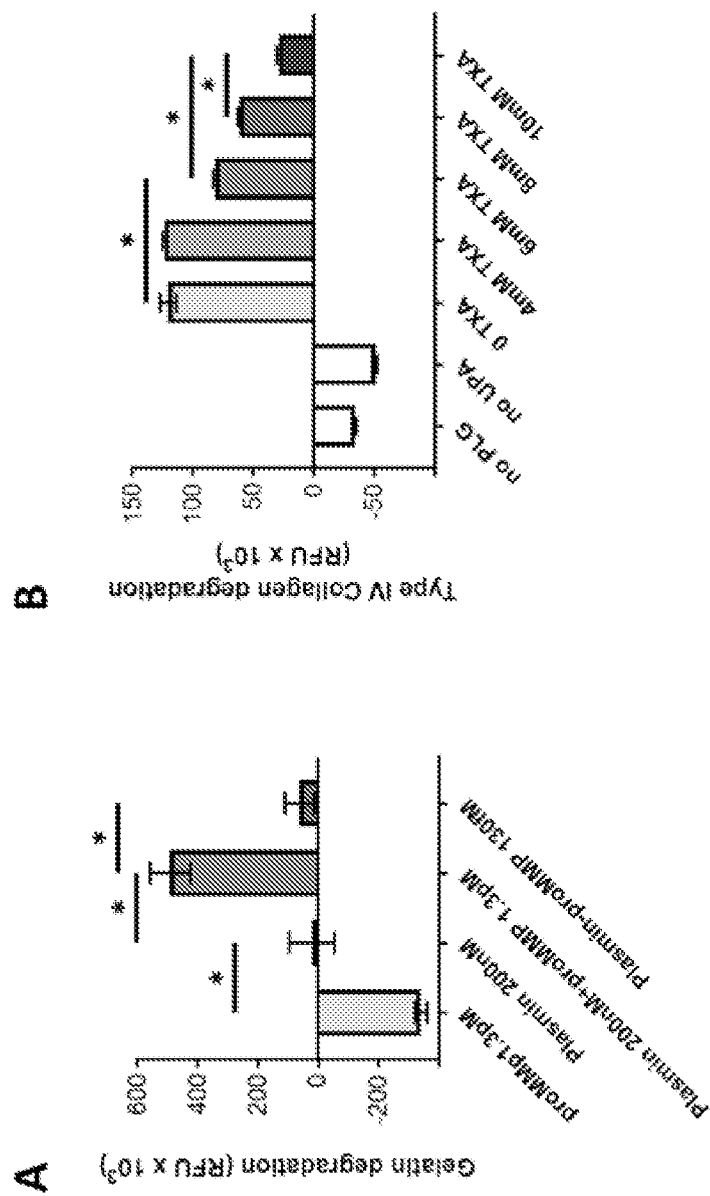
FIG. 43. Under sterile conditions, PLG and pro-MMP9 act synergistically to degrade collagen in a manner inhibited by TXA. A functional overlap exists between the collagen-degrading proteases plasmin and MMP9. Each class alone performs some collagenolysis, however the velocity of the reaction is multiplied when both active proteases act in parallel. A) The combination of PLG with uPA and pro-MMP9 degrades significantly more fluorescent gelatin than either component alone or the sum total of the two proteases alone based on initial reaction velocity after a two-hour incubation. Decreasing the concentration of either protease in the reaction diminishes overall collagen degradation (p<0.01, ANCOVA). B) In sterile conditions with PLG, active uPA and proMMP9, TXA concentration dependently inhibits degradation of type IV collagen. The reaction does not proceed in the absence of active plasmin (no PLG, no uPA) (*p<0.05, ANCOVA). Error bars indicate means±SD. All data are representative of three separate experiments, each run in triplicate.

TXA attenuates the synergistic loop of collagen degradation. Plasmin has well-described collagenolytic activity that activates pro-MMP9 and is itself activated by MMP9 (15'). Both proteases can be activated in the absence of bacteria, albeit to a lower degree. The combination of PLG with uPA and pro-MMP9 demonstrated synergistic gelatin-degrading activity in a sterile system (FIG. 43A). This activity was inhibited in a concentration-dependent manner by TXA, a compound that specifically inhibits PLG activation (FIG. 43B).

Figure 23:
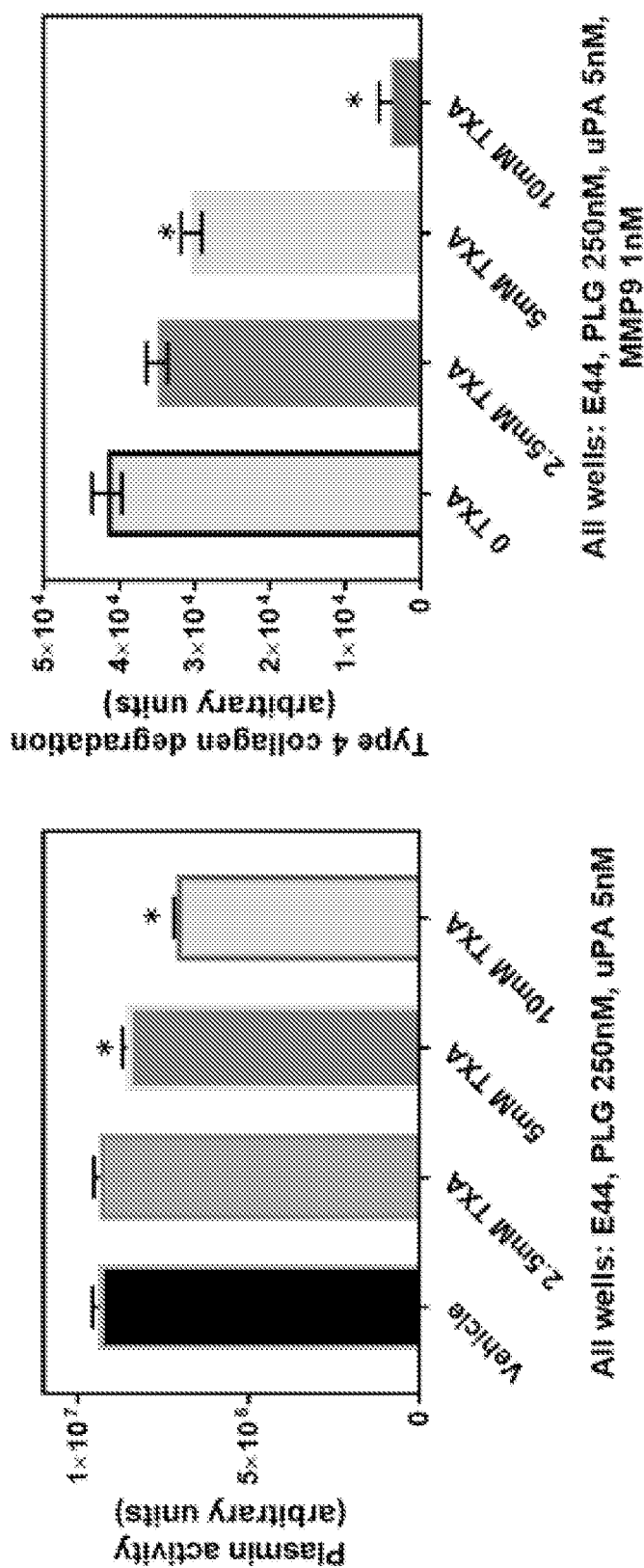
FIG. 23. Effective inhibition of PLG in vitro. The left panel shows a 20% reduction in PLG activation by *E. faecalis* in vitro at concentrations lower than concentration in the circulation of subjects when the drug is given PO. At the same concentration levels, bacterial collagen degradation is reduced over 80%, a dramatic reduction in collagen degradation underscoring the role PLG activation plays in this process. The data further corroborates the inhibition of macrophage-mediated PLG activation by tranexamic acid (TXA).
Figure 37:
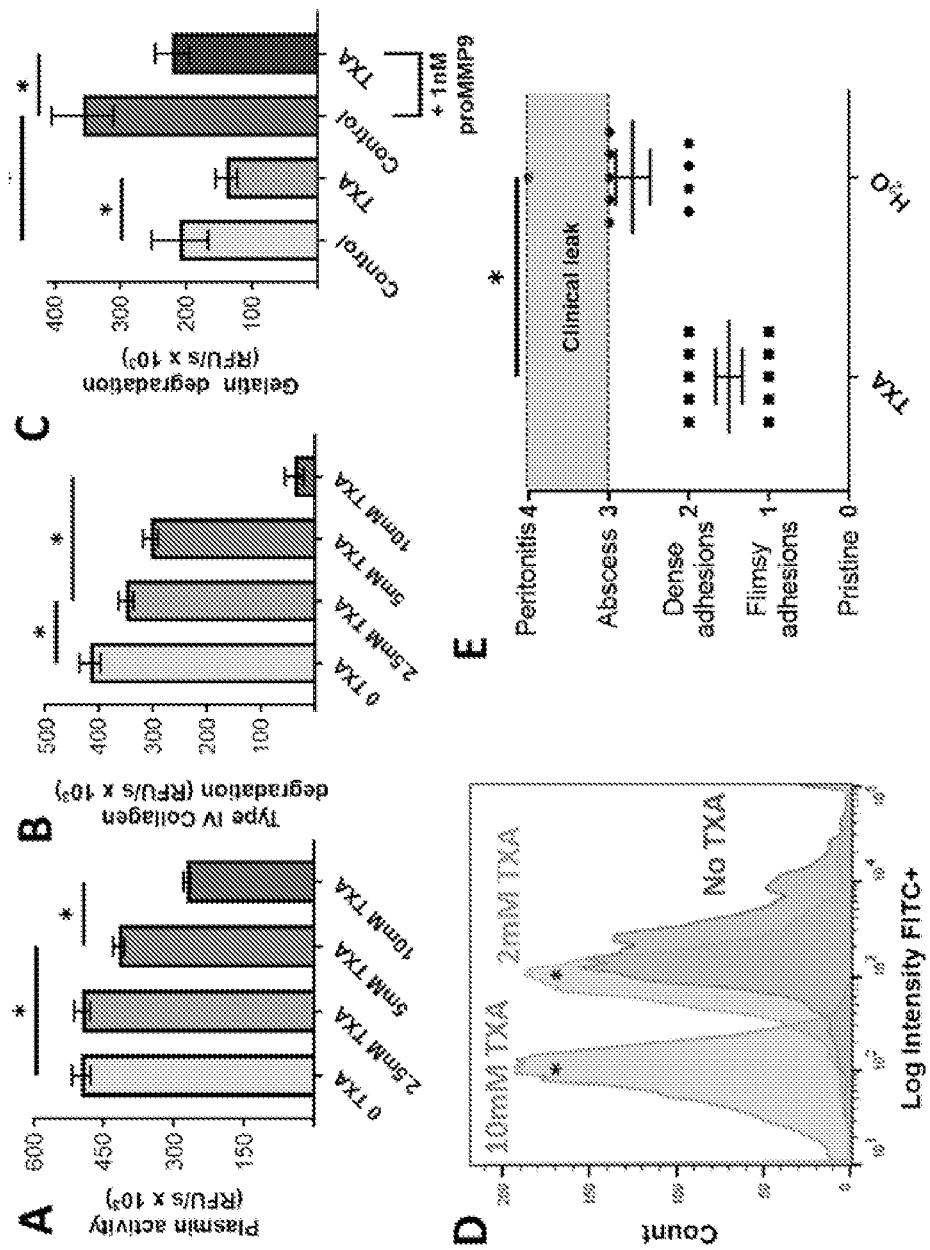
FIG. 37. TXA inhibits bacterial PLG activation and collagen degradation in vitro and rescues *E. faecalis*-mediated AL in mice. A) Plasmin activity assay demonstrating that TXA concentration-dependently inhibits PLG activation by *E. faecalis* V583 in the presence of uPA (* p<0.05, ANCOVA). B) TXA inhibits type IV collagen degradation by V583 in the presence of PLG and uPA (* p<0.05, ANCOVA). C) 10 mM TXA inhibits gelatin degradation by RAW macrophages stimulated by V583 CM, both in the presence and absence of pro-MMP9. Again, synergistic activation of PLG and pro-MMP9 was observed. (* p<0.05, ANCOVA). D) V583 was incubated in the presence of 0 (red), 2 mM (orange) and 10 mM (blue) TXA and FITC-labeled PLG. Flow cytometry demonstrated that TXA significantly inhibited cell-surface binding (* p<0.05 compared to 0 mM TXA, K-S analysis). E) In a model of V583-induced anastomotic leak, mice treated with TXA rectal enema exhibited significantly improved anastomotic healing scores on postoperative day 8, compared to mice treated with vehicle control (p<0.05 Student's t-test). Each data point represents one animal. Error bars indicate means±SD. All in vitro data are representative of three separate experiments, each run in triplicate.
Figure 44:
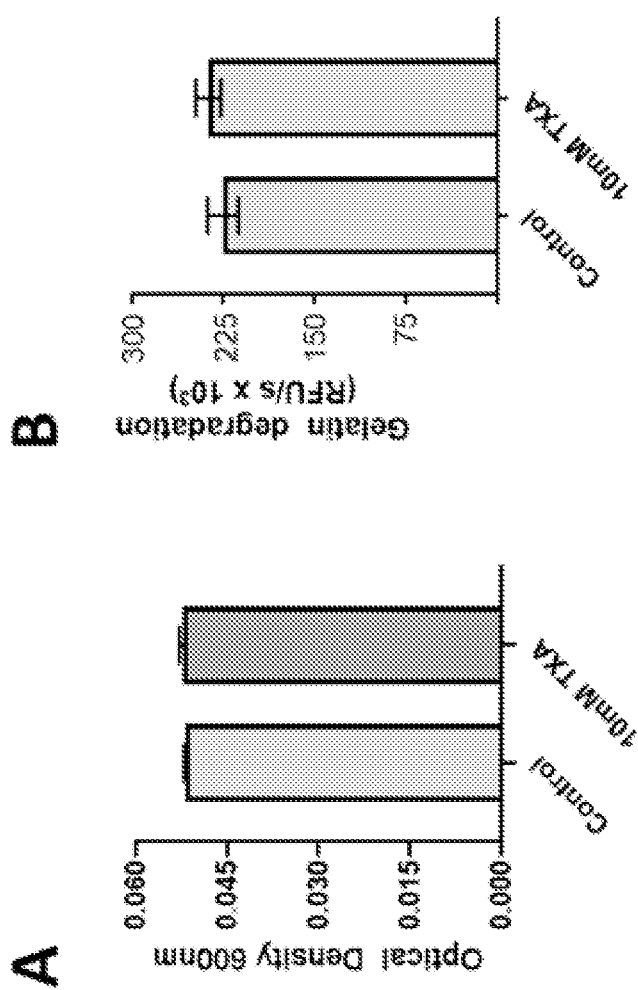
FIG. 44. Inhibition of bacterial collagen degradation by TXA is independent of bacterial growth rate, and dependent on the presence of PLG. A) TXA does not alter total bacteria growth as measured by $OD_{600}$ over a 4 hour incubation in liquid media. B) TXA had no effect on intrinsic collagenolytic activity of E. faecalis in the absence of PLG. Figures are representative of three separate experiments, each run in triplicate. Error bars indicate means±SD.

TXA inhibited PLG activation by V583 in a concentration-dependent manner in the presence of uPA (FIG. 37A, FIG. 23). Type IV collagen degradation assays were performed in the presence of V583, PLG, uPA and TXA, again demonstrating concentration-dependent inhibition (FIG. 37B, FIG. 23). RAW 276.4 cells were incubated with PLG, uPA and V583 for 6 hours and a gelatin degradation assays were performed in the presence or absence of 10 mM TXA and additional pro-MMP9. TXA significantly inhibited gelatin degradation in V583-stimulated macrophages. The gelatinolytic effect of macrophages was enhanced when pro-MMP9 was added to the reaction and again significantly diminished in the presence of 10 mM TXA (FIG. 37C). The inventors next examined whether TXA affected bacterial collagen degradation through mechanisms unrelated to PLG activation. TXA added to culture medium had no effect on bacterial growth, as measured by change in $OD_{600}$ over four hours (FIG. 44A), nor intrinsic bacterial type IV collagen degradation activity in the absence of PLG (FIG. 44B).

Example 15

Figure 45:
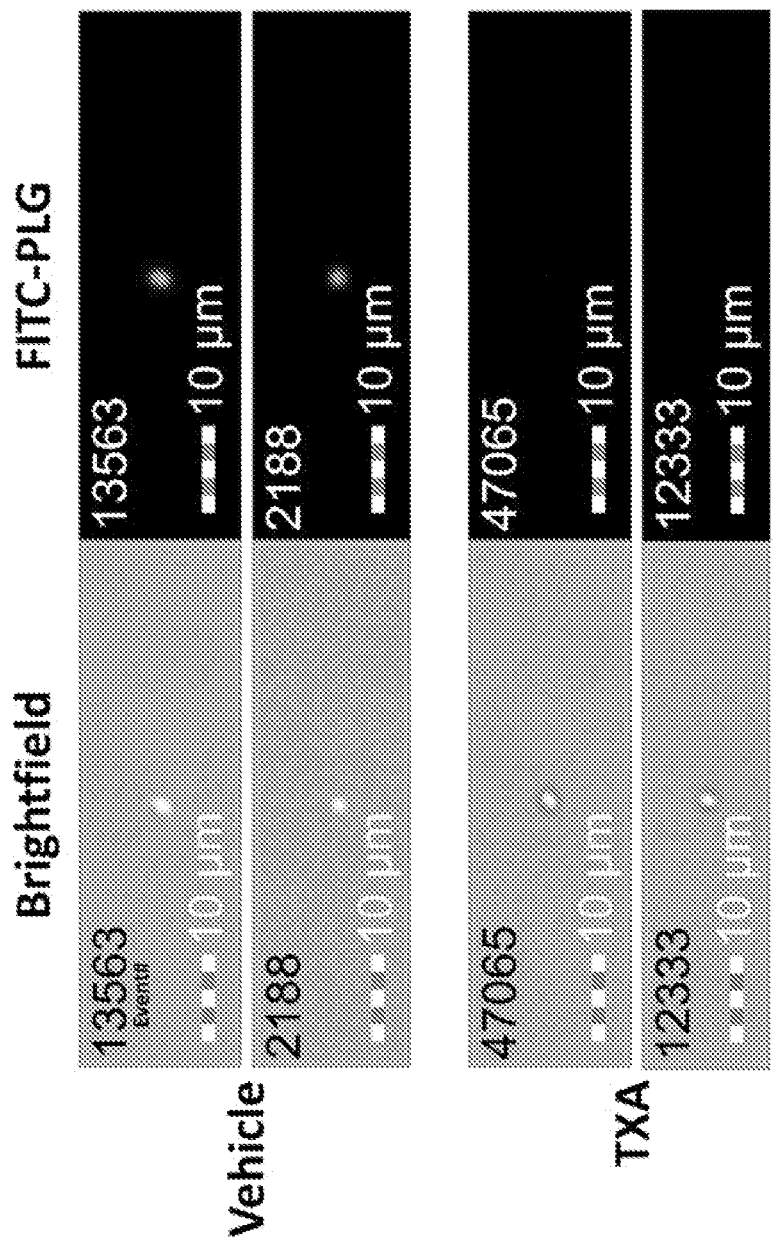
FIG. 45. Co-localization of FITC-PLG and E. faecalis inhibited by TXA. Single-cell microscopic images collected during flow cytometry experiments demonstrate FITC-range fluorescent signal co-localized with brightfield images of bacteria taken simultaneously. Fluorescent signal was not present on cells treated with TXA. Images are representative of thousands of similar images taken over three separate experiments.

TXA prevents binding of PLG to E. faecalis. Flow cytometry was performed after incubation of V583 with FITC-labeled PLG as before. 80.9% of cells reached a subjectively determined threshold for surface-bound FITC-PLG. Measured geometric mean fluorescence intensity of cells in the absence of TXA was 1768, with a coefficient of variation of 249. In the presence of 2 mM TXA, these figures fell to 936 and 252, while with 10 mM TXA they were measured as 77 and 363, respectively. Taken together, these data show a decrease in surface binding of FITC-PLG by E. faecalis in the presence of TXA. The effect was concentration-dependent and statistically significant (FIG. 37D). Concomitant single-cell microscopy confirmed co-localization of light microscopic images of bacterial cells, the FITC-range fluorescent signal from FITC-PLG, and the absence of this signal in cells treated with TXA (FIG. 45).

Example 16

Figure 26:
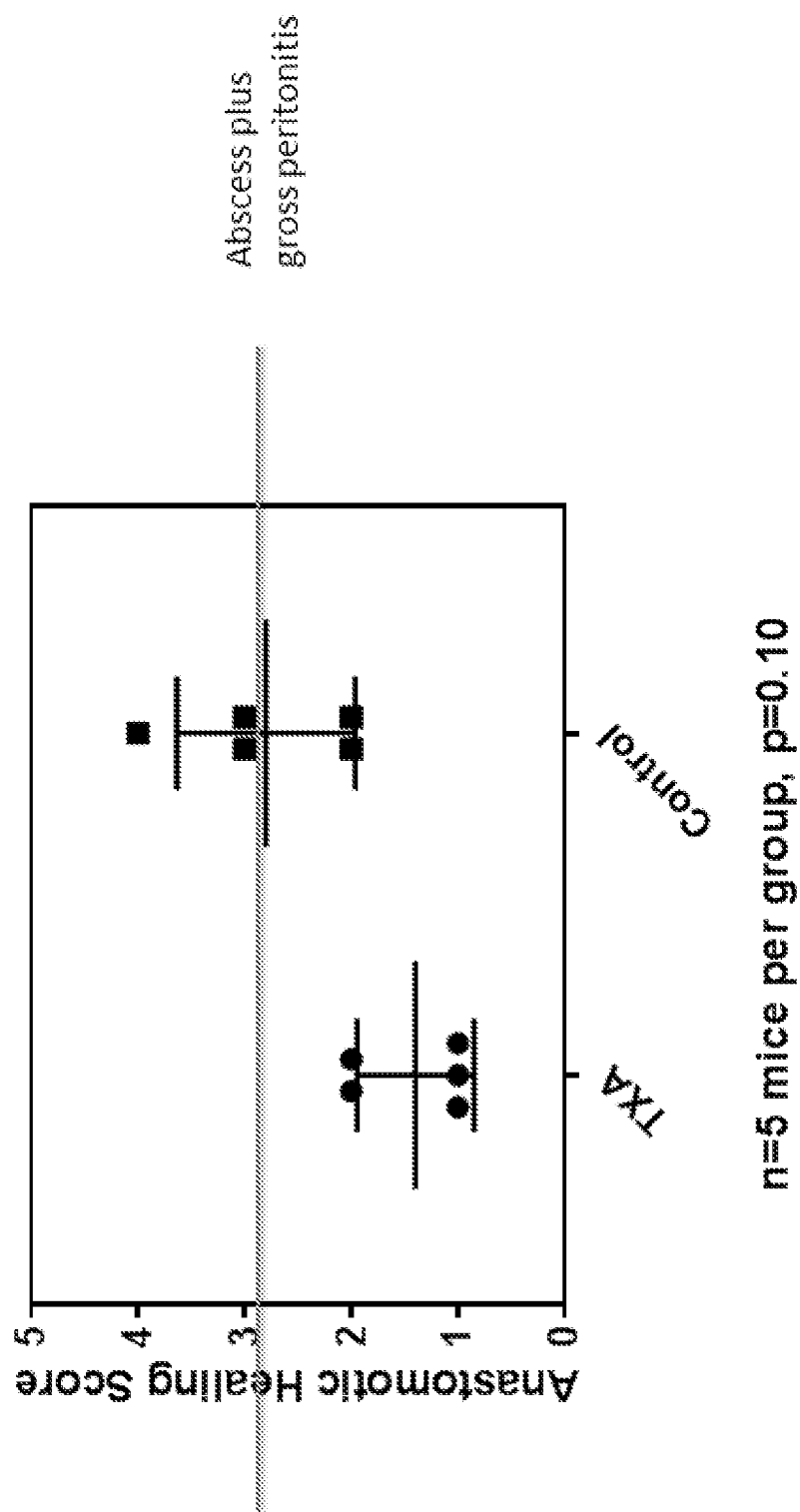
FIG. 26. Tranexamic acid prevents pathogen-mediated anastomotic leak. After exposure to antibiotics, mice underwent a colon transection and surgical anastomosis followed by introduction of collagenolytic *E. faecalis* via rectal enema with either TXA or vehicle control. One group of five mice received TXA with the *E. faecalis* and the other group of five mice received vehicle control with the *E. faecalis*. A PLG inhibitor in the form of a validated anastomotic healing score was applied to all mice in this experiment. Zero represents a perfectly healing anastomosis where 4 represents gross anastomotic disruption, and a score of 3 or greater indicates an abscess and AL. The results indicate that TXA rescued AL in vivo.
Figure 46:
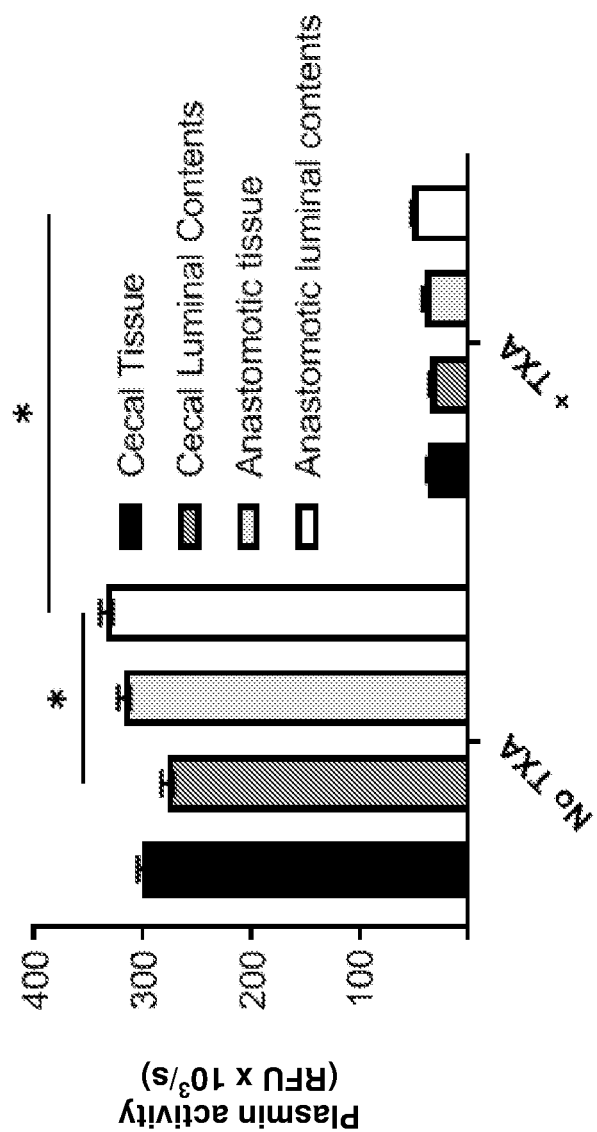
FIG. 46. Polymicrobial communities cultured from the postoperative mouse colon activate PLG in a manner inhibited by TXA. Polymicrobial communities collected from homogenized tissue and luminal contents were cultured aerobically in nonspecific media and underwent plasmin activity assays in the presence of human PLG and uPA. All communities demonstrated increased PLG activity compared to background and in all cases this was inhibited by 10 mM TXA. (*p<0.05, ANCOVA). Error bars indicate means±SD. All data are representative of three separate experiments, each run in triplicate.

Presence of PLG-activating bacteria at surgical anastomoses in mice and humans. Pathogens capable of causing AL are present throughout the colon in most healthy individuals, at low levels. Through unclear mechanisms, these populations expand under surgical conditions, particularly when complications arise (32'). Plasmin activity assays were measured in polymicrobial communities cultured aerobically from homogenized luminal contents or tissue following anastomotic surgery without antibiotics and without introduction of a leak-inducing pathogen (e.g., *E. faecalis, P. aeruginosa, S. marcescens*). These assays included exogenous PLG and uPA. Communities from homogenized tissue and luminal contents demonstrated plasmin-activating activity, which was slightly higher in anastomotic than cecal luminal contents and was in all cases significantly inhibited by 10 mM TXA (FIG. 46). The inventors next examined whether human colon anastomotic tissue harbored bacteria capable of activating the PLG system. Culture data was re-examined (10'), and all patients were found to harbor species with well-described PLG activation in their colonic mucosa. Of note, the one patient that harbored bacteria both with described PLG-activating and collagenolytic activities (*P. aeruginosa*) developed an abscess requiring percutaneous drainage, presumed secondary to AL (Table 3).

while mice treated with TXA had a mean score of $1.5\pm0.2$ ($p<0.05$ Student's t-test). To examine the clinical relevance of this data, the inventors compared groups for the presence of clinically relevant AL, meaning those with an AHS of 3 or 4. By this criterion, 6/10 mice in the vehicle group developed a clinically significant leak, while none of the mice (0/10) in the group receiving TXA did ($p<0.01$ Fisher's exact test) (FIG. 37E, FIG. 26).

Figure 47:
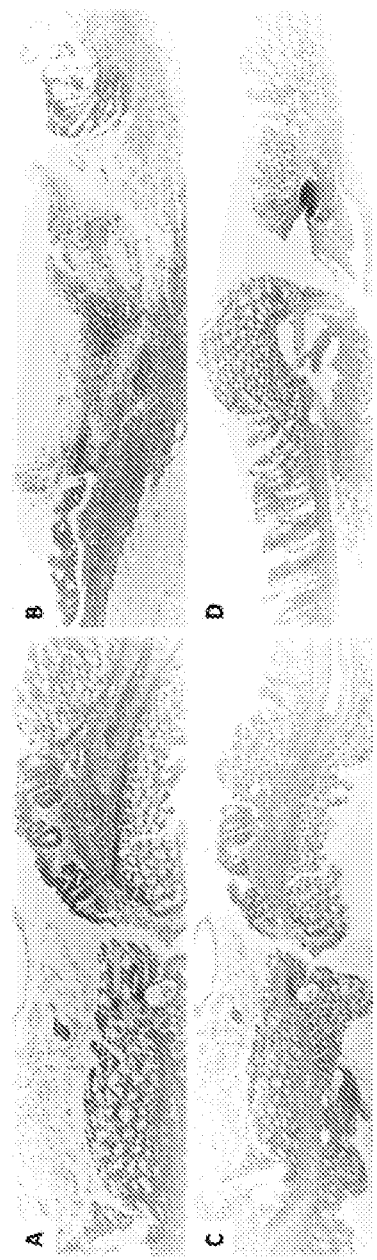
FIG. 47. TXA enema rescues supraphysiologic collagen degradation in pathogen-mediated anastomotic leak without impairing normal healing. A, B) Trichrome stains of mouse colon anastomotic site on postoperative day 8 following performance of an E. faecalis-induced anastomotic leak model. Mouse A received a TXA enema, did not suffer AL, and demonstrates organized trichrome staining in the submucosa. Mouse B received a vehicle control enema and suffered AL, demonstrating diffuse, disorganized trichrome positivity, indicating less fibroblast-secreted matrix in the submucosa and significant inflammatory infiltrate. C, D) No discernible difference in mucosal healing or inflammatory infiltrate is evident on hematoxylin and eosin stains of non-leaking mice who received post-operative TXA (C) versus vehicle enema (D) following sacrifice on postoperative day 8. Yellow arrows indicate suture line. Blue circular structures are prolene sutures. Images are representative of three mice per experiment.

Standard histologic analyses were performed on POD8 anastomotic tissue in mice that received TXA versus vehicle enemas. Trichrome staining demonstrated increased quantity and organization of fibroblastic products in the submucosa of mice that received TXA (FIG. 47A), compared to those that received vehicle and suffered AL (FIG. 47B). Hematoxylin and eosin staining revealed no discernible difference in mucosal healing or inflammatory infiltrate to the anastomotic tissue of non-leaking mice that received either TXA (FIG. 47C) or vehicle control (FIG. 47D).

The finding that PLG inhibition prevented *E. faecalis*-mediated AL was generalized to other pathogens relevant to the human condition based on the results of reiterative experiments in which *P. aeruginosa* was administered via

TABLE 3

| Species | Patient(s) | PLG activation | Collagenolytic |
|---|---|---|---|
| S. angiosus | 1, 4, 8 | X(53) | |
| S. salivarius | 2, 3, 6, 7, 8 | X(53) | |
| S. parasanguinis | 3, 4, 7, 8 | X(53) | |
| S. gallolyticus | 5 | X(54) | |
| S. mitis | 6 | X(53) | |
| S. gordonii | 6 | X(53) | |
| S. intermedius | 7 | X(53) | |
| P. aeruginosa | 7 | X(24) | X(8) |
| E. faecalis | 8 | Current paper | X(10) |
| S. marcescens | 8 | X(56) | X(8) |

Table 3. PLG system-activating and collagenolytic bacteria in human anastomotic tissue. Ten consecutive patients undergoing colon resection at the University of Chicago had the ends of the resected colon segment swabbed for microbiological analysis intraoperatively. Swabs were cultured and speciated. All patients had received mechanical bowel preparation and intravenous cefoxitin pre-operatively. Swabs from two patients were culture-negative and eight were positive. Of the culture-positive patients, all eight harbored bacterial species with well-described activation of the fibrinolytic system: 33 of 64 total cultured strains were identified as PLG activators. *Patient developed an intra-abdominal abscess requiring percutaneous drainage.

Example 17

Figure 27:
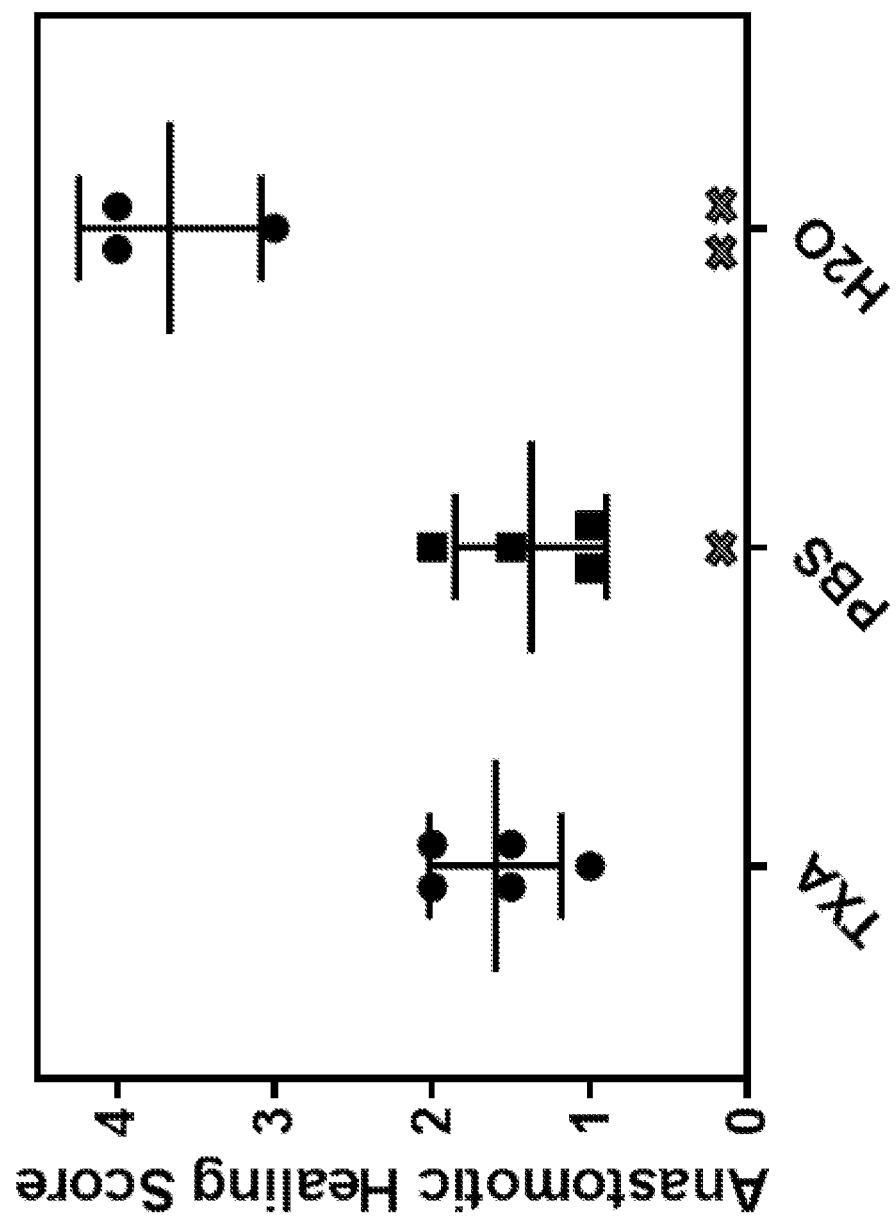
FIG. 27. The two most common bacterial genera that survive bowel preparation or cleansing are *Pseudomonas* and *Enterococcus*. To determine if the therapy for treating or reducing the risk of developing AL in response to collagenolytic *E. faecalis* was effective in treating or reducing the risk of developing *Pseudomonas*-induced AL, the following experiment was performed. After exposure to antibiotics, mice underwent a colon transection and surgical anastomosis followed by introduction of *Pseudomonas aeruginosa* MPAO1-P2 via rectal enema with either TXA or vehicle control. One group of mice received TXA with the *P. aeruginosa* and the other group of mice received vehicle control with the *P. aeruginosa*. A PLG inhibitor in the form of a validated anastomotic healing score was applied to all mice. The results show that a PLG inhibitor, e.g., tranexamic acid, prevents or reduces the likelihood of AL in comparison to animals receiving water without any PLG inhibitor.
Figure 28:
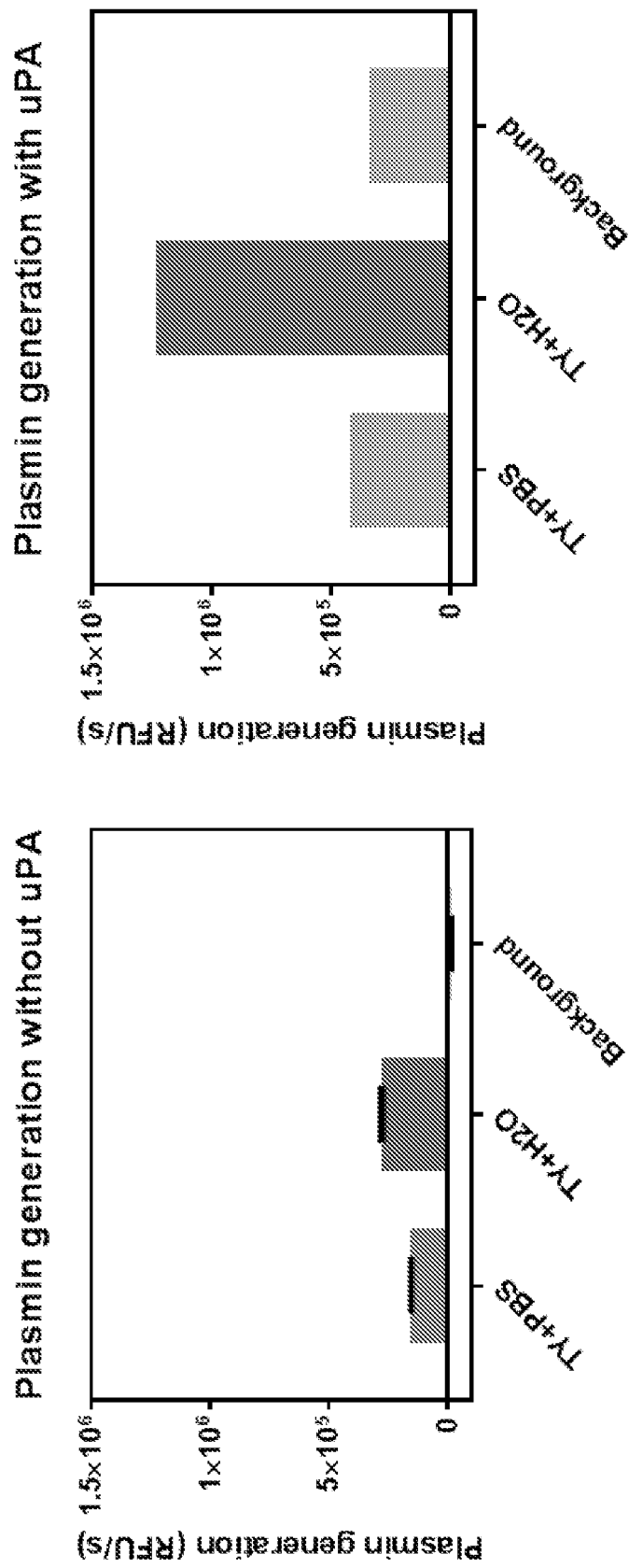
FIG. 28. Effect of urokinase, a plasminogen activator, on plasmin production.
Figure 29:
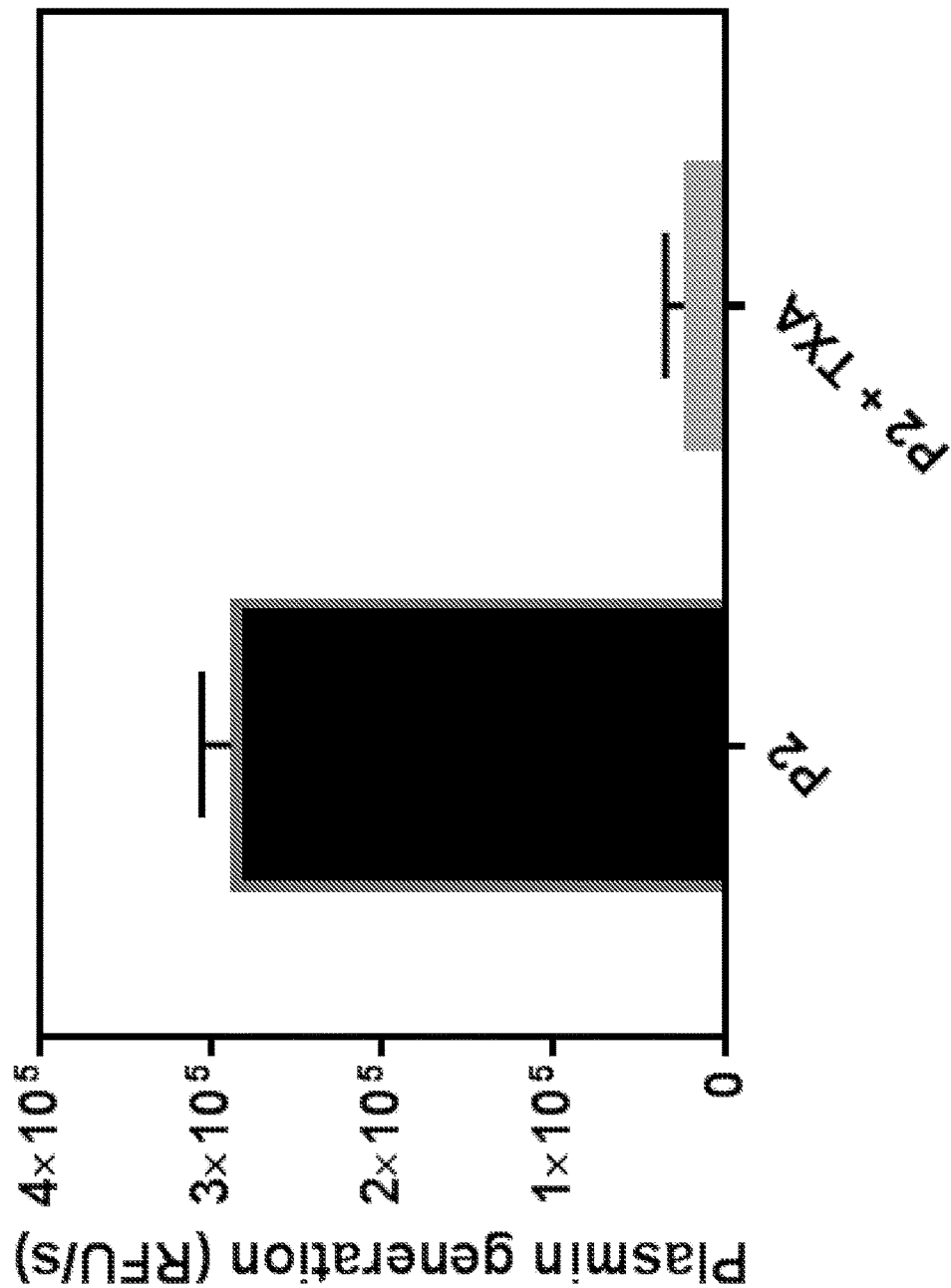
FIG. 29. Tranexamic acid inhibits *P. aeruginosa* MPAO1-P2 plasminogen activation.
Figure 30:
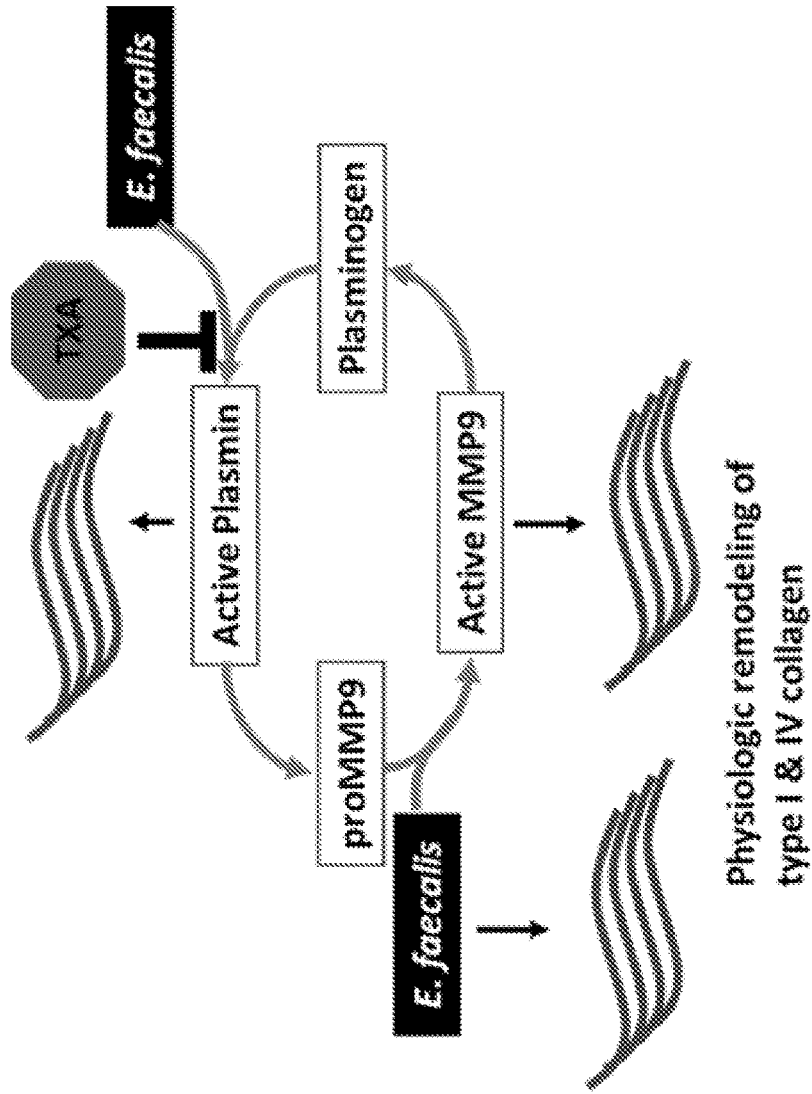
FIG. 30. A schematic illustration of the Plasminogen-proMMP9 activation cycle affected by intestinal pathogens such as collagenolytic *E. faecalis* and *P. aeruginosa* MPAO1-P2. PLG activation plays a key regulatory role in bacterial-mediated collagen degradation. TXA attenuates *E. faecalis*- and *P. aeruginosa*-mediated PLG activation and collagen degradation in vitro and rescues AL in vivo. Microbial pathogen-induced PLG activation is a key step in bacterium-mediated collagen degradation, and this activation is targetable with PLG inhibitors such as TXA and other known PLG inhibitors such as F-aminocaproic acid, providing therapies for the treatment or reduction of risk of developing anastomotic leak.
Figure 48:
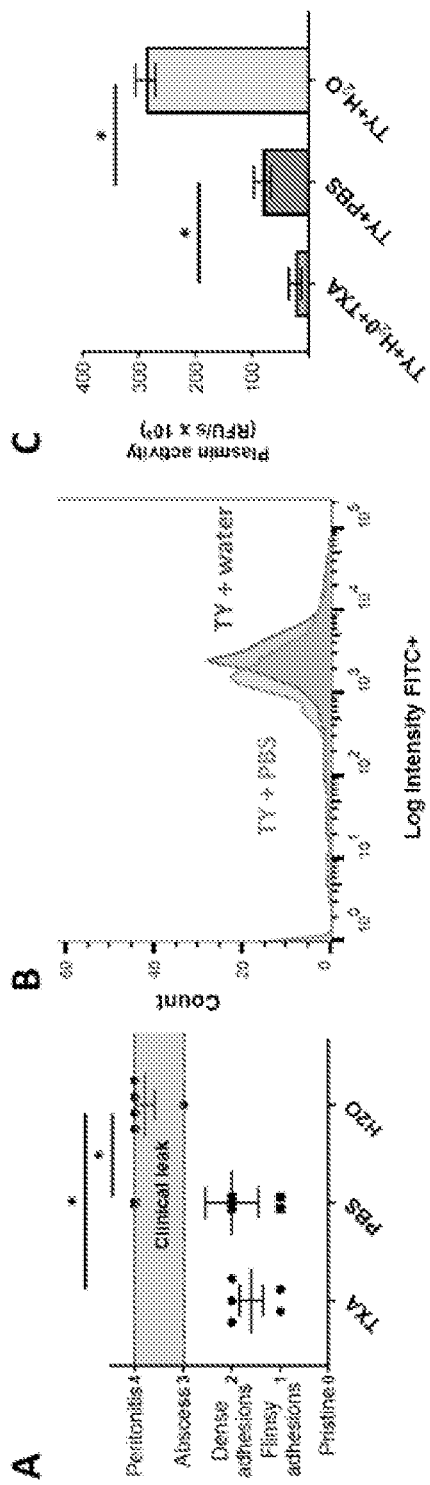
FIG. 48. Multimodal inhibition of plasminogen activation rescues P. aeruginosa-induced anastomotic leak. A) In a model of P. aeruginosa-induced anastomotic leak, mice treated with either 100 μL 50 mM TXA in water or 100 μL PBS on postoperative day 1,2 and 3 exhibited significantly improved anastomotic healing scores (AHS) on postoperative day 8, compared to mice treated with sterile deionized water vehicle control (1.6+/−0.6 (TXA) versus 2.0+/−1.2 (PBS) versus 3.8+/−0.4 (water), p<0.05 Student's t-test). Each data point represents one animal. B) Flow cytometry of 1000 cells of P. aeruginosa cultured in TY with added water (red) versus PBS (blue). When cultured with PBS, binding of FITC-PLG significantly decreased from a geometric mean fluorescence intensity of 1294 to 916 (coefficient of variation 185% and 189%, respectively, p<0.05 K-S analysis). C) Multimodal in vitro inhibition of bacterial PLG activation. P. aeruginosa cultured in TY media diluted in a 1:1 (v/v) ratio with PBS (10 mM phosphate) activated significantly less PLG than the same strain in TY with a 1:1 (v/v) ratio with sterile deionized water. A similar decrease in PLG activity was observed when 10 mM TXA in phosphate-free water was added to P. aeruginosa cultured in TY with added water. (*p<0.05 ANCOVA). Error bars indicate means±SD. All in vitro experiments were run in triplicate with representative data shown.

Locally delivered tranexamic acid prevents anastomotic leak caused by *E. faecalis* and *E. aeruginosa* in mice. Twelve-week-old C57BL/6 mice were given pre-operative enteral clindamycin and parenteral cefoxitin, followed by colorectal anastomotic surgery, as previously described (8'). On postoperative day (POD) 1, 2 and 3, mice received a 100 µL rectal enema containing V583 in 10% glycerol, followed by a second 100 µL enema of 50 mM TXA in sterile water or sterile water as a vehicle control, with 10 mice per group. The inventors used the validated Anastomotic Healing Score (AHS) to assess the presence of a leak at necropsy, with 0=pristine healing, 1=flimsy adhesions, 2=dense adhesions, 3=gross abscess and 4=gross anastomotic disruption. On POD 8, mice receiving vehicle had a mean score of $2.7\pm0.2$ enema on POD1 to contaminate anastomoses in mice. In contrast to *E. faecalis*, the interaction of host PLG and *P. aeruginosa* has been described (24'). In addition, the inventors knew that local phosphate abundance at concentrations similar to the 10 mM level found in PBS suppressed virulence expression in *P. aeruginosa* via its well-described phosphosenory and phosphoregulatory system that regulates quorum sensing (33'). Similar enema dosing regimens were applied to 5 mice per group with 50 mM TXA in sterile water, sterile water as a vehicle control, or PBS on POD 1, 2 and 3. None of the mice that received TXA developed a clinical leak, and AHS was $1.6\pm0.5$. Two mice treated with water died of intra-abdominal sepsis secondary to feculent peritonitis prior to planned sacrifice on POD8. The group receiving water demonstrated significantly worse post-operative healing as measured by AHS, $3.8\pm0.4$ ($p<0.05$ versus TXA, Student's t-test). In the group that received PBS, one developed a gross leak and died of intra-abdominal sepsis prior to planned sacrifice. The remainder of this group survived to sacrifice, and mean AHS was not significantly different from the TXA-treated group at $2.0\pm1.2$ (FIG. 48A, FIG. 27).

To investigate the mechanism of the relative rescue of *P. aeruginosa*-induced leak by PBS, the inventors examined the impact of phosphate on the ability of *P. aeruginosa* to activate PLG. During log phase growth in 2 mL TY media, bacteria were treated with an additional 2 mL of either PBS or sterile deionized water. Exposure to PBS changed the bacterial phenotype indicated by a grossly apparent change in media color after 24 hours of growth. *P. aeruginosa* exposed to PBS compared to water bound less FITC-PLG, as measured by flow cytometry, with a decrease in geometric mean fluorescence intensity from 1294 to 916 with coefficient of variation 185% and 189%, respectively (FIG. 48B). Accordingly, the ability of *P. aeruginosa* to activate PLG was significantly attenuated in bacteria grown in the presence of PBS and the same strain treated with water and 10 mM TXA, compared to water alone (FIG. 48C). These data re-demonstrate a rescue of pathogen-mediated AL through PLG inhibition via two distinct modalities, and indicate a protective role for phosphate in the prevention of *P. aeruginosa*-mediated AL.

Example 18

Plasminogen preferentially binds to the site of anastomotic injury. The role of PLG in intestinal wound healing has not been studied. The inventors first examined PLG binding capacity in surgically injured anastomotic tissue versus uninjured colon tissue. A colorectal anastomosis designed to heal, without pre-operative antibiotics or post-operative introduction of pathogen, was performed on 12-week-old mice. Sections of anastomotic tissue and remote uninjured tissue were collected at various time points after surgery, incubated ex vivo in a solution of FITC-labeled PLG in PBS, and washed. Gross colon tissue at 40× magnification after incubation with FITC-labeled PLG and washing. Non-injured tissue demonstrated minimal binding of FITC-PLG. Tissue recovered 10 minutes following anastomosis began to demonstrate FITC-PLG binding at the anastomotic site. At 48 hours post-anastomosis, total PLG binding had increased and spatial distribution remained concentrated on the suture line. Anastomotic tissue recovered at 24 hours post-surgery at 10× magnification. The mouse received systemic (intraperitoneal) FITC-PLG an hour prior to sacrifice and demonstrated the full spatial distribution of PLG which stained green. Minimal PLG binding was observed on non-injured tissue. Specific binding of FITC-PLG was observed in tissue collected as early as 10 minutes after surgery. Tissues collected 48 hours post-operatively avidly bound PLG with the strongest staining in areas closest to the anastomotic suture line. Three mice per time point were used in this experiment. Thus, Anastomotic surgery promoted the accumulation of PLG in a fashion inhibited by TXA.

Example 19

Figure 38:
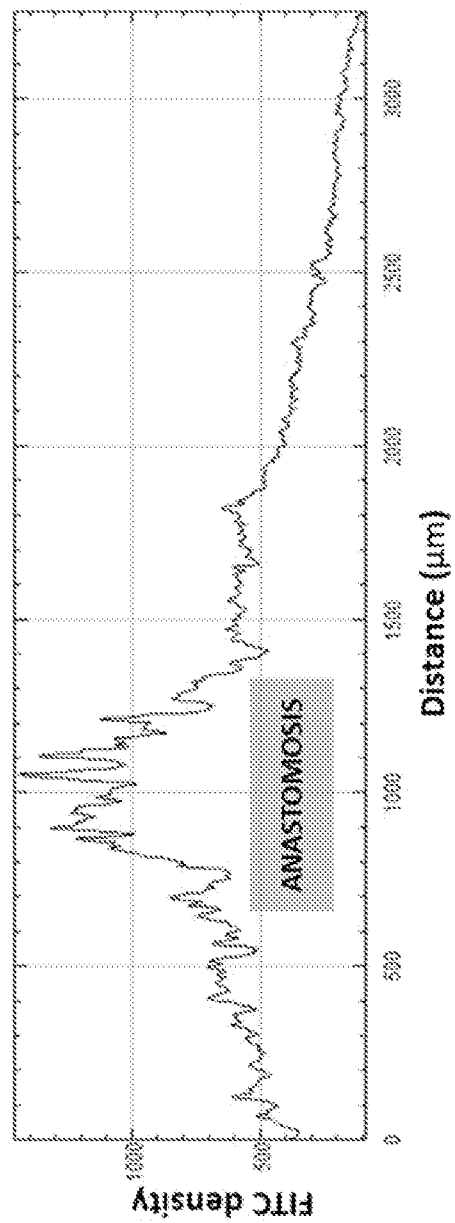
FIG. 38. Anastomotic surgery promotes accumulation of PLG in a fashion inhibited by TXA. Anastomotic tissue recovered at 24 hours post-surgery at 10× magnification. The mouse received systemic (intraperitoneal) FITC-PLG an hour prior to sacrifice and demonstrates the full spatial distribution of PLG (green). Spatial quantification of FITC-PLG fluorescence intensity across the length of the representative tissue.

Plasminogen deposition at the site of anastomotic injury. Having demonstrated the capacity of anastomotic tissue to bind PLG ex vivo, the inventors next examined the in vivo deposition of systemically administered FITC-PLG at surgical anastomoses. Mice underwent anastomosis without exposure to antibiotics or exogenous pathogen followed by intraperitoneal injection with FITC-PLG and either TXA or vehicle control enema one hour prior to sacrifice. Three animals per treatment group were sacrificed at various time points. Mouse colon stained with DAPI following colorectal anastomosis was observed at 20× magnification. Either TXA or water vehicle enema was administered along with systemic FITC-PLG injection one hour prior to sacrifice. At 48 hours post-operative, mice receiving vehicle had strong fluorescence accumulation, where diminished FITC-PLG was observed at the anastomotic site in mice receiving TXA. A similar pattern was observed at 72 hours post-operative in control and TXA mice. Total FITC-PLG fluorescent signal was quantified in all mice as integrated density/area. Mice treated with TXA had significantly less FITC-range signal at the anastomosis. A segment of anastomotic tissue collected from a mouse that received no enemas at 24 hours post-operative was observed. FITC-PLG fluorescence intensity is spatially quantified across the length of the tissue. Green FTIC-PLG staining is qualitatively strongest at the surgical site and gradually fades moving both proximally and distally away from the anastomosis (yellow arrow). This pattern was confirmed when FITC staining intensity from the same sample was quantified spatially, as shown in FIG. 38.

Figure 39:
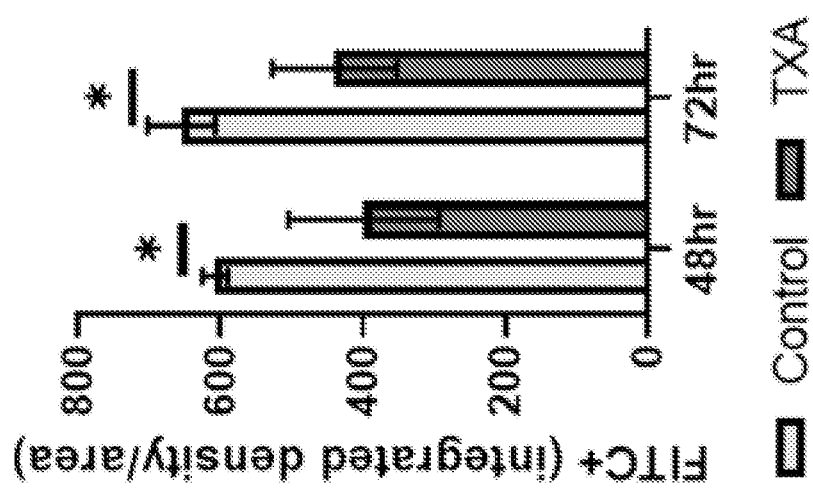
FIG. 39. Anastomotic surgery promotes accumulation of PLG in a fashion inhibited by TXA. Total FITC-PLG fluorescent signal was quantified in all mice as integrated density/area. Mice treated with TXA had significantly less FITC-range signal at the anastomosis. All images are representative of n=3 mice per treatment group.

Anastomotic tissues demonstrating persistent FITC-PLG staining at 48 and 72 hours post-operative in mice treated with vehicle enemas were observed. Also observed were anastomotic tissues demonstrating the effect of TXA enemas on PLG deposition at the anastomoses at these time points. Green FITC-PLG staining is markedly reduced, indicating diminished PLG deposition at the anastomotic site in TXA-treated animals. Mean FITC staining intensity was quantified as integrated density/area at the anastomotic sites of three mice per treatment group at the 48- and 72-hour time points. TXA treatment significantly decreased the amount of FITC-PLG positivity at the anastomosis at both time points (FIG. 39).

Example 20

Co-localization of *E. faecalis* and plasminogen at the anastomotic site. The inventors next determined if the in vitro finding of PLG binding to the surface of *E. faecalis* and inhibition of this process with TXA could be reproduced in the in vivo model of AL. Mice underwent V583-induced AL with intraperitoneal injection of FITC-PLG on POD3. Mice had received enemas of TXA or vehicle control (n=3 mice per group) on post-operative days 1, 2 and 3. Frozen sections were stained with DAPI for colonic tissue and a FISH probe specific to *E. faecalis* DNA. V583 co-localized with FITC-PLG at the anastomotic site in mice receiving vehicle. TXA enema effectively prevented co-localization and diminished penetration of V583 into the colonic mucosa. *E. faecalis* co-localized with PLG in anastomotic tissue in a fashion inhibited by TXA enema. Mice undergoing *E. faecalis*-mediated anastomotic leak were administered FITC-labeled PLG (as observed by green fluorescence) systemically. Anastomotic tissues were stained for *E. faecalis* DNA (red fluorescence) and colonocyte nuclei (blue staining), as revealed at 40× magnification. Mice treated with vehicle enema had significant penetration of *E. faecalis* (red spheroids) into the colonic mucosa, along with increased PLG at the anastomotic site. Non-spherical red staining was non-specific. Merged images demonstrated co-localization of *E. faecalis* and FITC-PLG (yellow spheroids) at the anastomosis. Mice treated with TXA enema demonstrated diminished penetrance of *E. faecalis* into the mucosa and no co-localization of *E. faecalis* with FITC-PLG at the anastomotic site. Red-stained *E. faecalis* remained in the mucus layer above colonic crypts.

Figure 49:
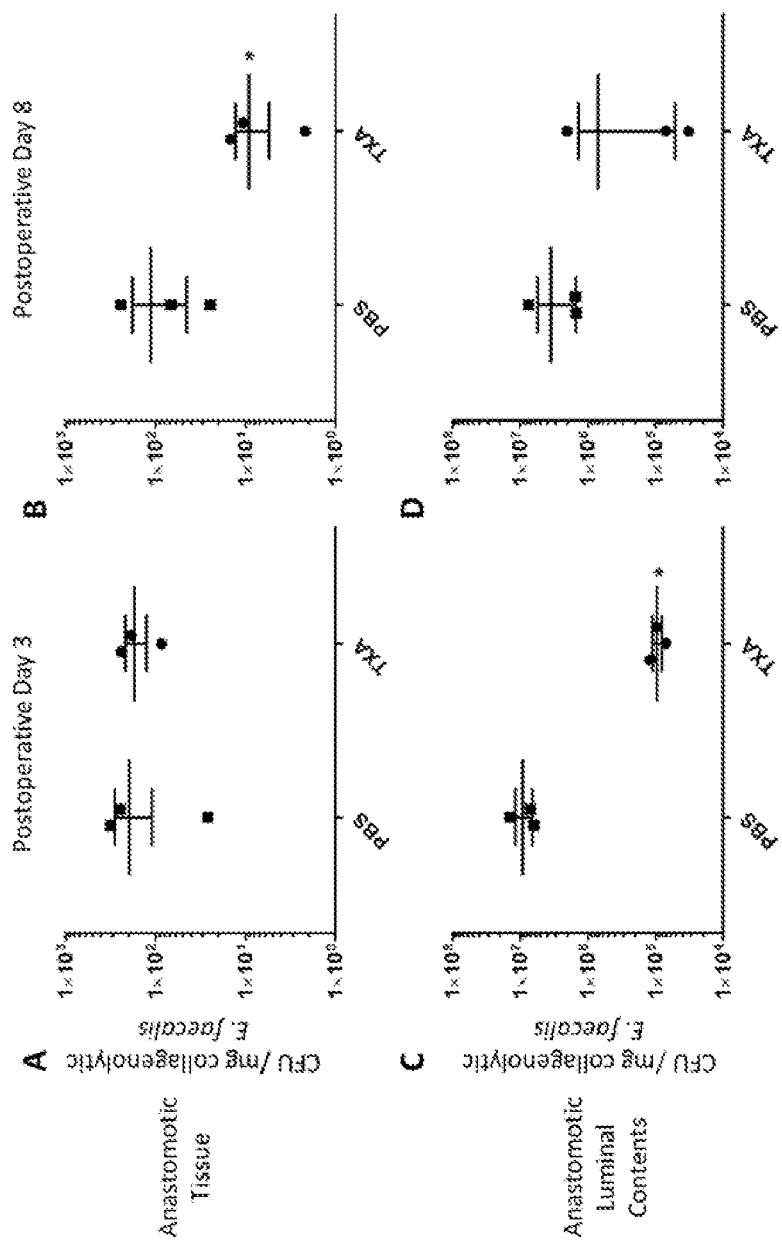
FIG. 49. TXA enema reduces density of collagenolytic E. faecalis at the anastomotic site. Mice underwent a model of E. faecalis-mediated anastomotic leak and received TXA or vehicle (water) enema on post-operative days 1, 2 and 3. Endpoint colony counts of collagenolytic E. faecalis were performed at sacrifice on postoperative days 3 and 8. Anastomotic tissue and luminal contents were excised under sterile conditions, weighed and homogenized. Homogenate was spread onto skim milk plates selective for Enterococcus. A) At postoperative day 3, treatment with TXA did not alter the concentration of collagenolytic E. faecalis in anastomotic tissue. B) By postoperative day 8, a significant difference in total CFU/mg of collagenolytic E. faecalis was observed in the treatment group, likely indicative of decreased tissue penetrance by bacteria or recovery of the normal microbiome in the setting of a healed anastomosis. C) Mice treated with TXA had significantly fewer CFU/mg collagenolytic E. faecalis in luminal contents at postoperative day 3. D) Treatment group animals had persistently low CFU/mg, however this failed to reach statistical significance by postoperative day 8. Each data point represents 1 animal. * p<0.05 Student's t-test. Error bars indicate 95% confidence intervals.

The images described above are supported by quantitative culture data collected in a separate experiment. Mice underwent V583-induced AL with either TXA or water enema on POD 1,2 and 3. Mice treated with TXA enema had significantly fewer CFU/mg collagenolytic *E. faecalis* in anastomotic tissue by POD 8, while no difference was observed on day 3. TXA enema significantly decreased the amount of collagenolytic *E. faecalis* in anastomotic luminal contents by POD 3, and this effect persisted but did not reach statistical significance by POD 8 (FIG. 49).

Example 21

Nucleotide BLAST analysis was used to predict mechanisms of PLG activation by *E. faecalis*. Multiple bacterial species activate human PLG and utilize it for virulence—either through secreted factors causing disseminated activation, or via binding to surface receptors and activation by host factors localized to infected tissues (17'). Group A Streptococcal species are evolutionary relatives of *E. faecalis* that activate PLG through secreted streptokinase (18'). Streptokinase directly activates PLG in a manner independent of cleavage by its endogenous activator urokinase (uPA), and uninhibited by the endogenous PLG regulator $\alpha$2-antiplasmin (18'). To investigate the presence of streptokinase-like genes in the *E. faecalis* genome, genomic DNA of *E. faecalis* V583 was cross-referenced with Streptococcal streptokinase using nucleotide BLAST analysis (56'). Results revealed no genes in the *E. faecalis* genome encoding a protein homologous to streptokinase, as expressed by *Streptococcus pyogenes*. PLG bound to surface receptors on host cells or microbes undergoes conformational changes that render it amenable to cleavage-based activation by uPA. Recent work has shown that *E. faecalis* expresses putative PLG receptors on the cell surface (20'). Based on these findings, it is expected that any PLG activation by *E. faecalis* would depend on surface binding and cleavage-based activation by uPA. The publicly available NCBI nucleotide BLAST database was utilized for this search (56'). The search strategy was 1) Accession AM903378.1 for streptokinase of S. *Pyogenes*, 2) Taxid 226185 for *E. faecalis* strain V583, 3) nucleotide collection (nr/nt) database, and 4) megablast search algorithm for highly similar sequences.

REFERENCES

[1] Teillant, A.; Gandra, S.; Barter, D.; Morgan, D. J.; Laxminarayan, R., Potential Burden of Antibiotic Resistance on Surgery and Cancer Chemotherapy Antibiotic Prophylaxis in the USA: a Literature Review and Modelling Study. Lancet Infect. Dis. 2015, 15, 1429-1437.
[2] Price, R. J.; Cuthbertson, B. H.; Su, D. c., Selective Decontamination of the Digestive Tract and Oropharynx: After 30 Years Of Debate is the Definitive Answer in Sight? Curr. Opin. Crit. Care. 2016, 22, 161-166.
[3] Zaborin, A.; Defazio, J. R.; Kade, M.; Kaiser, B. L. D.; Belogortseva, N.; Camp, D. G.; Smith, R. D.; Adkins, J. N.; Kim, S. M.; Alverdy, A.; Goldfeld, D.; Firestone, M. A.; Collier, J. H.; Jabri, B.; Tirrell, M.; Zaborina, O.; Alverdy, J. C., Phosphate-Containing Polyethylene Glycol Polymers Prevent Lethal Sepsis by Multidrug-Resistant Pathogens. Antimicrob. Agents Chemother. 2014, 58, 966-977.
[4] Vale, P. F. M., L.; Doeschl-Wilson, A.; King, K. C.; Popat, R.; Domingo-Sananes, M. R.; Allen, J. E.; Soares, M. P.; Kummerli, R., Beyond Killing: Can We Find New Ways to Manage Infection? Evol. Med. Public Health 2016, 1, 148-157.
[5] Banerjee, I.; Pangule, R. C.; Kane, R. S., Antifouling Coatings: Recent Developments in the Design of Surfaces that Prevent Fouling by Proteins, Bacteria, and Marine Organisms. Adv. Mater. 2011, 23, 690-718.
[6] Camps, M.; Barani, A.; Gregori, G.; Bouchez, A.; Le Berre, B.; Bressy, C.; Blache, Y; Briand, J. F., Antifouling Coatings Influence both Abundance and Community Structure of Colonizing Biofilms: a Case Study in the Northwestern Mediterranean Sea. Appl. Environ. Microbiol. 2014, 80, 4821-4831.
[7] Dimitriou, M. D.; Zhou, Z. L.; Yoo, H. S.; Killops, K. L.; Finlay, J. A.; Cone, G.; Sundaram, H. S.; Lynd, N. A.; Barteau, K. P.; Campos, L. M.; Fischer, D. A.; Callow, M. E.; Callow, J. A.; Ober, C. K.; Hawker, C. J.; Kramer, E. J., A General Approach to Controlling the Surface Composition of Poly(ethylene oxide)-Based Block Copolymers for Antifouling Coatings. Langmuir 2011, 27, 13762-13772.
[8] Gao, Q.; Yu, M.; Su, Y; Xie, M.; Zhao, X.; Li, P.; Ma, P. X., Rationally Designed Dual Functional Block Copolymers for Bottlebrush-like Coatings: In vitro and In vivo Antimicrobial, Antibiofilm, and Antifouling Properties. Acta Biomater. 2017, 51, 112-124.
[9] Zhou, Z. L.; Calabrese, D. R.; Taylor, W.; Finlay, J. A.; Callow, M. E.; Callow, J. A.; Fischer, D.; Kramer, E. J.; Ober, C. K., Amphiphilic Triblock Copolymers with PEGylated Hydrocarbon Structures as Environmentally Friendly Marine Antifouling and Fouling-release Coatings. Biofouling 2014, 30, 589-604.
[10] Wang, Y P.; Pitet, L. M.; Finlay, J. A.; Brewer, L. H.; Cone, G.; Betts, D. E.; Callow, M. E.; Callow, J. A.; Wendt, D. E.; Hillmyer, M. A.; DeSimone, J. M., Investigation of the Role of Hydrophilic Chain Length in Amphiphilic Perfluoropolyether/Poly(ethylene glycol) Networks: Towards High-performance Antifouling Coatings. Biofouling 2011, 27, 1139-1150.
[11] Wu, L. C.; Zaborina, O.; Zaborin, A.; Chang, E. B.; Musch, M.; Holbrook, C.; Shapiro, J.; Turner, J. R.; Wu, G. H.; Lee, K. Y C.; Alverdy, J. C., High-molecular-weight Polyethylene Glycol Prevents Lethal Sepsis due to Intestinal *Pseudomonas Aeruginosa*. Gastroenterology 2004, 126, 488-498.
[12] Vilar, G.; Tulla-Puche, J.; Albericio, F., Polymers and Drug Delivery Systems. Curr. Drug Deliv. 2012, 9, 367-394.
[13] Kolate, A.; Baradia, D.; Patil, S.; Vhora, I.; Kore, G.; Misra, A., PEG—a Versatile Conjugating Ligand for Drugs and Drug Delivery Systems. J. Control. Release 2014, 192, 67-81.
[14] Liechty, W. B.; Kryscio, D. R.; Slaughter, B. V; Peppas, N. A., Polymers for Drug Delivery Systems. Annu. Rev. Chem. Biomol. Eng. 2010, 1, 149-173.
[15] Bergwitz, C.; Juppner, H., Phosphate Sensing. Adv. Chronic. Kidney Dis. 2011, 18, 132-144.
[16] Luong, P. M.; Shogan, B. D.; Zaborin, A.; Belogortseva, N.; Shrout, J. D.; Zaborina, O.; Alverdy, J. C., Emergence of the P2 Phenotype in *Pseudomonas aeruginosa* PAO1 Strains Involves Various Mutations in mexT or mexF. J. Bacteriol. 2014, 196, 504-513.
[17] Zaborina, O.; Lepine, F.; Xiao, G. P.; Valuckaite, V.; Chen, Y M.; Li, T.; Ciancio, M.; Zaborin, A.; Petrof, E. O.; Turner, J. R.; Rahme, L. G.; Chang, E.; Alverdy, J. C., Dynorphin Activates Quorum Sensing Quinolone Signaling in *Pseudomonas Aeruginosa* Plos Pathog. 2007, 3, e35.
[18] Zaborin, A.; Gerdes, S.; Holbrook, C.; Liu, D. C.; Zaborina, O. Y; Alverdy, J. C., *Pseudomonas Aeruginosa* Overrides the Virulence Inducing Effect of Opioids When it Senses an Abundance of Phosphate. Plos One 2012, 7, e34883.
[19] Zaborin, A.; Smith, D.; Garfield, K.; Quensen, J.; Shakhsheer, B.; Kade, M.; Tirrell, M.; Tiedje, J.; Gilbert, J. A.; Zaborina, O.; Alverdy, J. C., Membership and Behavior of Ultra-Low-Diversity Pathogen Communities Present in the Gut of Humans during Prolonged Critical Illness. mBio 2014, 5, e01361-01314.

[20] Li, Z. Y; Li, P. P.; Huang, J. L., Synthesis of Amphiphilic Copolymer Brushes: Poly(Ethylene Oxide)-graft-Polystyrene. J. Polym. Sci. A Polym. Chem. 2006, 44, 4361-4371.

[21] Mangold, C.; Wurm, F.; Obermeier, B.; Frey, H., Hetero-Multifunctional Poly(ethylene glycol) Copolymers with Multiple Hydroxyl Groups and a Single Terminal Functionality. Macromol. Rapid Comm. 2010, 31, 258-264.

[22] Zhou, P.; Li, Z. Y; Chau, Y, Synthesis, Characterization, and In Vivo Evaluation of Poly(Ethylene Oxide-co-Glycidol)-Platinate Conjugate. Eur. J. Pharm. Sci. 2010, 41, 464-472.

[23] Zaborin, A.; Romanowski, K.; Gerdes, S.; Holbrook, C.; Lepine, F.; Long, J.; Poroyko, V; Diggle, S. P.; Wilke, A.; Righetti, K.; Morozova, I.; Babrowski, T.; Liu, D. C.; Zaborina, O.; Alverdy, J. C., Red Death in *Caenorhabditis Elegans* Caused by *Pseudomonas Aeruginosa* PAO1. Proc. Natl. Acad. Sci. USA 2009, 106, 6327-6332.

[24] Jensen, V.; Lons, D.; Zaoui, C.; Bredenbruch, F.; Meissner, A.; Dieterich, G.; Munch, R.; Haussler, S., Rhlr Expression in *Pseudomonas Aeruginosa* is Modulated by the *Pseudomonas* Quinolone Signal via PhoB-Dependent and -Independent Pathways. J. Bacteriol. 2006, 188, 8601-8606.

[25] Xiao, G. P.; Deziel, E.; He, J. X.; Lepine, F.; Lesic, B.; Castonguay, M. H.; Milot, S.; Tampakaki, A. P.; Stachel, S. E.; Rahme, L. G., MvfR, a Key *Pseudomonas Aeruginosa* Pathogenicity LTTR-class Regulatory Protein, Has Dual Ligands. Mol. Microbiol. 2006, 62, 1689-1699.

[26] Zaborina, O.; Zaborin, A.; Romanowski, K.; Babrowski, T.; Alverdy, J., Host Stress and Virulence Expression in Intestinal Pathogens: Development of Therapeutic Strategies Using Mice and *C. elegans*. Curr. Pharm. Design 2011, 17, 1254-1260.

[27] Merz, A. J.; So, M.; Sheetz, M. P., Pilus Retraction Powers Bacterial Twitching Motility. Nature 2000, 407, 98-102.

[28] Mirnezami, A., et al. Increased local recurrence and reduced survival from colorectal cancer following anastomotic leak: systematic review and meta-analysis. Annals of surgery 253, 890-899 (2011).

[29] McArdle, C., McMillan, D. & Hole, D. Impact of anastomotic leakage on long-term survival of patients undergoing curative resection for colorectal cancer. British Journal of Surgery 92, 1150-1154 (2005).

[30] Law, W. L., Choi, H. K., Lee, Y. M., Ho, J. W. & Seto, C. L. Anastomotic leakage is associated with poor long-term outcome in patients after curative colorectal resection for malignancy. Journal of Gastrointestinal Surgery 11, 8-15 (2007).

[31] Kingham, T. P. & Pachter, H. L. Colonic anastomotic leak: risk factors, diagnosis, and treatment. Journal of the American College of Surgeons 208, 269-278 (2009).

[32] Karliczek, A., et al. Surgeons lack predictive accuracy for anastomotic leakage in gastrointestinal surgery. Int J Colorectal Dis 24, 569-576 (2009).

[33] Shogan, B. D., et al. Collagen degradation and MMP9 activation by *Enterococcus faecalis* contribute to intestinal anastomotic leak. Sci Transl Med 7, 286ra268 (2015).

[34] Stern, J. R., et al. Agent-based model of epithelial host-pathogen interactions in anastomotic leak. J Surg Res 184, 730-738 (2013).

[35] Hyoju, S. K., et al. Oral Polyphosphate Suppresses Bacterial Collagenase Production and Prevents Anastomotic Leak Due to *Serratia marcescens* and *Pseudomonas aeruginosa*. Ann Surg (2017).

[36] Olivas, A. D., et al. Intestinal tissues induce an SNP mutation in *Pseudomonas aeruginosa* that enhances its virulence: possible role in anastomotic leak. PLoS One 7, e44326 (2012).

[37] Lahteenmaki, K., Edelman, S. & Korhonen, T. K. Bacterial metastasis: the host plasminogen system in bacterial invasion. Trends Microbiol 13, 79-85 (2005).

[38] Cronberg, S., Skinsberg, P. & Nivenius-Larsson, K. Disseminated intravascular coagulation in septicemia caused by beta-hemolytic streptococci. Thrombosis Research 3, 405-411 (1973).

[39] Kawao, N., et al. Role of plasminogen in macrophage accumulation during liver repair. Thromb Res 125, e214-221 (2010).

[40] Sulniute, R., et al. Plasminogen is a critical regulator of cutaneous wound healing. Thromb Haemost 115, 1001-1009 (2016).

[41] te Velde, E. A., et al. Impaired healing of cutaneous wounds and colonic anastomoses in mice lacking thrombin-activatable fibrinolysis inhibitor. J Thromb Haemost 1, 2087-2096 (2003).

[42] Boyle, M. D. & Lottenberg, R. Plasminogen activation by invasive human pathogens. Thromb Haemost 77, 1-10 (1997).

[43] Te Velde, E. A., et al. Impaired healing of cutaneous wounds and colonic anastomoses in mice lacking thrombin-activatable fibrinolysis inhibitor. Journal of Thrombosis and Haemostasis 1, 2087-2096 (2003).

[44] Jacovina, A. T., et al. Neuritogenesis and the nerve growth factor-induced differentiation of PC-12 cells requires annexin II-mediated plasmin generation. J Biol Chem 276, 49350-49358 (2001).

[45] Hara, T., et al. Molecular imaging of fibrin deposition in deep vein thrombosis using fibrin-targeted near-infrared fluorescence. JACC Cardiovasc Imaging 5, 607-615 (2012).

[46] McCormack, P. L. Tranexamic acid. Drugs 72, 585-617 (2012).

[47] Shakhsheer, B. A., et al. Morphine Promotes Colonization of Anastomotic Tissues with Collagenase—Producing *Enterococcus faecalis* and Causes Leak. J Gastrointest Surg 20, 1744-1751 (2016).

[48] Yuasa, M., et al. Fibrinolysis is essential for fracture repair and prevention of heterotopic ossification. J Clin Invest 125, 3117-3131 (2015).

1'. A. Karliczek, N. J. Harlaar, C. J. Zeebregts, T. Wiggers, P. C. Baas, G. M. van Dam, Surgeons lack predictive accuracy for anastomotic leakage in gastrointestinal surgery. Int J Colorectal Dis 24, 569-576 (2009).

2'. T. L. Hedrick, R. G. Sawyer, E. F. Foley, C. M. Friel, Anastomotic leak and the loop ileostomy: friend or foe? Dis Colon Rectum 49, 1167-1176 (2006).

3'. J. E. Scarborough, C. R. Mantyh, Z. Sun, J. Migaly, Combined Mechanical and Oral Antibiotic Bowel Preparation Reduces Incisional Surgical Site Infection and Anastomotic Leak Rates After Elective Colorectal Resection: An Analysis of Colectomy-Targeted ACS NSQIP. Ann Surg 262, 331-337 (2015).

4'. I. Cohn, Jr., J. D. Rives, Antibiotic protection of colon anastomoses. *Ann Surg* 141, 707-717 (1955).

5'. G. Branagan, D. Finnis, G. Wessex Colorectal Cancer Audit Working, Prognosis after anastomotic leakage in colorectal surgery. *Dis Colon Rectum* 48, 1021-1026 (2005).

6'. R. P. Kiran, A. C. Murray, C. Chiuzan, D. Estrada, K. Forde, Combined preoperative mechanical bowel preparation with oral antibiotics significantly reduces surgical site infection, anastomotic leak, and ileus after colorectal surgery. *Ann Surg* 262, 416-425; discussion 423-415 (2015).

7'. A. Teillant, S. Gandra, D. Barter, D. J. Morgan, R. Laxminarayan, Potential burden of antibiotic resistance on surgery and cancer chemotherapy antibiotic prophylaxis in the USA: a literature review and modelling study. *Lancet Infect Dis* 15, 1429-1437 (2015).

8'. S. K. Hyoju, R. E. Klabbers, M. Aaron, M. A. Krezalek, A. Zaborin, M. Wiegerinck, N. H. Hyman, O. Zaborina, H. Van Goor, J. C. Alverdy, Oral Polyphosphate Suppresses Bacterial Collagenase Production and Prevents Anastomotic Leak Due to *Serratia marcescens* and *Pseudomonas aeruginosa*. *Ann Surg*, (2017).

9'. B. A. Shakhsheer, L. A. Versten, J. N. Luo, J. R. Defazio, R. Klabbers, S. Christley, A. Zaborin, K. L. Guyton, M. Krezalek, D. P. Smith, N. J. Ajami, J. F. Petrosino, I. D. Fleming, N. Belogortseva, O. Zaborina, J. C. Alverdy, Morphine Promotes Colonization of Anastomotic Tissues with Collagenase—Producing *Enterococcus faecalis* and Causes Leak. *J Gastrointest Surg* 20, 1744-1751 (2016).

10'. B. D. Shogan, N. Belogortseva, P. M. Luong, A. Zaborin, S. Lax, C. Bethel, M. Ward, J. P. Muldoon, M. Singer, G. An, K. Umanskiy, V. Konda, B. Shakhsheer, J. Luo, R. Klabbers, L. E. Hancock, J. Gilbert, O. Zaborina, J. C. Alverdy, Collagen degradation and MMP9 activation by *Enterococcus faecalis* contribute to intestinal anastomotic leak. *Sci Transl Med* 7, 286ra268 (2015).

11'. E. A. te Velde, G. T. Wagenaar, A. Reijerkerk, M. Roose-Girma, I. H. Borel Rinkes, E. E. Voest, B. N. Bouma, M. F. Gebbink, J. C. Meijers, Impaired healing of cutaneous wounds and colonic anastomoses in mice lacking thrombin-activatable fibrinolysis inhibitor. *J Thromb Haemost* 1, 2087-2096 (2003).

12'. M. Yuasa, N. A. Mignemi, J. S. Nyman, C. L. Duvall, H. S. Schwartz, A. Okawa, T. Yoshii, G. Bhattacharjee, C. Zhao, J. E. Bible, W. T. Obremskey, M. J. Flick, J. L. Degen, J. V. Barnett, J. M. Cates, J. G. Schoenecker, Fibrinolysis is essential for fracture repair and prevention of heterotopic ossification. *J Clin Invest* 125, 3117-3131 (2015).

13'. J. Romer, T. H. Bugge, C. Pyke, L. R. Lund, M. J. Flick, J. L. Degen, K. Dano, Impaired wound healing in mice with a disrupted plasminogen gene. *Nat Med* 2, 287-292 (1996).

14'. Y. Gong, E. Hart, A. Shchurin, J. Hoover-Plow, Inflammatory macrophage migration requires MMP-9 activation by plasminogen in mice. *J Clin Invest* 118, 3012-3024 (2008).

15'. H. R. Lijnen, J. Silence, G. Lemmens, L. Frederix, D. Collen, Regulation of gelatinase activity in mice with targeted inactivation of components of the plasminogen/plasmin system. *Thromb Haemost* 79, 1171-1176 (1998).

16'. S. Arumugam, Y. C. Jang, C. Chen-Jensen, N. S. Gibran, F. F. Isik, Temporal activity of plasminogen activators and matrix metalloproteinases during cutaneous wound repair. *Surgery* 125, 587-593 (1999).

17'. K. Lahteenmaki, S. Edelman, T. K. Korhonen, Bacterial metastasis: the host plasminogen system in bacterial invasion. *Trends Microbiol* 13, 79-85 (2005).

18'. S. A. Cederholm-Williams, F. De Cock, H. R. Lijnen, D. Collen, Kinetics of the reactions between streptokinase, plasmin and alpha 2-antiplasmin. *Eur J Biochem* 100, 125-132 (1979).

19'. A. Kunert, J. Losse, C. Gruszin, M. Huhn, K. Kaendler, S. Mikkat, D. Volke, R. Hoffmann, T. S. Jokiranta, H. Seeberger, U. Moellmann, J. Hellwage, P. F. Zipfel, Immune evasion of the human pathogen *Pseudomonas aeruginosa*: elongation factor Tuf is a factor H and plasminogen binding protein. *J Immunol* 179, 2979-2988 (2007).

20'. A. Benachour, T. Morin, L. Hebert, A. Budin-Verneuil, A. Le Jeune, Y. Auffray, V. Pichereau, Identification of secreted and surface proteins from *Enterococcus faecalis*. *Can J Microbiol* 55, 967-974 (2009).

21'. A. Redlitz, B. J. Fowler, E. F. Plow, L. A. Miles, The role of an enolase-related molecule in plasminogen binding to cells. *Eur J Biochem* 227, 407-415 (1995).

22'. L. A. Miles, E. F. Plow, Binding and activation of plasminogen on the platelet surface. *J Biol Chem* 260, 4303-4311 (1985).

23'. C.-t. collaborators, H. Shakur, I. Roberts, R. Bautista, J. Caballero, T. Coats, Y. Dewan, H. El-Sayed, T. Gogichaishvili, S. Gupta, J. Herrera, B. Hunt, P. Iribhogbe, M. Izurieta, H. Khamis, E. Komolafe, M. A. Marrero, J. Mejia-Mantilla, J. Miranda, C. Morales, O. Olaomi, F. Olldashi, P. Perel, R. Peto, P. V. Ramana, R. R. Ravi, S. Yutthakasemsunt, Effects of tranexamic acid on death, vascular occlusive events, and blood transfusion in trauma patients with significant haemorrhage (CRASH-2): a randomised, placebo-controlled trial. *Lancet* 376, 23-32 (2010).

24'. N. Beaufort, P. Seweryn, S. de Bentzmann, A. Tang, J. Kellermann, N. Grebenchtchikov, M. Schmitt, C. P. Sommerhoff, D. Pidard, V. Magdolen, Activation of human pro-urokinase by unrelated proteases secreted by *Pseudomonas aeruginosa*. *Biochem J* 428, 473-482 (2010).

25'. P. Kuusela, O. Saksela, Binding and activation of plasminogen at the surface of *Staphylococcus aureus*. Increase in affinity after conversion to the Lys form of the ligand. *Eur J Biochem* 193, 759-765 (1990).

26'. L. A. Miles, V. Ellis, Alpha-enolase comes muscling in on plasminogen activation. *Thromb Haemost* 90, 564-566 (2003).

27'. P. A. Fontan, V. Pancholi, M. M. Nociari, V. A. Fischetti, Antibodies to streptococcal surface enolase react with human alpha-enolase: implications in poststreptococcal sequelae. *J Infect Dis* 182, 1712-1721 (2000).

28'. W. L. Hesp, T. Hendriks, P. H. Schillings, E. J. Lubbers, H. H. de Boer, Histological features of wound repair: a comparison between experimental ileal and colonic anastomoses. *Br J Exp Pathol* 66, 511-518 (1985).

29'. B. M. Schafer, K. Maier, U. Eickhoff, R. F. Todd, M. D. Kramer, Plasminogen activation in healing human wounds. *Am J Pathol* 144, 1269-1280 (1994).

30'. D. A. Waltz, L. Z. Sailor, H. A. Chapman, Cytokines induce urokinase-dependent adhesion of human myeloid cells. A regulatory role for plasminogen activator inhibitors. *J Clin Invest* 91, 1541-1552 (1993).

31'. A. Diaz-Ramos, A. Roig-Borrellas, A. Garcia-Melero, R. Lopez-Alemany, alpha-Enolase, a multifunctional protein: its role on pathophysiological situations. *J Biomed Biotechnol* 2012, 156795 (2012).

32'. B. D. Shogan, D. P. Smith, S. Christley, J. A. Gilbert, O. Zaborina, J. C. Alverdy, Intestinal anastomotic injury alters spatially defined microbiome composition and function. *Microbiome* 2, 35 (2014).

33'. A. Zaborin, K. Romanowski, S. Gerdes, C. Holbrook, F. Lepine, J. Long, V. Poroyko, S. P. Diggle, A. Wilke, K. Righetti, I. Morozova, T. Babrowski, D. C. Liu, O.

Zaborina, J. C. Alverdy, Red death in *Caenorhabditis elegans* caused by *Pseudomonas aeruginosa* PAO1. *Proc Natl Acad Sci USA* 106, 6327-6332 (2009).

34'. T. L. Weir, D. K. Manter, A. M. Sheflin, B. A. Barnett, A. L. Heuberger, E. P. Ryan, Stool microbiome and metabolome differences between colorectal cancer patients and healthy adults. *PLoS One* 8, e70803 (2013).

35'. M. Hayakawa, T. Asahara, N. Henzan, H. Murakami, H. Yamamoto, N. Mukai, Y. Minami, M. Sugano, N. Kubota, S. Uegaki, H. Kamoshida, A. Sawamura, K. Nomoto, S. Gando, Dramatic changes of the gut flora immediately after severe and sudden insults. *Dig Dis Sci* 56, 2361-2365 (2011).

36'. J. S. Clarke, R. E. Condon, J. G. Bartlett, S. L. Gorbach, R. L. Nichols, S. Ochi, Preoperative oral antibiotics reduce septic complications of colon operations: results of prospective, randomized, double-blind clinical study. *Ann Surg* 186, 251-259 (1977).

37'. L. Oliveira, S. D. Wexner, N. Daniel, D. DeMarta, E. G. Weiss, J. J. Nogueras, M. Bernstein, Mechanical bowel preparation for elective colorectal surgery. A prospective, randomized, surgeon-blinded trial comparing sodium phosphate and polyethylene glycol-based oral lavage solutions. *Dis Colon Rectum* 40, 585-591 (1997).

38'. S. J. Atkinson, B. R. Swenson, D. J. Hanseman, E. F. Midura, B. R. Davis, J. F. Rafferty, D. E. Abbott, S. A. Shah, I. M. Paquette, In the Absence of a Mechanical Bowel Prep, Does the Addition of Pre-Operative Oral Antibiotics to Parental Antibiotics Decrease the Incidence of Surgical Site Infection after Elective Segmental Colectomy?*Surg Infect* (Larchmt) 16, 728-732 (2015).

39'. M. Ojima, D. Motooka, K. Shimizu, K. Gotoh, A. Shintani, K. Yoshiya, S. Nakamura, H. Ogura, T. Iida, T. Shimazu, Metagenomic Analysis Reveals Dynamic Changes of Whole Gut Microbiota in the Acute Phase of Intensive Care Unit Patients. *Dig Dis Sci* 61, 1628-1634 (2016).

40'. S. Ohigashi, K. Sudo, D. Kobayashi, T. Takahashi, K. Nomoto, H. Onodera, Significant changes in the intestinal environment after surgery in patients with colorectal cancer. *J Gastrointest Surg* 17, 1657-1664 (2013).

41'. P. Augustin, G. Alsalih, Y. Launey, S. Delbosc, L. Louedec, V. Ollivier, F. Chau, P. Montravers, X. Duval, J. B. Michel, O. Meilhac, Predominant role of host proteases in myocardial damage associated with infectious endocarditis induced by *Enterococcus faecalis* in a rat model. *Infect Immun* 81, 1721-1729 (2013).

42'. S. Bhattacharya, V. A. Ploplis, F. J. Castellino, Bacterial plasminogen receptors utilize host plasminogen system for effective invasion and dissemination. *J Biomed Biotechnol* 2012, 482096 (2012).

43'. X. Qin, K. V. Singh, G. M. Weinstock, B. E. Murray, Effects of *Enterococcus faecalis* fsr genes on production of gelatinase and a serine protease and virulence. *Infect Immun* 68, 2579-2586 (2000).

44'. L. R. Johnston, C. J. Rodriguez, E. A. Elster, M. J. Bradley, Evaluation of Military Use of Tranexamic Acid and Associated Thromboembolic Events. *JAMA Surg* 153, 169-175 (2018).

45'. S. Almer, T. Andersson, M. Strom, Pharmacokinetics of tranexamic acid in patients with ulcerative colitis and in healthy volunteers after the single instillation of 2 g rectally. *J Clin Pharmacol* 32, 49-54 (1992).

46'. M. V. Cubellis, T. C. Wun, F. Blasi, Receptor-mediated internalization and degradation of urokinase is caused by its specific inhibitor PAI-1. *EMBO J* 9, 1079-1085 (1990).

47'. B. Wiman, D. Collen, On the mechanism of the reaction between human alpha 2-antiplasmin and plasmin. *J Biol Chem* 254, 9291-9297 (1979).

48'. V. C. Thomas, L. R. Thurlow, D. Boyle, L. E. Hancock, Regulation of autolysis-dependent extracellular DNA release by *Enterococcus faecalis* extracellular proteases influences biofilm development. *J Bacteriol* 190, 5690-5698 (2008).

49'. P. M. Luong, B. D. Shogan, A. Zaborin, N. Belogortseva, J. D. Shrout, O. Zaborina, J. C. Alverdy, Emergence of the P2 phenotype in *Pseudomonas aeruginosa* PAO1 strains involves various mutations in mexT or mexF. *J Bacteriol* 196, 504-513 (2014).

50'. S. Ambadapadi, G. Munuswamy-Ramanujam, D. Zheng, C. Sullivan, E. Dai, S. Morshed, B. McFadden, E. Feldman, M. Pinard, R. McKenna, S. Tibbetts, A. Lucas, Reactive Center Loop (RCL) Peptides Derived from Serpins Display Independent Coagulation and Immune Modulating Activities. *J Biol Chem* 291, 2874-2887 (2016).

51'. R. T. Aimes, J. P. Quigley, Matrix metalloproteinase-2 is an interstitial collagenase. Inhibitor-free enzyme catalyzes the cleavage of collagen fibrils and soluble native type I collagen generating the specific 3/4- and 1/4-length fragments. *J Biol Chem* 270, 5872-5876 (1995).

52'. K. Bower, S. P. Djordjevic, N. M. Andronicos, M. Ranson, Cell surface antigens of *Mycoplasma* species bovine group 7 bind to and activate plasminogen. *Infect Immun* 71, 4823-4827 (2003).

53'. A. Itzek, C. M. Gillen, M. Fulde, C. Friedrichs, A. C. Rodloff, G. S. Chhatwal, D. P. Nitsche-Schmitz, Contribution of plasminogen activation towards the pathogenic potential of oral streptococci. *PLoS One* 5, e13826 (2010).

54'. J. Isenring, J. Kohler, M. Nakata, M. Frank, C. Jans, P. Renault, C. Danne, S. Dramsi, B. Kreikemeyer, S. Oehmcke-Hecht, *Streptococcus* gallolyticus subsp. gallolyticus endocarditis isolate interferes with coagulation and activates the contact system. *Virulence* 9, 248-261 (2018).

55'. A. Molla, T. Akaike, H. Maeda, Inactivation of various proteinase inhibitors and the complement system in human plasma by the 56-kilodalton proteinase from *Serratia marcescens*. *Infect Immun* 57, 1868-1871 (1989).

56'. T. L. M. Stephen F. Altschul, Alejandro A. Schaffer, Jinghui Zhang, Zheng Zhang, Webb Miller, and David J. Lipman Gapped BLAST and PSI-BLAST: a new generation of protein database search programs. *Nucleic Acids Res* 25, 3389-3402 (1997).

Each of the references cited herein is hereby incorporated by reference in its entirety or in pertinent part, as would be apparent from the context of the citation.

From the disclosure herein it will be appreciated that, although specific embodiments of the disclosure have been described herein for purposes of illustration, various modifications may be made without deviating from the spirit and scope of the disclosure.

What is claimed is:

1. A pharmaceutical composition comprising a plasminogen inhibitor and a phosphate-loaded triblock copolymer, wherein the triblock copolymer comprises:
   (a) a hydrophobic core; and
   (b) at least two polyethylene glycol chains,
   wherein
   at least one of the said two polyethylene glycol chains is a phosphorylated polyethylene glycol comprising more than two phosphate groups, and
   the dispersity (Ð) of the copolymer is less than or equal to 1.10.

2. The pharmaceutical composition of claim 1 wherein the phosphate-loaded triblock copolymer is a phosphorylated form of ABA-polyethylene glycol-polyglycidol (ABA-PEG-PGly) or ABA-polyethylene-glycol-polyethoxyethyl glycidyl ether (ABA-PEG-PEEGE).

3. The pharmaceutical composition of claim 1 wherein the phosphorylated polyethylene glycol is ABA-PEG20k-Pi20.

4. The pharmaceutical composition of claim 1 wherein the plasminogen inhibitor is tranexamic acid, F-aminocaproic acid, plasminogen activator inhibitor-1, plasminogen activator inhibitor-2, plasminogen activator inhibitor-3, or antiplasmin.

5. The composition of claim 4 wherein the antiplasmin is alpha-2-antiplasmin.

6. The composition of claim 4 wherein the plasminogen inhibitor is tranexamic acid.

7. A method of treating anastomotic leak comprising administering the composition of claim 1.

8. A method of reducing the risk of acquiring anastomotic leak comprising administering the composition of claim 1.

* * * * *

SEQUENCE LISTING

```
<160> NUMBER OF SEQ ID NOS: 3

<210> SEQ ID NO 1
<211> LENGTH: 24
<212> TYPE: DNA
<213> ORGANISM: Pseudomonas aeruginosa
<220> FEATURE:
<221> NAME/KEY: misc_feature
<223> OTHER INFORMATION: PCR forward primer PstS F

<400> SEQUENCE: 1
cacctatccc aaaacccctg gtca                                              24

<210> SEQ ID NO 2
<211> LENGTH: 24
<212> TYPE: DNA
<213> ORGANISM: Pseudomonas aeruginosa
<220> FEATURE:
<221> NAME/KEY: misc_feature
<223> OTHER INFORMATION: PCR reverse primer PstS R

<400> SEQUENCE: 2
caaacgcttg agtttcatgc cttg                                              24

<210> SEQ ID NO 3
<211> LENGTH: 16
<212> TYPE: PRT
<213> ORGANISM: Artificial Seuqence
<220> FEATURE:
<223> OTHER INFORMATION: Synthetic Peptide

<400> SEQUENCE: 3

Cys Ala Glu Tyr Lys Gly Leu Lys Ser Phe Tyr Asn Leu Lys Asn Lys
1               5                   10                  15
```